United States Patent
Switzer et al.

(10) Patent No.: US 8,663,968 B2
(45) Date of Patent: Mar. 4, 2014

(54) SIMIAN T-CELL LYMPHOTROPIC VIRUS

(75) Inventors: William M. Switzer, Stone Mountain, GA (US); Walid Heneine, Atlanta, GA (US); Thomas M. Folks, Lithonia, GA (US); Nathan D. Wolfe, Los Angeles, CA (US); Donald S. Burke, Pittsburgh, PA (US); David M. Sintasath, Atlanta, GA (US)

(73) Assignees: The United States of America as Represented by the Secretary of the Department of Health and Human Services, Centers for Disease Control and Prevention, Washington, DC (US); Johns Hopkins University, Baltimore, MD (US)

(*) Notice: Subject to any disclaimer, the term of this patent is extended or adjusted under 35 U.S.C. 154(b) by 916 days.

(21) Appl. No.: 12/600,995

(22) PCT Filed: May 20, 2008

(86) PCT No.: PCT/US2008/064270
§ 371 (c)(1),
(2), (4) Date: Nov. 19, 2009

(87) PCT Pub. No.: WO2008/144700
PCT Pub. Date: Nov. 27, 2008

(65) Prior Publication Data
US 2010/0160420 A1    Jun. 24, 2010

Related U.S. Application Data

(60) Provisional application No. 60/990,138, filed on Nov. 26, 2007, provisional application No. 60/939,304, filed on May 21, 2007.

(51) Int. Cl.
*C12N 15/09* (2006.01)
*C12N 7/00* (2006.01)
*A61K 39/00* (2006.01)

(52) U.S. Cl.
USPC .................................................. 435/235.1

(58) Field of Classification Search
None
See application file for complete search history.

(56) References Cited

U.S. PATENT DOCUMENTS

| 4,753,873 A | 6/1988 | Beltz et al. |
| 4,816,387 A | 3/1989 | Osther |

(Continued)

FOREIGN PATENT DOCUMENTS

WO    WO 2006/091511    8/2006

OTHER PUBLICATIONS

Lal, et al., Isotypic and IgG Subclass Restriction of the Humoral Immune Responses to Human T-Lymphotropic Virus Type-I. Clin. Immunol. Immunopathol. 1993; 67(1):40-49.—Abstract Only.*

(Continued)

*Primary Examiner* — Zachariah Lucas
*Assistant Examiner* — Stuart W Snyder
(74) *Attorney, Agent, or Firm* — Klarquist Sparkman, LLP

(57) ABSTRACT

Disclosed are the simian T-cell lymphotropic virus type 3 subtype D (STLV-3 subtype D), isolated nucleic acid molecules encoding STLV-3 subtype D polypeptides, such as STLV-3 subtype D envelope, protease, polymerase, tax, rex, and capsid polypeptides, isolated polypeptides encoded by such nucleic acids. Methods are also disclosed for detecting STLV-3 subtype D, for example by detecting a STLV-3 subtype D nucleic acid or polypeptide in the sample. Accordingly, probes, primers, and antibodies for use in detecting STLV-3 subtype D nucleic acids or polypeptides are disclosed. Therapeutic compositions which included isolated nucleic acid molecules encoding a STLV-3 subtype D polypeptides or isolated polypeptides encoded by such nucleic acid molecules are also disclosed.

8 Claims, 7 Drawing Sheets

(56) References Cited

U.S. PATENT DOCUMENTS

| | | |
|---|---|---|
| 4,879,212 A | 11/1989 | Wang et al. |
| 5,674,705 A | 10/1997 | Papas et al. |
| 6,406,841 B1 | 6/2002 | Lee et al. |

OTHER PUBLICATIONS

Busch et al., "Absence of evidence of infection with divergent primate T-lymphotropic viruses in United States blood donors who have seroindeterminate HTLV test results," *Transfusion*, 40:443-449, 2000.

Calattini et al., "Discovery of a new human T-cell lymphotropic virus (HTLV-3) in Central Africa," *Retrovirology*, 2:30, 2005.

Courgnaud et al., "Simian T-Cell Leukemia Virus (STLV) Infection in Wild Primate Populations in Cameroon: Evidence for Dual STLV Type 1 and Type 3 Infection in Agile Mangabeys (*Cercocebus agilis*)," *J. Virol.*, 78(9):4700-4709, 2004.

Liegeois et al., "Identification and molecular characterization of new STLV-1 and STLV-3 strains in wild-caught nonhuman primates in Cameroon," *Virology*, 371(2):405-417, 2008.

Mahieux et al., "Molecular epidemiology of 58 new African human T-cell leukemia virus type 1 (HTLV-1) strains: identification of a new and distinct HTLV-1 molecular subtype in Central Africa and in Pygmies," *J. Virol.*, 71:1317-1333, 1997.

Makuwa et al., "A New STLV-1 in a household pet *Cercopithecus nictitans* from Gabon," *AIDS Res. Hum. Retroviruses*, 20(6):679-683, 2004.

Meertens and Gessain, "Divergent Simian T-Cell Lymphotropic Virus Type 3 (STLV-3) in Wild-Caught *Papio Hamadryas Papio* from Senegal: Widespread Distribution of STLV-3 in Africa," *J. Virol.*, 77(1):782-789, 2003.

Meertens et al., "Molecular and phylogenetic analyses of 16 novel simian T cell leukemia virus type 1 from Africa: close relationship of STLV-1 from Allenopithecus nigroviridis to HTLV-1 subtype B strains," *Virology*, 287:275-285, 2001.

Meertens et al., "Complete Sequence of a Novel Highly Divergent Simian T-Cell Lymphotropic Virus from Wild-Caught Red-Capped Mangabeys (*Cercocebus torquatus*) from Cameroon: a New Primate T-Lymphotropic Virus Type 3 Subtype," *J. Virol.*, 76(1):259-268, 2002.

Meertens et al., "A novel, divergent simian T-cell lymphotropic virus type 3 in a wild-caught red-capped mangabey (*Cercocebus torquatus torquatus*) from Nigeria," *J. Gen. Virol.*, 84(10):2723-2727, 2003.

Nerrienet et al., "Simian T cell leukaemia virus type I subtype B in a wild-caught gorilla (*Gorilla gorilla gorilla*) and chimpanzee (*Pan troglodytes vellerosus*) from Cameroon," *J. Gen. Virol.*, 85:25-29, 2004.

Salemi et al., "Two new human T-lymphotropic virus type I phylogenetic subtypes in seroindeterminates, a Mbuti pygmy and a Gabonese, have closest relatives among African STLV-I strains," *Virology*, 246:277-287, 1998.

Salemi et al., "Origin and Evolution of Human and Simian T-Cell Lymphotropic Viruses," *AIDS Rev.*, 1:131-139, 1999.

Slattery et al., "Genomic evolution, patterns of global dissemination, and interspecies transmission of human and simian T-cell leukemia/lymphotropic viruses," *Genome Res.* 9(6):525-40, 1999.

Switzer et al., "Ancient co-speciation of simian foamy viruses and primates," *Nature*, 434:376-380, 2005.

Switzer et al., "Ancient Origin and Molecular Features of the Novel Human T-Lymphotropic Virus Type 3 Revealed by Complete Genome Analysis," *J. Virol.*, 80:7427-7438, 2006.

Takemura et al., "High Prevalence of Simian T-Lymphotropic Virus Type L in Wild Ethiopian Baboons," *J. Virol.*, 76(4):1642-1648, 2002.

Van Brüssel et al., "Complete Nucleotide Sequence of the New Simian T-Lymphotropic Virus, STLV-PH969 from a Hamadryas Baboon, and Unusual Features of Its Long Terminal Repeat," *J. Virol.*, 71(7):5464-5472, 1997.

Van Brüssel et al., "The Simian T-Lymphotropic Virus STLV-PP1664 from *Pan paniscus* is Distinctly Related to HTLV-2 but Differs in Genomic Organization," *Virology*, 245:366-379, 1998.

Van Brüssel et al., "The discovery of two new divergent STLVs has implications for the evolution and epidemiology of HTLVs," *Rev. Med. Virol.*, 9:155-170, 1999.

Van Dooren et al., "Letter to the Editor: Evidence for a Second Simian T-Cell Lymphtropic Virus Type 3 in *Cercopithecus nictitans* from Cameroon," *J. Virol.*, 75(23):11939-11941, 2001.

Van Dooren et al., "Identification in gelada baboons (*Theropithecus gelada*) of a distinct simian T-cell lymphotropic virus type 3 with a broad range of Western blot reactivity," *J. Gen. Virol.*, 85(2):507-519, 2004.

Vandamme et al., "African origin of human T-lymphotropic virus type 2 (HTLV-2) supported by a potential new HTLV-2d subtype in Congolese Bambuti Efe Pygmies," *J. Virol.*, 72:4327-4340, 1998.

Wolfe et al., "Naturally acquired simian retrovirus infections in central African hunters," *The Lancet*, 363(9413):932-937, 2004.

Wolfe et al., "Emergence of unique primate T-lymphotropic viruses among central African bushmeat hunters, " *Proc. Natl. Acad. Sci. U.S.A.*,102:7994-7999, 2005.

International Search Report, PCT US2008/064270, issued Nov. 21, 2008.

* cited by examiner

PTLV-1
LTR (510-bp)

PTLV-3

| | Subtype D | | Subtype C | | | | Subtype B | | | | Subtype A | |
|---|---|---|---|---|---|---|---|---|---|---|---|---|
| | Cmo8699AB[2] | Cni7867AB[2] | Cni217[3] | Cni227[3] | Cni3034[4] | Cni3038[5] | 2026ND | Cto604 | CtoNG409 | PPAF3 | Ph969 | Tge2117 |
| Cmo8699AB | - | 98.9 | 92.7 | 93.2 | 93.5 | 93.1 | 82.7 | 83.4 | 83.5 | 83.5 | 84.5 | 84.2 |
| Cni7867AB | | - | 92.7 | 93.2 | 93.5 | 93.1 | 82.7 | 83.4 | 83.5 | 83.5 | 84.5 | 84.2 |
| Cni217 | | | - | 99.3 | 98.2 | 98.5 | 84.5 | 86.3 | 88.1 | 86.8 | 88.6 | 88.1 |
| Cni227 | | | | - | 98.8 | 99.1 | 84.9 | 86.8 | 87.7 | 87.2 | 89.0 | 88.6 |
| Cni3034 | | | | | - | 100.0 | 82.2 | 82.4 | 82.8 | 83.6 | 83.9 | 83.7 |
| Cni3038 | | | | | | - | 82.5 | 82.7 | 83.1 | 83.7 | 84.1 | 83.9 |
| 2026ND | | | | | | | - | 91.6 | 93.0 | 94.1 | 87.0 | 90.4 |
| Cto604 | | | | | | | | - | 92.4 | 92.5 | 87.5 | 92.0 |
| CtoNG409 | | | | | | | | | - | 94.2 | 86.8 | 90.7 |
| PPAF3 | | | | | | | | | | - | 88.5 | 90.8 |
| Ph969 | | | | | | | | | | | - | 95.8 |
| Tge2117 | | | | | | | | | | | | - |

[1] Boxed and shaded cells indicate inter-subgroup and intra-subgroup identities, respectively
[2] Partial tax sequence (1015-bp)
[3] Partial tax sequence (219-bp)
[4] Partial tax sequence (170-bp)
[5] Partial tax sequence (202-bp)

FIG. 7

SEQUENCE LISTING

```
<160> NUMBER OF SEQ ID NOS: 26

<210> SEQ ID NO 1
<211> LENGTH: 8913
<212> TYPE: DNA
<213> ORGANISM: STLV-3 subtype D

<400> SEQUENCE: 1
tgacagtgac agcaagcccc aaggcgagcc acaactacta gccaaagggc atacagttga        60
atcatctgtc tagggacgt ctcgcaccca gagtatgtcc aaagaacacc agggctctga       120
cgtctctccc tgccttgtct cccggaaaaa accttaaacc acccatttcc tcatgtttgc       180
ccaaggctct gacgataacc ctgaaaaatt tgactaacaa ataaaggaac ctggacccta       240 taaagggga gagcgaccta aaatgggat caaccttttc tccccaacgc cctttcgcgc         300
cccgcggaca gccactgtcc gggctactcc tggcctacct agatcattgc tccgcgcccg       360
agccattctt ctgcagccaa gcggcacctt gccacttcgc ttctcctgtc ctggtaagat       420
cccactgggt agagctaggc cgttactccc tggccgctcc cctggagctc ctttgcttag       480
ctcttaaggt cgctctctcc ttctcgttag ggtccaagga ctaactttac ttccgtgtct       540
cggtctcctt tctttggcgg tctcgtctaa agtcgaaagt aacacctcaa actgtcagca       600
gcgaggcctg gcccggggcc agcgcctgtg agctttactc ggctcggagc caggggctca       660
gaaagtaaag gctgtagctg ccagcctttg aggggaacca aaaacaggtg ggggctcgtc       720
cgggattgat caccctccta ttaaacatgg gaaattcata cagccgtgcc gccaaccccca      780 tccccaaggc cccaaaaggg ctagcaattc accactggtt aaactttcta caagctgcct       840
atcggctgca accggggccc tcagagtttg atttccatca gttacgaaat tttcttaaat       900
tagctataaa aaccctgtt tggctaaacc ccatcaatta ttccgtccta gctgaactcg        960
ttcctaaaaa ttatccaggc agaatccaag aaattatagc catcctaatc caagaaacct      1020
ctacgcagga ggttccccca tccgccccac cggccagcga accccaaaat ccccgccctt      1080
atccagaacc agggcaagcc ataccccagt gcctacctgt tctgcacccc catggtgccc      1140
ctgccgccca tcgcccttgg cagatgaaag atctccaagc tataaaacag gaagttacct      1200
cttccgcacc agggagccct cagttcatgc aaaccgtgcg cctggcagtc caacaatttg      1260
acccgactgc caaagacctc catgacctct tacaatacct gtgctcctca ctagttgcct      1320
ccctgcacca ccagcagctc gagaccctca tcgctcaggt tgaaacccaa gggataaccg      1380
gatataatcc cctggccggc ccctgcgag tacaggccaa caaccccaact cagcaagggc      1440 tccggcgaga ataccaaaac ttatggctgt cggccttttc tgccctccca ggaaatacta      1500 aagacccac ctgggcggca atcctccagg gccccgagga accgttttgc acattcgtag      1560
aaagacttaa tgtggcccta gacaacggcc tccctgaagg aacccccaaa gagcctattc      1620
ttcggtcctt agcatattct aatgccaaca agaatgcca gaaactccta caagcccgag      1680
ggcagacaaa cggtcccttaa ggggacatgc tcagagcttg ccaggcgtgg acgccccggg     1740
acaaaaacaa agtactaatg gtccaaccta aaagacacc tcccccaaat caaccatgct     1800
tccggtgcgg gcaggcgggc cactggagca gagactgtaa acaacctcgt ccccccccag     1860
gcccatgtcc gctctgtcaa gaccccaccc actggaagcg agattgcccg cagctaaaac     1920
```

```
cagatcctga agaaggcatg ttgttagatc tgccttgtga agacccagcg gccagagacc    1980
aaaaaaactt cataggggg gaggactagc ctcccccaa acagtgctgc cttttatacc     2040
attatcccag caaaaacaac cagtcctaca cgtccgagta tccttcccag gtacccccc    2100 agtaagcatc caggcgcttt tagacacagg ggcagatgta accgtcctcc cagcccgtct    2160
atgcccccct gacctaaaat tacaagacac cactgtcctt ggagccagcg ggccaagcac    2220
cgacaagttt aaagttctac cctgttttac gtatgtccat ctgcccttcc gaggacgacc    2280
agtaacctta ccatcatgct taattgatat taataatcaa tgggccattc taggccgaga    2340
tgtcctccag caatgccaaa gttccctta ccttgcagac caaccctctc gcgttctacc    2400
aatccagaca cctagtgtca ttgggctgga acatctcccc ccgccccag aagttccaca    2460 atttccgtta aaccagagcg cctccaggcc ttgactgacc tggtatccaa ggcgctggag    2520
gccaaataca tagaacctta tcaaggacca ggcaataatc caattttccc ggtcaaaaaa    2580
ccgaatggaa aatggcgctt catccatgat ctccgggcca ccaactgcct cactaaaacc    2640
ctaacttccc cgtctcccgg cccccccgac cttaccagtc tgcccaagg cctcccacat     2700 cttcgaacca ttgacctgac tgacgccttt tttcaaatcc cactgcctgt tgccttccag    2760
ccctattttg catttaccct ccctcagccc aacaaccatg gccccggggc tcggtattcc    2820
tggaaagtac taccccaagg gtttaaaaat agcccaactc tatttgaaca caactctct    2880 catatactca cacctgtaag acaggccttt ccaaaatcta tagtcattca gtacatggat    2940
gacatactct tggccagccc taccccttgaa gagtccatcg ttctcgccca ggaaataacc    3000
aatgctctag cccaggaggg cttgcccatg tccacagaaa aaacccaatc cactcctggt    3060
cccatacact ttctcggaca aaccatatcc aaaaaataca taacttatga aacccctcct    3120
accatacatg tcaagcctaa ttggaccta acagaattac agtccacctt aggggaattg    3180
caatgggtat ccaaagggac tcctacactc cgctcatccc tccatcaatt atatacggcc    3240
ctccgaggtc atcatgaccc ccgcgatacc atacaactta ccccaccaca actacaagcg    3300
ctcaacacgc ttcaaaaggc tctgacccac aattgcagaa gcagaatagt cagtaatctg    3360
cctatcctgg ccctcataat gctccgcccc acaggcacta cagcagttct ttttcaaaca    3420
aaacaaaagt ggccacttgt ctggctgcac acccccacc cggccactag tctgcgcctt    3480
tggggacaat tattggccaa tgccatcatt actctagata agtactcact acaacactat    3540
ggccaggtat gcaaatcctt tcatcataac atatctaatc aggcccttac ccactaccta    3600
cacacgtcag accagtcaag tgttgccatt ctcctacagc actcgcatag gttccataat    3660
ctcggggccc aaccatcggg accatggaaa ggcctcctac aagtaccca aatcttccaa    3720 aatgttgcca cacttagccc tccattcact atttcacctg tggttatcaa ccacgcccct    3780 tgcctcttt ccgatggatc caactctcag gctgccttca ctatctggga taaaaaata    3840 attccaccaac aagtccttcc tcttcctacc gccagctcgg ctcaagcagg ggaactttt    3900 gccctattag cggccctacg agaatgcaaa ccctggtcat cactaaacat attcttagac    3960
tcaaagtttc ttgttggcca gctccggcgc ctggcccttg gggctttcat aggtccatcc    4020
acccaatgtg acttacactc gcaactcctg ccgctcttgt ataacaaaac catttatgtt    4080
catcatgtaa gaagccacac cttattacag gaccctatat cccgcctcaa tgaggctacc    4140
gatgccctca tgctcgcacc ccttctgccc ctcagtccag cgacccttca tgaaatcacc    4200
cactgcaacc cccctgcact gtgcaaccat ggggctacag caactgagac taaggctatt    4260
gtccgggcat gtcacacctg taagataacc aatccccaag ggagactgcc ccagggtcac    4320
```

```
attcgcagag ggcacgcccc aaacactatc tggcaaggag atgtcactca cctacaatac    4380
aaaaaatata aatactgcct tttagtctgg gtcgatactt actcaggagc agtagctgtg    4440
tcgtgccggc gtaaagaaac cagctcagaa tgtgtggcct cgctgctagc agccatttcc    4500
atcctaggaa aaccacacac cattaataca gacaatgggg cagcatattt gtcccaggaa    4560
ttccaacaat tttgtacctc actctccata aaacacacca ctcatgtccc ctacaatccc    4620
accagttccg gattagtgga aagaactaat ggaatcctaa aaaccttaat ctccaaatac    4680
ctcctagatg accaccactt gcccctggac acagccattt ccaaaacttt gtggaccata    4740
aaccatctca atgtcctctc ttcctgccaa aagacacgat ggcagttaca tcaagctcaa    4800
cccctgcccc ccgttcctga aatttgccc cttcctgaac cagtgccaaa atggtattat    4860
tataaaatcc caggtcttac cagttcaagg tggagtgggc ctgtacaatc tgttaaagaa    4920
gcagccggag cggccctcat cccggtaggt actaggcaca tctggattcc gtggcgtctc    4980
ctgaaacgag gtgcatgccc aagacccgga gacagcgtaa ccaccgaatc aaaacacaaa    5040
gaccttcaac tccatgggta agtctagtct ctttatttgc ctcttttgct catacatggc    5100
tagtctcttt gtccctggcg accccagtcg gtgcacactt tttataggag cctcctccta    5160
ccactccagt ccctgcgggt ctaactaccc tcaatgtact tggacactcg acctagtgtc    5220
acttaccagg gatcaaagtc taaaccctcc atgcccagat ctagtcacct actcccagta    5280
tcacagacct tattccttgt atcttttcc ccattggatt actaaaccga atcgtcaagg    5340
ccttggttat tactctgcct cctactcaga tccctgtgct atcaagtgcc cctacctagg    5400
atgtcaatct tggacatgtc cctatacagg acctatgtcc agcccatact ggaagtacac    5460
ctcagaccta aatttcaccc aaaaggtgtc tctgtcacc ctccatctac atttctcaaa    5520
atgcggatcc tccttctctc ttttactcga cgcacccggt tatgaccccg tatggttcct    5580
ttcctcccaa actacacagg ccccacctac cccgcccct ctgacacaag actccgactt    5640
ccaacatatc ttggagccct ctgtgccctg gagctccaaa atcctcaacc ttatcctctt    5700
aactcttaaa agcactaact actcctgcat ggtttgcgtt gaccgctcca gcctctcctc    5760
atggcatgtc ttgtatgacc cactaaaagt tcccaagcaa cacgaacccc gtgcccgggc    5820
cctcttgcgg ccctctctgg ccattccaat aactaatacc acaccccct ttccttggtc    5880 ccattgctac tgcccccttc tacaggctgt catctccaat aactgcaaca actcagttat    5940
actgcccccc ttctctctgt ccctgtcct cgatctctcc aagcctcgtc agcgccgagc    6000
cgtccccatc gccgtttggc tggtgtccgc cctagcggtc ggtacaggta tagccggcgg    6060
caccaccggg tccctatcct tggcatccag caggagcctg ctacatgaag tagaccaaga    6120
tataagccat ctcactcaag ccatagttaa gaaccataac aatatccttc gggttgctca    6180
atacgctgca caaaaccgac gaggcctaga tttactcttc tgggaacaag gaggtctatg    6240
caaggctatc agggaacaat gttgtttct caatatcagc aatacccacg tgtctgtgct    6300
ccaagagaga cccccttag aaaaaagggt gattaccggt tggggactca attgggacct    6360
cggcctatcc caatgggccc gtgaagccct ccagaccggt attaccctgt tagccctctt    6420
cctcctactt atcatggtag gcccttgtgt cctgcgccag ctacaggccc tcctgttccg    6480
cctacagcac cgtagccacc catactccct cctcaatcgc gaaaccaacc tataacacct    6540
ctgcaacctc ctgtagcaat gagccatagt cctcgcccct accagaaacc cacatacagc    6600
ataggcccga agaatctccc caaatatcca tgccttgact ccagtaatcc atgtacccaa    6660
agtattcccc taatgcctcc tcacaatcca cgcgaagttg gaaattctct cgttccaaaa    6720
```

```
agtctatata  accegtcaac  aaattgcaaa  acccctcaaa  ccccagtaag  tctatacaat   6780
ccaactgctg  ccgccgctcc  ttttttctcc  tctttctctc  ctcttttccc  tcgtgacacc   6840
tcctccggcg  ctcttctctt  cttttccgac  ccgccagta   gcttagcaat  tgcttctgct   6900
cctgagcaag  gtcttctaag  cgacccttcc  aatatcctga  atcctttgta  ctagatccca   6960
gaggacgccc  tcgggtcgc   ctaccacccc  ctgcagcat   gtccacttga  tcttttcccg   7020
attgatcaca  caactccaat  aaagcttcca  ccggtgtgag  aggatcttcg  gccgccagta   7080
tcggtggtcc  cacactccta  gaccgagagg  tcaagctgcc  cccggaagta  gagacgcagg   7140
aatacaccac  aggcatagtc  cccgcagttg  tggtctctgg  agtcagtaaa  ggcatcttcc   7200
taaaatacccc tgtaaaataa  tctcctgtca  gcccactttc  caggtttcgg  gcagagcctg   7260
ctctacgggt  accctgtcta  cgttttcggc  gattgtgtgc  aggccgattg  gtgccccatt   7320
tccggggggc  tttgttccgc  ccggctacat  cggcacgcct  tactggccac  ctgtcctgaa   7380
caccagatca  cctgggaccc  catcgatgga  cgcgttgtca  gctcgcctct  acaataccttt  7440
atccctcgcc  tccctcctt   ccccacccaa  agaacttccc  gcaccctcaa  ggtcctcacc   7500
ccgccgccca  ctgctacaac  ccccaaagtt  cctccctcct  tcttccatgc  agtcaggaaa   7560
cacacccctt  tccgaaacaa  ctgcctcgag  ctcaccttgg  gagagcaact  accegccatg   7620
tcttttcccg  accccggcct  ccgacccaa   aatgtctata  ccatgtgggg  aagcaccatc   7680
gtgtgcttat  acctctacca  actcacacct  ccaatgacct  ggccgttaat  cccacatgtc   7740
attttttgcc  atccggacca  actagggcc   ttcctaacaa  aaatccctac  caaacgcttg   7800
gaagaactct  tatacaaact  attcttaagt  acaggggcca  tacttatcct  acctgaaaat   7860
tgcttcccaa  ctaccctgtt  tcagcccacc  cgcgcaccag  taattcaagc  ccctggcac    7920
tcaggcctac  tcccatacct  aaaggaaatt  gtcaccccg   ggctgatttg  ggtgtttact   7980
gacggtagtt  ctatgatttc  cggaccctgc  cccaaggaag  ggcagccatc  tttggtggtc   8040
caatcatcta  cattcatttt  ccaaaaattt  caaaccaaag  cctatcaccc  agccttcctc   8100
ctgtcccata  aattaatcca  atactcctcg  ttccattccc  tccatctact  ttttgaagaa   8160
tacaccactg  tccccttttc  tttattgttt  aacgaaaaag  aggcaaatga  cagtgacagc   8220
aagcccaag   gcgagccaca  actactagcc  aaagggcata  cagttgaatc  atctgtctag   8280
gggacgtctc  gcacccagag  tatgtccaaa  gaacaccagg  gctctgacgt  ctctccctgc   8340
cttgtctccc  ggaaaaaacc  ttaaaccacc  catttcctca  tgtttgccca  aggctctgac   8400
gataaccctg  aaaaatttga  ctaacaaata  aaggaacctg  acccctataa  aaggggagag   8460
cgacctaaaa  atgggatcaa  ccttttctcc  ccaacgccct  ttcgcgcccc  gcggacagcc   8520
actgtccggg  ctactcctgg  cctacctaga  tcattgctcc  gcgcccgagc  cattcttctg   8580
cagccaagcg  gcaccttgca  ccttcgcttc  tcctgtcctg  gtaagatccc  actgggtaga   8640
gctaggccgt  tactccctgg  ccgctcccct  ggagctcctt  tgcttagctc  ttaaggtcgc   8700
tctctccttc  tcgttagggt  ccaaggacta  actttacttc  cgtgtctcgg  tctcctttct   8760
ttggcggtct  cgtctaaagt  cgaaagtaac  acctcaaact  gtcagcagcg  aggcctggcc   8820
cggggccagc  gcctgtgagc  tttactcggc  tcggagccag  gggctcagaa  agtaaaggct   8880
gtagctgcca  gcctttgagg  ggaaccaaaa  aca                                   8913
```

<210> SEQ ID NO 2
<211> LENGTH: 20
<212> TYPE: DNA
<213> ORGANISM: Artificial sequence

```
<220> FEATURE:
<223> OTHER INFORMATION: Theoretical nucleic acid molecule illustrating
      percent sequence identity.

<400> SEQUENCE: 2
atggtggacc cggtgggctt                                              20

<210> SEQ ID NO 3
<211> LENGTH: 20
<212> TYPE: DNA
<213> ORGANISM: Artificial sequence
<220> FEATURE:
<223> OTHER INFORMATION: Theoretical nucleic acid molecule illustrating
      percent sequence identity.

<400> SEQUENCE: 3 acggggatc cggcgggcct                                               20

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 4
gtaccctgtc tacgttttcg gcgat                                        25

<210> SEQ ID NO 5
<211> LENGTH: 26
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 5
gangantgna ntacnaaaga tggctg                                       26

<210> SEQ ID NO 6
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 6
ttactggcca cctgtcctga acac                                         24

<210> SEQ ID NO 7
<211> LENGTH: 23
```

```
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 7
ttngggnang gnccggaaat cat                                          23

<210> SEQ ID NO 8
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 8
catccggacc aactagggc cttc                                          24

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 9
cagcccaccc gcgcaccagt aatt                                         24

<210> SEQ ID NO 10
<211> LENGTH: 27
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(16)
<223> OTHER INFORMATION: n is a, c, g, or t

<400> SEQUENCE: 10
tcctgaacng tcnnnncgct tttatag                                      27

<210> SEQ ID NO 11
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 11
aacaaaaatc cctaccaaac gctt                                         24
```

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 12
ctctgacgtc tctccctgcc ttgt                                            24

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 13
atcccggacg agccccca                                                   18

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 14
ccggaaaaaa ccttaaacca ccca                                            24

<210> SEQ ID NO 15
<211> LENGTH: 493
<212> TYPE: PRT
<213> ORGANISM: STLV-3 subtype D

<400> SEQUENCE: 15

```
Met Gly Lys Ser Ser Leu Phe Ile Cys Leu Phe Cys Ser Tyr Met Ala
1               5                   10                  15

Ser Leu Phe Val Pro Gly Asp Pro Ser Arg Cys Thr Leu Phe Ile Gly
            20                  25                  30

Ala Ser Ser Tyr His Ser Ser Pro Cys Gly Ser Asn Tyr Pro Gln Cys
        35                  40                  45

Thr Trp Thr Leu Asp Leu Val Ser Leu Thr Arg Asp Gln Ser Leu Asn
    50                  55                  60

Pro Pro Cys Pro Asp Leu Val Thr Tyr Ser Gln Tyr His Arg Pro Tyr
65                  70                  75                  80

Ser Leu Tyr Leu Phe Pro His Trp Ile Thr Lys Pro Asn Arg Gln Gly
                85                  90                  95

Leu Gly Tyr Tyr Ser Ala Ser Tyr Ser Asp Pro Cys Ala Ile Lys Cys
            100                 105                 110

Pro Tyr Leu Gly Cys Gln Ser Trp Thr Cys Pro Tyr Thr Gly Pro Met
        115                 120                 125

Ser Ser Pro Tyr Trp Lys Tyr Thr Ser Asp Leu Asn Phe Thr Gln Lys
    130                 135                 140

Val Ser Ser Val Thr Leu His Leu His Phe Ser Lys Cys Gly Ser Ser
145                 150                 155                 160

Phe Ser Leu Leu Leu Asp Ala Pro Gly Tyr Asp Pro Val Trp Phe Leu
                165                 170                 175

Ser Ser Gln Thr Thr Gln Ala Pro Pro Thr Pro Ala Pro Leu Thr Gln
            180                 185                 190
```

Asp Ser Asp Phe Gln His Ile Leu Glu Pro Ser Val Pro Trp Ser Ser
            195                 200                 205

Lys Ile Leu Asn Leu Ile Leu Leu Thr Leu Lys Ser Thr Asn Tyr Ser
            210                 215                 220

Cys Met Val Cys Val Asp Arg Ser Ser Leu Ser Ser Trp His Val Leu
225                 230                 235                 240

Tyr Asp Pro Leu Lys Val Pro Lys Gln His Glu Pro Arg Ala Arg Ala
            245                 250                 255

Leu Leu Arg Pro Ser Leu Ala Ile Pro Ile Thr Asn Thr Thr Pro Pro
            260                 265                 270

Phe Pro Trp Ser His Cys Tyr Cys Pro Leu Leu Gln Ala Val Ile Ser
            275                 280                 285

Asn Asn Cys Asn Asn Ser Val Ile Leu Pro Pro Phe Ser Leu Ser Pro
            290                 295                 300

Val Leu Asp Leu Ser Lys Pro Arg Gln Arg Arg Ala Val Pro Ile Ala
305                 310                 315                 320

Val Trp Leu Val Ser Ala Leu Ala Val Gly Thr Gly Ile Ala Gly Gly
            325                 330                 335

Thr Thr Gly Ser Leu Ser Leu Ala Ser Ser Arg Ser Leu Leu His Glu
            340                 345                 350

Val Asp Gln Asp Ile Ser His Leu Thr Gln Ala Ile Val Lys Asn His
            355                 360                 365

Asn Asn Ile Leu Arg Val Ala Gln Tyr Ala Ala Gln Asn Arg Arg Gly
            370                 375                 380

Leu Asp Leu Leu Phe Trp Glu Gln Gly Gly Leu Cys Lys Ala Ile Arg
385                 390                 395                 400

Glu Gln Cys Cys Phe Leu Asn Ile Ser Asn Thr His Val Ser Val Leu
            405                 410                 415

Gln Glu Arg Pro Pro Leu Glu Lys Arg Val Ile Thr Gly Trp Gly Leu
            420                 425                 430

Asn Trp Asp Leu Gly Leu Ser Gln Trp Ala Arg Glu Ala Leu Gln Thr
            435                 440                 445

Gly Ile Thr Leu Leu Ala Leu Phe Leu Leu Leu Ile Met Val Gly Pro
            450                 455                 460

Cys Val Leu Arg Gln Leu Gln Ala Leu Leu Phe Arg Leu Gln His Arg
465                 470                 475                 480

Ser His Pro Tyr Ser Leu Leu Asn Arg Glu Thr Asn Leu
            485                 490

<210> SEQ ID NO 16
<211> LENGTH: 420
<212> TYPE: PRT
<213> ORGANISM: STLV-3 subtype D

<400> SEQUENCE: 16

Met Gly Asn Ser Tyr Ser Arg Ala Ala Asn Pro Ile Pro Lys Ala Pro
1               5                   10                  15

Lys Gly Leu Ala Ile His His Trp Leu Asn Phe Leu Gln Ala Ala Tyr
            20                  25                  30

Arg Leu Gln Pro Gly Pro Ser Glu Phe Asp Phe His Gln Leu Arg Asn
            35                  40                  45

Phe Leu Lys Leu Ala Ile Lys Thr Pro Val Trp Leu Asn Pro Ile Asn
        50                  55                  60

Tyr Ser Val Leu Ala Glu Leu Val Pro Lys Asn Tyr Pro Gly Arg Ile
65              70                  75                  80

Gln Glu Ile Ile Ala Ile Leu Ile Gln Glu Thr Ser Thr Gln Glu Val
85 90 95

Pro Pro Ser Ala Pro Pro Ala Ser Glu Pro Gln Asn Pro Pro Pro Tyr
100 105 110

Pro Glu Pro Gly Gln Ala Ile Pro Gln Cys Leu Pro Val Leu His Pro
115 120 125

His Gly Ala Pro Ala Ala His Arg Pro Trp Gln Met Lys Asp Leu Gln
130 135 140

Ala Ile Lys Gln Glu Val Thr Ser Ser Ala Pro Gly Ser Pro Gln Phe
145 150 155 160

Met Gln Thr Val Arg Leu Ala Val Gln Gln Phe Asp Pro Thr Ala Lys
165 170 175

Asp Leu His Asp Leu Leu Gln Tyr Leu Cys Ser Ser Leu Val Ala Ser
180 185 190

Leu His His Gln Gln Leu Glu Thr Leu Ile Ala Gln Ala Glu Thr Gln
195 200 205

Gly Ile Thr Gly Tyr Asn Pro Leu Ala Gly Pro Leu Arg Val Gln Ala
210 215 220

Asn Asn Pro Thr Gln Gln Gly Leu Arg Arg Glu Tyr Gln Asn Leu Trp
225 230 235 240

Leu Ser Ala Phe Ser Ala Leu Pro Gly Asn Thr Lys Asp Pro Thr Trp
245 250 255

Ala Ala Ile Leu Gln Gly Pro Glu Glu Pro Phe Cys Thr Phe Val Glu
260 265 270

Arg Leu Asn Val Ala Leu Asp Asn Gly Leu Pro Glu Gly Thr Pro Lys
275 280 285

Glu Pro Ile Leu Arg Ser Leu Ala Tyr Ser Asn Ala Asn Lys Glu Cys
290 295 300

Gln Lys Leu Leu Gln Ala Arg Gly Gln Thr Asn Gly Pro Leu Gly Asp
305 310 315 320

Met Leu Arg Ala Cys Gln Ala Trp Thr Pro Arg Asp Lys Asn Lys Val
325 330 335

Leu Met Val Gln Pro Lys Lys Thr Pro Pro Pro Asn Gln Pro Cys Phe
340 345 350

Arg Cys Gly Gln Ala Gly His Trp Ser Arg Asp Cys Lys Gln Pro Arg
355 360 365

Pro Pro Pro Gly Pro Cys Pro Leu Cys Gln Asp Pro Thr His Trp Lys
370 375 380

Arg Asp Cys Pro Gln Leu Lys Pro Asp Pro Glu Glu Gly Met Leu Leu
385 390 395 400

Asp Leu Pro Cys Glu Asp Pro Ala Ala Arg Asp Gln Lys Asn Phe Ile
405 410 415

Gly Gly Glu Asp
420

<210> SEQ ID NO 17
<211> LENGTH: 176
<212> TYPE: PRT
<213> ORGANISM: STLV-3 subtype D

<400> SEQUENCE: 17

Pro Ser Gly Gln Arg Pro Lys Lys Leu His Arg Gly Gly Gly Leu Ala
1 5 10 15

Ser Pro Gln Thr Val Leu Pro Phe Ile Pro Leu Ser Gln Gln Lys Gln
20 25 30

Pro Val Leu His Val Arg Val Ser Phe Pro Gly Thr Pro Pro Val Ser
35 40 45

Ile Gln Ala Leu Leu Asp Thr Gly Ala Asp Val Thr Val Leu Pro Ala
50 55 60

Arg Leu Cys Pro Pro Asp Leu Lys Leu Gln Asp Thr Thr Val Leu Gly
65 70 75 80

Ala Ser Gly Pro Ser Thr Asp Lys Phe Lys Val Leu Pro Cys Phe Thr
85 90 95

Tyr Val His Leu Pro Phe Arg Gly Arg Pro Val Thr Leu Pro Ser Cys
100 105 110

Leu Ile Asp Ile Asn Asn Gln Trp Ala Ile Leu Gly Arg Asp Val Leu
115 120 125

Gln Gln Cys Gln Ser Ser Leu Tyr Leu Ala Asp Gln Pro Ser Arg Val
130 135 140

Leu Pro Ile Gln Thr Pro Ser Val Ile Gly Leu Glu His Leu Pro Pro
145 150 155 160

Pro Pro Glu Val Pro Gln Phe Pro Leu Asn Gln Ser Ala Ser Arg Pro
165 170 175

<210> SEQ ID NO 18
<211> LENGTH: 880
<212> TYPE: PRT
<213> ORGANISM: STLV-3 subtype D

<400> SEQUENCE: 18

His Trp Ala Gly Thr Ser Pro Pro Ala Pro Arg Ser Ser Thr Ile Ser
1 5 10 15

Val Lys Pro Glu Arg Leu Gln Ala Leu Thr Asp Leu Val Ser Lys Ala
20 25 30

Leu Glu Ala Lys Tyr Ile Glu Pro Tyr Gln Gly Pro Gly Asn Asn Pro
35 40 45

Ile Phe Pro Val Lys Lys Pro Asn Gly Lys Trp Arg Phe Ile His Asp
50 55 60

Leu Arg Ala Thr Asn Cys Leu Thr Lys Thr Leu Thr Ser Pro Ser Pro
65 70 75 80

Gly Pro Pro Asp Leu Thr Ser Leu Pro Gln Gly Leu Pro His Leu Arg
85 90 95

Thr Ile Asp Leu Thr Asp Ala Phe Phe Gln Ile Pro Leu Pro Val Ala
100 105 110

Phe Gln Pro Tyr Phe Ala Phe Thr Leu Pro Gln Pro Asn Asn His Gly
115 120 125

Pro Gly Ala Arg Tyr Ser Trp Lys Val Leu Pro Gln Gly Phe Lys Asn
130 135 140

Ser Pro Thr Leu Phe Glu Gln Gln Leu Ser His Ile Leu Thr Pro Val
145 150 155 160

Arg Gln Ala Phe Pro Lys Ser Ile Val Ile Gln Tyr Met Asp Asp Ile
165 170 175

Leu Leu Ala Ser Pro Thr Leu Glu Glu Ser Ile Val Leu Ala Gln Glu
180 185 190

Ile Thr Asn Ala Leu Ala Gln Glu Gly Leu Pro Met Ser Thr Glu Lys
195 200 205

Thr Gln Ser Thr Pro Gly Pro Ile His Phe Leu Gly Gln Thr Ile Ser
210 215 220

Lys Lys Tyr Ile Thr Tyr Glu Thr Leu Pro Thr Ile His Val Lys Pro
225 230 235 240

```
Asn Trp Thr Leu Thr Glu Leu Gln Ser Thr Leu Gly Glu Leu Gln Trp
                245                 250                 255

Val Ser Lys Gly Thr Pro Thr Leu Arg Ser Ser Leu His Gln Leu Tyr
            260                 265                 270

Thr Ala Leu Arg Gly His His Asp Pro Arg Asp Thr Ile Gln Leu Thr
        275                 280                 285

Pro Pro Gln Leu Gln Ala Leu Asn Thr Leu Gln Lys Ala Leu Thr His
290                 295                 300

Asn Cys Arg Ser Arg Ile Val Ser Asn Leu Pro Ile Leu Ala Leu Ile
305                 310                 315                 320

Met Leu Arg Pro Thr Gly Thr Thr Ala Val Leu Phe Gln Thr Lys Gln
                325                 330                 335

Lys Trp Pro Leu Val Trp Leu His Thr Pro His Pro Ala Thr Ser Leu
            340                 345                 350

Arg Leu Trp Gly Gln Leu Leu Ala Asn Ala Ile Ile Thr Leu Asp Lys
        355                 360                 365

Tyr Ser Leu Gln His Tyr Gly Gln Val Cys Lys Ser Phe His His Asn
    370                 375                 380

Ile Ser Asn Gln Ala Leu Thr His Tyr Leu His Thr Ser Asp Gln Ser
385                 390                 395                 400

Ser Val Ala Ile Leu Leu Gln His Ser His Arg Phe His Asn Leu Gly
                405                 410                 415

Ala Gln Pro Ser Gly Pro Trp Lys Gly Leu Leu Gln Val Pro Gln Ile
            420                 425                 430

Phe Gln Asn Val Ala Thr Leu Ser Pro Pro Phe Thr Ile Ser Pro Val
        435                 440                 445

Val Ile Asn His Ala Pro Cys Leu Phe Ser Asp Gly Ser Asn Ser Gln
    450                 455                 460

Ala Ala Phe Thr Ile Trp Asp Lys Lys Ile Ile His Gln Gln Val Leu
465                 470                 475                 480

Pro Leu Pro Thr Ala Ser Ser Ala Gln Ala Gly Glu Leu Phe Ala Leu
                485                 490                 495

Leu Ala Ala Leu Arg Glu Cys Lys Pro Trp Ser Ser Leu Asn Ile Phe
            500                 505                 510

Leu Asp Ser Lys Phe Leu Val Gly Gln Leu Arg Arg Leu Ala Leu Gly
        515                 520                 525

Ala Phe Ile Gly Pro Ser Thr Gln Cys Asp Leu His Ser Gln Leu Leu
    530                 535                 540

Pro Leu Leu Tyr Asn Lys Thr Ile Tyr Val His His Val Arg Ser His
545                 550                 555                 560

Thr Leu Leu Gln Asp Pro Ile Ser Arg Leu Asn Glu Ala Thr Asp Ala
                565                 570                 575

Leu Met Leu Ala Pro Leu Leu Pro Leu Ser Pro Ala Thr Leu His Glu
            580                 585                 590

Ile Thr His Cys Asn Pro Pro Ala Leu Cys Asn His Gly Ala Thr Ala
        595                 600                 605

Thr Glu Thr Lys Ala Ile Val Arg Ala Cys His Thr Cys Lys Ile Thr
    610                 615                 620

Asn Pro Gln Gly Arg Leu Pro Gln Gly His Ile Arg Arg Gly His Ala
625                 630                 635                 640

Pro Asn Thr Ile Trp Gln Gly Asp Val Thr His Leu Gln Tyr Lys Lys
                645                 650                 655

Tyr Lys Tyr Cys Leu Leu Val Trp Val Asp Thr Tyr Ser Gly Ala Val
```

```
            660                 665                 670

Ala Val Ser Cys Arg Arg Lys Glu Thr Ser Ser Glu Cys Val Ala Ser
        675                 680                 685

Leu Leu Ala Ala Ile Ser Ile Leu Gly Lys Pro His Thr Ile Asn Thr
    690                 695                 700

Asp Asn Gly Ala Ala Tyr Leu Ser Gln Glu Phe Gln Gln Phe Cys Thr
705                 710                 715                 720

Ser Leu Ser Ile Lys His Thr Thr His Val Pro Tyr Asn Pro Thr Ser
                725                 730                 735

Ser Gly Leu Val Glu Arg Thr Asn Gly Ile Leu Lys Thr Leu Ile Ser
            740                 745                 750

Lys Tyr Leu Leu Asp Asp His His Leu Pro Leu Asp Thr Ala Ile Ser
        755                 760                 765

Lys Thr Leu Trp Thr Ile Asn His Leu Asn Val Leu Ser Ser Cys Gln
    770                 775                 780

Lys Thr Arg Trp Gln Leu His Gln Ala Gln Pro Leu Pro Pro Val Pro
785                 790                 795                 800

Glu Asn Leu Pro Leu Pro Glu Pro Val Pro Lys Trp Tyr Tyr Tyr Lys
                805                 810                 815

Ile Pro Gly Leu Thr Ser Ser Arg Trp Ser Gly Pro Val Gln Ser Val
            820                 825                 830

Lys Glu Ala Ala Gly Ala Ala Leu Ile Pro Val Gly Thr Arg His Ile
        835                 840                 845

Trp Ile Pro Trp Arg Leu Leu Lys Arg Gly Ala Cys Pro Arg Pro Gly
    850                 855                 860

Asp Ser Val Thr Thr Glu Ser Lys His Lys Asp Leu Gln Leu His Gly
865                 870                 875                 880
```

<210> SEQ ID NO 19
<211> LENGTH: 182
<212> TYPE: PRT
<213> ORGANISM: STLV-3 subtype D

<400> SEQUENCE: 19

```
Met Pro Lys Thr Arg Arg Gln Arg Asn His Arg Ile Lys Thr Gln Arg
1               5                   10                  15

Pro Ser Thr Pro Trp Pro Thr Phe Gln Val Ser Gly Arg Ala Cys Ser
            20                  25                  30

Thr Gly Thr Leu Ser Thr Phe Ser Ala Ile Val Cys Arg Pro Ile Gly
        35                  40                  45

Ala Pro Phe Pro Gly Gly Phe Val Pro Pro Gly Tyr Ile Gly Thr Pro
    50                  55                  60

Tyr Trp Pro Pro Val Leu Asn Thr Arg Ser Pro Gly Thr Pro Ser Met
65                  70                  75                  80

Asp Ala Leu Ser Ala Arg Leu Tyr Asn Thr Leu Ser Leu Ala Ser Pro
                85                  90                  95

Pro Ser Pro Pro Lys Glu Leu Pro Ala Pro Ser Arg Ser Ser Pro Arg
            100                 105                 110

Arg Pro Leu Leu Gln Pro Pro Lys Phe Leu Pro Pro Ser Ser Met Gln
        115                 120                 125

Ser Gly Asn Thr Pro Leu Ser Glu Thr Thr Ala Ser Ser Ser Pro Trp
    130                 135                 140

Glu Ser Asn Tyr Pro Pro Cys Leu Ser Pro Thr Pro Ala Ser Asp Pro
145                 150                 155                 160

Lys Met Ser Ile Pro Cys Gly Glu Ala Pro Ser Cys Ala Tyr Thr Ser
```

Thr Asn Ser His Leu Gln
        180

<210> SEQ ID NO 20
<211> LENGTH: 350
<212> TYPE: PRT
<213> ORGANISM: STLV-3 subtype D

<400> SEQUENCE: 20

Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Ile Ser
            20                  25                  30

Gly Gly Leu Cys Ser Ala Arg Leu His Arg His Ala Leu Leu Ala Thr
        35                  40                  45

Cys Pro Glu His Gln Ile Thr Trp Asp Pro Ile Asp Gly Arg Val Val
50                  55                  60

Ser Ser Pro Leu Gln Tyr Leu Ile Pro Arg Leu Pro Ser Phe Pro Thr
65                  70                  75                  80

Gln Arg Thr Ser Arg Thr Leu Lys Val Leu Thr Pro Pro Pro Thr Ala
                85                  90                  95

Thr Thr Pro Lys Val Pro Pro Ser Phe Phe His Ala Val Arg Lys His
            100                 105                 110

Thr Pro Phe Arg Asn Asn Cys Leu Glu Leu Thr Leu Gly Glu Gln Leu
        115                 120                 125

Pro Ala Met Ser Phe Pro Asp Pro Gly Leu Arg Pro Gln Asn Val Tyr
    130                 135                 140

Thr Met Trp Gly Ser Thr Ile Val Cys Leu Tyr Leu Tyr Gln Leu Thr
145                 150                 155                 160

Pro Pro Met Thr Trp Pro Leu Ile Pro His Val Ile Phe Cys His Pro
                165                 170                 175

Asp Gln Leu Gly Ala Phe Leu Thr Lys Ile Pro Thr Lys Arg Leu Glu
            180                 185                 190

Glu Leu Leu Tyr Lys Leu Phe Leu Ser Thr Gly Ala Ile Leu Ile Leu
        195                 200                 205

Pro Glu Asn Cys Phe Pro Thr Thr Leu Phe Gln Pro Thr Arg Ala Pro
    210                 215                 220

Val Ile Gln Ala Pro Trp His Ser Gly Leu Leu Pro Tyr Leu Lys Glu
225                 230                 235                 240

Ile Val Thr Pro Gly Leu Ile Trp Val Phe Thr Asp Gly Ser Ser Met
                245                 250                 255

Ile Ser Gly Pro Cys Pro Lys Glu Gly Gln Pro Ser Leu Val Val Gln
            260                 265                 270

Ser Ser Thr Phe Ile Phe Gln Lys Phe Gln Thr Lys Ala Tyr His Pro
        275                 280                 285

Ala Phe Leu Leu Ser His Lys Leu Ile Gln Tyr Ser Ser Phe His Ser
    290                 295                 300

Leu His Leu Leu Phe Glu Glu Tyr Thr Thr Val Pro Phe Ser Leu Leu
305                 310                 315                 320

Phe Asn Glu Lys Glu Ala Asn Asp Ser Asp Ser Lys Pro Gln Gly Glu
                325                 330                 335

Pro Gln Leu Leu Ala Lys Gly His Thr Val Glu Ser Ser Val
            340                 345                 350

```
<210> SEQ ID NO 21
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 21
ccctcaaggt cctcaccccg ccgc                                          24

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 22
taacggccag gtcattggag gtgt                                          24

<210> SEQ ID NO 23
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 23
aagttcctcc ctccttcttc catg                                          24

<210> SEQ ID NO 24
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 24
tggtagaggt ataagcacac gatggtg                                       27

<210> SEQ ID NO 25
<211> LENGTH: 1053
<212> TYPE: DNA
<213> ORGANISM: STLV-3 subtype D

<400> SEQUENCE: 25
atggcccact ttccaggttt cgggcagagc ctgctctacg ggtaccctgt ctacgttttc    60
ggcgattgtg tgcaggccga ttggtgcccc atttccgggg ggctttgttc cgcccggcta   120
catcggcacg ccttactggc cacctgtcct gaacaccaga tcacctggga ccccatcgat   180
ggacgcgttg tcagctcgcc tctacaatac cttatccctc gcctcccctc cttccccacc   240
caaagaactt cccgcaccct caaggtcctc accccgccgc ccactgctac aaccccaaa    300 gttcctccct ccttcttcca tgcagtcagg aaacacaccc ctttccgaaa caactgcctc   360
gagctcacct tgggagagca actacccgcc atgtctttcc ccgacccggg cctccgaccc   420
caaaatgtct ataccatgtg gggaagcacc atcgtgtgct ataccctcta ccaactcaca   480
cctccaatga cctggccgtt aatcccacat gtcatttttt gccatccgga ccaactaggg   540
gccttcctaa caaaaatccc taccaaacgc ttggaagaac tcttatacaa actattctta   600
agtacagggg ccatacttat cctacctgaa aattgcttcc caactaccct gtttcagccc   660
acccgcgcac cagtaattca agcccctgg cactcaggcc tactcccata cctaaaggaa   720
attgtcaccc ccgggctgat ttgggtgttt actgacggta gttctatgat ttccggaccc   780
```

```
tgccccaagg aagggcagcc atctttggtg gtccaatcat ctacattcat tttccaaaaa      840
tttcaaacca aagcctatca cccagccttc ctcctgtccc ataaattaat ccaatactcc      900
tcgttccatt ccctccatct acttttgaa gaatacacca ctgtcccctt ttctttattg      960
tttaacgaaa aagaggcaaa tgacagtgac agcaagcccc aaggcgagcc acaactacta     1020 gccaagggc atacagttga atcatctgtc tag                                    1053

<210> SEQ ID NO 26
<211> LENGTH: 549
<212> TYPE: DNA
<213> ORGANISM: STLV-3 subtype D

<400> SEQUENCE: 26
atgcccaaga cccggagaca gcgtaaccac cgaatcaaaa cacaaagacc ttcaactcca       60
tggcccactt tccaggtttc gggcagagcc tgctctacgg gtaccctgtc tacgttttcg      120
gcgattgtgt gcaggccgat tggtgcccca tttccggggg gctttgttcc gcccggctac      180
atcggcacgc cttactggcc acctgtcctg aacaccagat cacctgggac cccatcgatg      240
gacgcgttgt cagctcgcct ctacaatacc ttatccctcg cctcccctcc ttccccaccc      300
aaagaacttc ccgcaccctc aaggtcctca ccccgccgcc cactgctaca accccaaag      360 ttcctccctc cttcttccat gcagtcagga aacacacccc tttccgaaac aactgcctcg      420
agctcacctt gggagagcaa ctacccgcca tgtctttccc cgaccccggc ctccgacccc      480
aaaatgtcta taccatgtgg ggaagcacca tcgtgtgctt atacctctac caactcacac      540
ctccaatga                                                              549
```

SIMIAN T-CELL LYMPHOTROPIC VIRUS

CROSS REFERENCE TO RELATED APPLICATION

This is the U.S. National Stage of International Application No. PCT/US2008/064270, filed May 20, 2008, which was published in English under PCT Article 21 (2), which in turn claims the benefit of U.S. Provisional Application 60/990,138, filed Nov. 26, 2007, and U.S. Provisional Application No. 60/939,304, filed May 21, 2007, both of which provisional applications are incorporated by reference herein in their entirety.

FIELD

This application relates to a highly divergent simian T-cell lymphotropic virus type 3 subtype, provisionally classified as simian T-cell lymphotropic virus type 3 West African subtype D (STLV-3 subtype D), specifically to the nucleic acid sequences from the virus, open reading frames in this virus, and to amino acid sequences encoded by these sequences.

BACKGROUND

Primate T-cell leukemia viruses (PTLVs) are genetically diverse deltaretroviruses comprised of simian and human T-cell leukemia viruses (STLVs and HTLVs, respectively). Like human immunodeficiency virus (HIV), HTLV is a zoonotic simian retrovirus originating from historical and contemporary contact with STLV-infected nonhuman primates (NHPs). The genetic diversity of HTLV is directly related to the genetic diversity of the STLVs from which the primary zoonotic infection originated, as evidenced by the clustering of geographically proximal HTLVs and STLVs within the same phylogenetic lineages. Four PTLV groups have been identified: PTLV-1, PTLV-2, PTLV-3 and PTLV-4. PTLV-1, PTLV-2 and PTLV-3 include human (HTLV-1, HTLV-2, and HTLV-3) and simian (STLV-1, STLV-2, and STLV-3) viruses. PTLV-4 comprises HTLV-4, which was identified from one individual in Cameroon with known exposure to primates. A simian counterpart of this virus has not yet been identified (Wolfe et al. *Proc. Natl. Acad. Sci. U.S.A.* 102:7994-7999, 2005).

HTLV-1 and HTLV-2 are known to be transmitted through sexual contact (Murphy et al. *Ann. Intern. Med.* 111:555-560, 1989); mother-to-child transmission through breastfeeding (Hino et al. *Jpn. J. Cancer. Res.* 1985, 76:474-480, 1985; Vitek et al. *J. Infect. Dis.* 171:1022-1026, 1995); transfusion of blood and/or blood products (Maims et al. *Int. J. Cancer* 51:886-891, 1992; Okochi and Sato *Princess Takamatsu Symp.* 15:129-135, 1984; Okochi et al. *Vox. Sang.* 46:245-253, 1984); and injection drug use (Van Brussel et al. *Rev. Med. Virol.* 9:155-170, 1999). The mechanisms of transmission of PTLVs and other retroviruses between primates and humans are largely unknown, but it is believed that humans can become infected with simian retroviruses through direct exposure to primates via bites or scratches or contact with body fluids from butchering and handling infected bushmeat (Wolfe et al. *Proc. Natl. Acad. Sci. U.S.A.* 102:7994-7999, 2005; Wolfe et al. *Lancet* 363:932-937, 2004).

Many of the PTLV strains and subtypes have been described from human and primate samples derived from central Africa. In addition to the recent discovery of HTLV-3 (Wolfe et al. *Proc. Natl. Acad. Sci. U.S.A.* 102:7994-7999, 2005; Calattini et al. *Retrovirology* 2:30, 2005) and HTLV-4 (Wolfe et al. *Proc. Natl. Acad. Sci. U.S.A.* 102:7994-7999, 2005) from primate hunters in southern Cameroon, HTLV-1 subtypes B, D and E (Mahieux et al. *J. Virol.* 71:1317-1333, 1997; Salemi et al. *Virology* 246:277-287, 1998) and HTLV-2 subtypes B and D (Vandamme et al. *J. Virol.* 72:4327-4340, 1998) have been isolated from inhabitants of this region. Similarly, STLV-1, found in the HTLV-1 subtype B clade, has been identified in Cameroonian gorillas (*Gorilla gorilla*) and chimpanzees (*Pan troglodytes vellerosus*) (Nerrienet et al. *J. Gen. Virol.* 85:25-29, 2004) and STLV-3 has been found in wild-caught red-capped mangabeys (*Cercocebus torquatus*) from Nigeria and Cameroon (Meertens et al. *J. Gen. Virol.* 84:2723-2727, 2003). Furthermore, evidence for dual infections of STLV-1 and STLV-3 in agile mangabeys (*Cercocebus agilis*) in Cameroon has also been reported (Courgnaud et al. *J. Virol.* 78:4700-4709, 2004). These studies suggest that humans are exposed to a significant number of PTLVs in west and central Africa. Therefore, the need exists for methods of detecting viral infections, for example to monitor the transmission of such viruses into the human population. In addition, the need exists for vaccines for such viruses, for example by producing an immune response to peptides isolated from such viruses. However, it is not possible to vaccinate populations against organisms not known to exist, nor can such unknown organisms be detected and followed in a population at risk of infection.

SUMMARY

Widespread exposure to a broad range of non-human primate body fluids and tissues via hunting and butchering, or keeping primate pets has been implicated in the emergence of three different retrovirus genera: HIV, HTLV, and more recently simian foamy virus (SFV). While very little is known about the public health implications of SFV infection, HIV and HTLV spread globally and became pathogenic following cross-species transmission with enormous social, medical, political, and economic consequences. The recent discovery of HTLV-3 and HTLV-4 in primate hunters from Cameroon doubles the number of known deltaretroviruses in humans. Novel STLV-1-like infections were also identified in primate hunters in this same study. These discoveries demonstrate that the diversity of PTLV is far from being understood and that zoonotic infection of humans with STLV continues to occur in persons exposed to non-human primates. Thus, understanding the diversity, prevalence, and geographic range of STLV infection in areas where frequent contact with wild NHPs is common provides important information about the origin and emergence of HTLV, and the risks of exposure to these and possibly other simian viruses.

As disclosed herein, through analysis of LTR and larger tax sequences from *C. mona* and *C. nictitans*, a divergent STLV-3-like strain forming a unique PTLV-3 clade provisionally designated STLV-3 subtype D has been discovered. Given the propensity of STLV to cross species boundaries, the increased frequency of hunting and demand for primate bushmeat in Africa, and the apparent broad diversity of STLV subtypes in Cameroon it is quite possible that human infection with this unique STLV-3 subtype will or may have already occurred. The discovery of this novel PTLV-3 subtype in two different monkey species and an apparent ancient origin of this lineage suggest a possible wider distribution of this variant. Therefore, the ease with which STLVs can cross species barriers and potentially transmit via primate-hunting practices warrants increased surveillance for human infection with this divergent subtype. Since both HIV and HTLV have arisen through multiple introductions from primates to humans, there is an impetus to expand surveillance for these and other retroviruses in their natural host reservoirs and in persons exposed to non-human primates in order to predict and possibly prevent the next retrovirus pandemic.

The present disclosure relates to a highly divergent simian T-cell lymphotropic virus type 3 subtype, provisionally classified as simian T-cell lymphotropic virus type 3 West African subtype D (referred to herein as STLV-3 subtype D) and isolated nucleic acid molecules from the genome of this virus. In some embodiments, isolated STLV-3 subtype D nucleic acid molecules encoding STLV-3 subtype D polypeptides are provided. In one embodiment, a nucleic acid sequence encoding the STLV-3 subtype D genome is at least 95% identical to the nucleotide sequence according to SEQ ID NO: 1. In several examples, nucleotides encoding s STLV-3 subtype D envelope polypeptides, proteases, polymerases, tax polypeptides, rex polypeptides, and capsid polypeptides and polypeptides expressed from such nucleic acids are disclosed. In one embodiment, a nucleic acid sequence encoding a STLV-3 subtype D envelope polypeptide is disclosed that is at least 95% identical to the nucleotide sequence according to nucleotides 5054-6535 of SEQ ID NO: 1. In another embodiment, a nucleic acid sequence encoding a STLV-3 subtype D capsid polypeptide is disclosed that is at least 95% identical to the nucleotide sequence according to nucleotides 747-2009 of SEQ ID NO: 1. In a further embodiment, a nucleic acid sequence encoding a STLV-3 subtype D protease is disclosed that is at least 95% identical to the nucleotide sequence according to nucleotides 1961-2494 of SEQ ID NO: 1. In a further embodiment, a nucleic acid sequence encoding a STLV-3 subtype D polymerase is disclosed that is at least 95% identical to the nucleotide sequence according to nucleotides 2416-5061 of SEQ ID NO: 1. In a further embodiment, a nucleic acid sequence encoding a STLV-3 subtype D tax polypeptide is disclosed that is at least 95% identical to the nucleotide sequence according to SEQ ID NO: 25. In a further embodiment, a nucleic acid sequence encoding a STLV-3 subtype D rex polypeptide is disclosed that is at least 95% identical to the nucleotide sequence according to SEQ ID NO: 26. In several examples, a nucleic acid sequence encoding a STLV-3 subtype D polypeptide is operably linked to a promoter.

In some embodiments, a nucleic acid sequence encoding a STLV-3 subtype D polypeptide is included in a vector, for example a viral vector, such as a viral vector that can be included in a viral particle. Also disclosed are isolated and/or purified STLV-3 subtype D viruses, such as such viruses having identifying sequences disclosed herein. In some embodiments, a disclosed STLV-3 subtype D virus has a nucleotide sequence at least 95% identical to the nucleotide sequence according to SEQ ID NO: 1.

Isolated STLV-3 subtype D polypeptides are disclosed. In one embodiment, an isolated STLV-3 subtype D capsid polypeptide is disclosed that is encoded by a nucleic acid sequence at least 95% identical to the nucleotide sequence according to nucleotides 747-2009 of SEQ ID NO: 1. In another embodiment, an isolated STLV-3 subtype D protease polypeptide is disclosed that is encoded by a nucleic acid sequence at least 95% identical to the nucleotide sequence according to nucleotides 1961-2494 of SEQ ID NO: 1. In one embodiment, an isolated STLV-3 subtype D polymerase polypeptide is disclosed that is encoded by a nucleic acid sequence at least 95% identical to the nucleotide sequence according to nucleotides 2416-5061 of SEQ ID NO: 1. In another embodiment, an isolated STLV-3 subtype D envelope polypeptide is disclosed that is encoded by a nucleic acid sequence at least 95% identical to the nucleotide sequence according to nucleotides 5054-6535 of SEQ ID NO: 1. In a further embodiment, an isolated STLV-3 subtype D tax polypeptide is disclosed that is encoded by a nucleic acid sequence at least 95% identical to the nucleotide sequence according to SEQ ID NO: 25. In a further embodiment, an isolated STLV-3 subtype D rex polypeptide is disclosed that is encoded by a nucleic acid sequence at least 95% identical to the nucleotide sequence according to SEQ ID NO: 26.

In some embodiments, an isolated STLV-3 subtype D capsid polypeptide is disclosed that is encoded by a nucleic acid sequence at least 95% identical to a nucleotide sequence encoding the amino acid sequence according to SEQ ID NO: 16. In another embodiment, an isolated STLV-3 subtype D protease polypeptide is disclosed that is encoded by a nucleic acid sequence at least 95% identical to a nucleotide sequence encoding the amino acid sequence according to SEQ ID NO: 17. In one embodiment, an isolated STLV-3 subtype D polymerase polypeptide is disclosed that is encoded by a nucleic acid sequence at least 95% identical to a nucleotide sequence encoding the amino acid sequence according to SEQ ID NO: 18. In another embodiment, an isolated STLV-3 subtype D envelope polypeptide is disclosed that is encoded by a nucleic acid sequence at least 95% identical to a nucleotide sequence encoding the amino acid sequence according to SEQ ID NO: 15. In a further embodiment, an isolated STLV-3 subtype D rex polypeptide is disclosed that is encoded by a nucleic acid sequence at least 95% identical to a nucleotide sequence encoding the amino acid sequence according to SEQ ID NO: 19. In a further embodiment, an isolated STLV-3 subtype D tax polypeptide is disclosed that is encoded by a nucleic acid sequence at least 95% identical to a nucleotide sequence encoding the amino acid sequence according to SEQ ID NO: 20. Antibodies that specifically bind isolated STLV-3 subtype D polypeptides are also disclosed. Methods are also disclosed for detecting STLV-3 subtype D. These methods can include detecting a STLV-3 subtype D nucleic acid or polypeptide in the sample. Accordingly, probes, primers, and antibodies for use in detecting STLV-3 subtype D nucleic acids or polypeptides are disclosed.

Methods are disclosed generating an immune response in a subject to a STLV-3 subtype D virus. In several examples, these methods include administering to the subject a therapeutically effective amount, such as a therapeutic composition of an isolated nucleic acid molecule encoding a STLV-3 subtype D polypeptide or an isolated polypeptide encoded by such a nucleic acid molecule. In several embodiments, the methods can be of use for treating or preventing STLV-3 subtype D viral infection in a subject.

The foregoing and other features and advantages will become more apparent from the following detailed description of several embodiments, which proceeds with reference to the accompanying figures.

BRIEF DESCRIPTION OF THE FIGURES

FIG. 7 is a table showing intrasubtype sequence variation among STLV3 subtypes.

SEQUENCE LISTING

Figure 1:
FIG. 1 is a schematic representation of the genomic sequencing strategy of the STLV-3 subtype D genome.

The nucleic and amino acid sequences listed in the accompanying sequence listing are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NO: 1 is an exemplary genomic sequence of STLV-3 subtype D.
SEQ ID NO: 2 is the nucleotide sequence of a theoretical nucleic acid molecule illustrating percent sequence identity.
SEQ ID NO: 3 is the nucleotide sequence of a theoretical nucleic acid molecule illustrating percent sequence identity.
SEQ ID NO: 4 is the nucleotide sequence of PCR primer 8699TF1.
SEQ ID NO: 5 is the nucleotide sequence of PCR primer PGTAXR1.
SEQ ID NO: 6 is the nucleotide sequence of PCR primer 8699TF2.
SEQ ID NO: 7 is the nucleotide sequence of PCR primer PGTAXR2.
SEQ ID NO: 8 is the nucleotide sequence of PCR primer 8699TF6.
SEQ ID NO: 9 is the nucleotide sequence of PCR primer 8699TF8.
SEQ ID NO: 10 is the nucleotide sequence of PCR primer PGTATA1+2R1.
SEQ ID NO: 11 is the nucleotide sequence of PCR primer 8699TF7.
SEQ ID NO: 12 is the nucleotide sequence of PCR primer 8699LF3.
SEQ ID NO: 13 is the nucleotide sequence of PCR primer PGPBSR1n.
SEQ ID NO: 14 is the nucleotide sequence of PCR primer 8699LF4.
SEQ ID NO: 15 is an exemplary amino acid sequence of STLV-3 subtype D envelope polypeptide.
SEQ ID NO: 16 is an exemplary amino acid sequence of STLV-3 subtype D capsid polypeptide (Gag).
SEQ ID NO: 17 is an exemplary amino acid sequence of STLV-3 subtype D protease.
SEQ ID NO: 18 is an exemplary amino acid sequence of STLV-3 subtype D polymerase.
SEQ ID NO: 19 is an exemplary amino acid sequence of STLV-3 subtype D rex polypeptide.
SEQ ID NO: 20 is an exemplary amino acid sequence of STLV-3 subtype D tax polypeptide.
SEQ ID NO: 21 is the nucleotide sequence of PCR primer P5TAXF3.
SEQ ID NO: 22 is the nucleotide sequence of PCR primer P5TAXR3.
SEQ ID NO: 23 is the nucleotide sequence of PCR primer P5TAXF2.
SEQ ID NO: 24 is the nucleotide sequence of PCR primer P5TAXR1.
SEQ ID NO: 25 is the nucleotide sequence of a STLV-3 subtype D tax gene formed from the spice of nucleotides 5054-5057 and 7232-8280 of SEQ ID NO: 1.
SEQ ID NO: 26 is the nucleotide sequence of a STLV-3 subtype D rex gene formed from the spice of nucleotides 4995-5057 and 7232-7717 of SEQ ID NO: 1.

DETAILED DESCRIPTION

I. Abbreviations

CTL Cytotoxic T lymphocyte
DBS Dried blood spots
DNA Deoxyribonucleic acid
HIV Human immunodeficiency virus
HTLV Human T-cell lymphotropic virus, human T-cell leukemia virus or human T-lymphotropic virus LTR Long terminal repeat
NHP Non-human primate
PCR Polymerase chain reaction
PTLV Primate T-cell lymphotropic virus, primate T-cell leukemia virus or primate T-lymphotropic virus
STLV Simian T-cell lymphotropic virus, simian T-cell leukemia virus, or simian T-lymphotropic virus II. Terms Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a probe" means "including a probe" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Adjuvant:
A vehicle used to enhance antigenicity; such as a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides.

Administration:
The introduction of a composition into a subject by a chosen route. For example, if the chosen route is intravenous, the composition is administered by introducing the composition into a vein of the subject.

Amplification:
To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, for example the number of copies of a STLV-3 subtype D nucleic acid, such as a STLV-3 subtype D env nucleic acid or fragment thereof. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Animal:

A living multi-cellular vertebrate or invertebrate organism, a category that includes, for example, mammals and birds. The term mammal includes both human and non-human mammals. The term "primate" includes both human and non-human primates. "Non-human primates" are simian primates such as monkeys, chimpanzees, orangutans, baboons, and macaques. Similarly, the term "subject" includes both human and veterinary subjects, such as non-human primates.

Antibody:

Immunoglobulin molecules and immunologically active portions of immunoglobulin molecules, for instance, molecules that contain an antigen binding site that specifically binds (immunoreacts with) an antigen.

A naturally occurring antibody (for example, IgG, IgM, IgD) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) an Fab fragment consisting of the $V_L$, $V_H$, CL, and CH1 domains; (ii) an Fd fragment consisting of the $V_H$ and CH1 domains; (iii) an Fv fragment consisting of the $V_L$ and $V_H$ domains of a single arm of an antibody, (iv) a dAb fragment (Ward et al., *Nature* 341:544-546, 1989) which consists of a $V_H$ domain; (v) an isolated complementarity determining region (CDR); and (vi) an $F(ab')_2$ fragment, a bivalent fragment comprising two Fab fragments linked by a disulfide bridge at the hinge region.

Immunoglobulins and certain variants thereof are known and many have been prepared in recombinant cell culture (for example, see U.S. Pat. No. 4,745,055; U.S. Pat. No. 4,444,487; WO 88/03565; EP 0256654; EP 0120694; EP 0125023; Faoulkner et al., *Nature* 298:286, 1982; Morrison, *J. Immunol.* 123:793, 1979; Morrison et al., *Ann Rev. Immunol* 2:239, 1984).

Capsid:

An outer shell of a virus, such as a STLV-3 subtype D virus, comprising monomeric subunits of protein, such as capsid monomers. Capsid polypeptides are encoded by a viral gag gene.

Cell:
A plant, animal, insect, bacterial, or fungal cell.

cDNA (Complementary DNA):
A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA, for example an RNA from STLV-3 subtype D, such as an RNA encoding STLV-3 subtype D env.

Complementary:
A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In some examples, a nucleic acid molecule, such as probes and primers specific for STLV-3 subtype D nucleic acid disclosed herein, are complementary to a STLV-3 subtype D nucleic acid molecule or the amplification products of such a nucleic acid molecule.

Detect:
To determine if an agent (such as a signal, particular nucleotide, amino acid, nucleic acid molecule, and/or organism, for example a virus) is present or absent, such as a STLV-3 subtype D virus. In some examples, this can further include quantification. The detection of a STLV-3 subtype D nucleic acid molecule indicates the presence of STLV-3 subtype D virus in the sample.

Degenerate Variant and Conservative Variant:
A polynucleotide encoding a polypeptide or an antibody that includes a sequence that is degenerate as a result of the genetic code. For example, a polynucleotide encoding a STLV-3 subtype D polypeptide, such as a STLV-3 subtype D envelope polypeptide, includes a sequence that is degenerate as a result of the genetic code. There are 20 natural amino acids, most of which are specified by more than one codon. Therefore, all degenerate nucleotide sequences are included as long as the amino acid sequence of the STLV-3 subtype D polypeptide encoded by the nucleotide sequence is unchanged. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Such nucleic acid variations are "silent variations," which are one species of conservative variations. Each nucleic acid sequence herein that encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of ordinary skill will recognize that individual substitutions, deletions or additions which alter, add or delete a single amino acid or a small percentage of amino acids (for instance less than 5%, such as less than 4%, less than 3%, less than 2%, or even less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity.

Emission or Emission Signal:
The light of a particular wavelength generated from a source. In particular examples, an emission signal is emitted from a fluorophore after the fluorophore absorbs light at its excitation wavelengths.

Envelope or Envelope Proteins:
Viral envelopes typically include some viral glycoproteins (envelope proteins). Functionally, viral envelopes, such as STLV-3 subtype D envelopes are used to help viruses enter host cells. Glycoproteins on the surface of the envelope serve to identify and bind to receptor sites on the host's membrane. The viral envelope then fuses with the host cell's membrane, allowing the capsid and viral genome to enter and infect the host cell.

Epitope:
An antigenic determinant. These are particular chemical groups or peptide sequences on a molecule that are antigenic, such that they elicit a specific immune response. An antibody binds a particular antigenic epitope, such as an epitope of a STLV-3 subtype D polypeptide, for example an epitope of a STLV-3 subtype D envelope polypeptide.

Excitation or Excitation Signal:
The light of a particular wavelength necessary and/or sufficient to excite an electron transition to a higher energy level. In particular examples, an excitation is the light of a particular wavelength necessary and/or sufficient to excite a fluorophore to a state such that the fluorophore will emit a different (such as a longer) wavelength of light then the wavelength of light from the excitation signal.

Expression:
Translation of a nucleic acid into a protein, for example the translation of a STLV-3 subtype D mRNA into a protein. This includes the translation of the nucleic acid set forth as nucleotides 747-2009 of SEQ ID NO: 1, 1961-2494 of SEQ ID NO: 1, 2416-5061 of SEQ ID NO: 1, 5054-6535 of SEQ ID NO: 1. 5054-5057 and 7232-8280 of SEQ ID NO: 1, or 4995-5057 and 7232-7717 of SEQ ID NO: 1.

Expression Control Sequences:
Nucleic acid sequences that regulate the expression of a heterologous nucleic acid sequence to which it is operatively linked, for example the expression of a STLV-3 subtype D nucleic acid encoding a protein operably linked to expression control sequences. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Fluorophore:

A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the probes and primers disclosed herein are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N, N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher), than the maximum absorbance wavelength of the donor fluorophore, and have a fluorescence emission maximum at a wavelength ranging from about 400 to 900 nm. Acceptor fluorophores have an excitation spectrum overlapping with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as, Dabcyl, QSY7 (Molecular Probes), QSY33 (Molecular Probes), BLACK HOLE QUENCHERS™ (Glen Research), ECLIPSE™ Dark Quencher (Epoch Biosciences), IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET):

A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius. In another example, energy is transferred via FRET between two different fluorophores such that the acceptor molecule can emit light at its characteristic wavelength, which is always longer than the emission wavelength of the donor molecule.

Host Cells:

Cells in which a vector can be propagated and its nucleic acids expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Hybridization:

The ability of complementary single-stranded DNA or RNA to form a duplex molecule (also referred to as a hybridization complex). Nucleic acid hybridization techniques can be used to form hybridization complexes between a probe or primer and a nucleic acid, such as a STLV-3 subtype D nucleic acid molecule. For example, a probe or primer having some homology to a STLV-3 subtype D nucleic acid molecule will form a hybridization complex with a STLV-3 subtype D nucleic acid molecule (such as any of the nucleic acids set forth as nucleotides 747-2009 of SEQ ID NO: 1, 1961-2494 of SEQ ID NO: 1, 2416-5061 of SEQ ID NO: 1, or 5054-6535 of SEQ ID NO: 1, 5054-5057 of SEQ ID NO: 1, 7232-8280 of SEQ ID NO: 1, 4995-5057 of SEQ ID NO: 1, or 7232-7717 of SEQ ID NO: 1).

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each.

Immune Response:

A response of a cell of the immune system, such as a B cell, T cell, or monocyte, to a stimulus. In one embodiment, the response is specific for a particular antigen (an "antigen-specific response"), such as an antigen from a STLV-3 subtype D virus. In one embodiment, an immune response is a T cell response, such as a CD4+ response or a CD8+ response. In another embodiment, the response is a B cell response, and results in the production of specific antibodies, for example antibodies specific for the antigen, such as a STLV-3 subtype D viral antigen.

Immunogenic Peptide:

A peptide which comprises an allele-specific motif or other sequence, such as an N-terminal repeat, such that the peptide will bind an MHC molecule and induce a cytotoxic T lymphocyte ("CTL") response, or a B cell response (for example antibody production) against the antigen from which the immunogenic peptide is derived.

In one embodiment, immunogenic peptides are identified using sequence motifs or other methods, such as neural net or polynomial determinations known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In some specific non-limiting examples, an immunogenic polypeptide includes a region of STLV-3 subtype D polypeptide, such as a STLV-3 subtype D envelope polypeptide, a STLV-3 subtype D capsid polypeptide, a STLV-3 subtype D polymerase, a STLV-3 subtype D rex polypeptide, a STLV-3 subtype D tax polypeptide, a STLV-3 subtype D protease, or a fragment thereof.

Immunogenic Composition:

A composition comprising an immunogenic peptide that induces a measurable CTL response against virus expressing the immunogenic peptide, or induces a measurable B cell response (such as production of antibodies) against the immunogenic peptide. In one example, an "immunogenic composition" is composition comprising a STLV-3 subtype D polypeptide that induces a measurable CTL or B cell response against virus expressing STLV-3 subtype D polypeptide, such as a STLV-3 subtype D envelope polypeptide, or induces a measurable B cell response (such as production of antibodies) against a STLV-3 subtype D polypeptide, such as a STLV-3 subtype D envelope polypeptide. It further refers to isolated nucleic acids encoding an immunogenic peptide, such as a nucleic acid that can be used to express the STLV-3 subtype D polypeptide, such as a STLV-3 subtype D envelope polypeptide (and thus be used to elicit an immune response against this polypeptide).

For in vitro use, an immunogenic composition may consist of the isolated protein, peptide epitope, or nucleic acid encoding the protein, or peptide epitope. For in vivo use, the immunogenic composition will typically comprise the protein or immunogenic peptide in pharmaceutically acceptable carriers, and/or other agents. Any particular peptide, such as a STLV-3 subtype D polypeptide, such as a STLV-3 subtype D envelope polypeptide, or nucleic acid encoding the polypeptide, can be readily tested for its ability to induce a CTL or B cell response by art-recognized assays. Immunogenic compositions can include adjuvants, which are well known to one of skill in the art.

Immunologically Reactive Conditions:

Includes reference to conditions which allow an antibody raised against a particular STLV-3 subtype D epitope, to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intraorganismal and intracellular environment is normally about pH 7 (such as from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Immunotherapy:

A method of evoking an immune response against on their production of target antigens. Immunotherapy based on cell-mediated immune responses involves generating a cell-mediated response to cells that produce particular antigenic determinants, while immunotherapy based on humoral immune responses involves generating specific antibodies to virus that produce particular antigenic determinants.

Inhibiting or Treating a Disease:

Inhibiting the full development of a disease or condition, for example, in a subject who is at risk for a disease such as T-cell leukemia, STLV-3 subtype D viral infection, or combinations thereof. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic"
treatment is a treatment administered to a subject who does not exhibit signs of a disease or exhibits only early signs for the purpose of decreasing the risk of developing pathology.

Isolated:

An "isolated" biological component (such as a protein or a nucleic acid) has been substantially separated or purified away from other biological components in which the component naturally occurs, such as other chromosomal and extrachromosomal DNA, RNA, and proteins. Nucleic acids or proteins that have been "isolated" include nucleic acids or proteins purified by standard purification methods. The term also embraces nucleic acids or proteins prepared by recombinant expression in a host cell as well as chemically synthesized nucleic acids or proteins. Isolated does not require absolute purity, and can include nucleic acid or protein molecules that are at least 50% isolated, such as at least 75%, 80%, 90%, 95%, 98%, 99%, or even 100% isolated.

Label:

An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part, such as a STLV-3 subtype D specific probe or primer. Labels can also be attached to antibodies. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Nucleic Acid (Molecule or Sequence):

A deoxyribonucleotide or ribonucleotide polymer including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides. In some examples, a nucleic acid is a STLV-3 subtype D nucleic acid, which can include nucleic acids purified from a STLV-3 subtype D as well as the amplification products of such nucleic acids.

Nucleotide:

The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine amongst others.

Examples of modified sugar moieties, which may be used to modify nucleotides at any position on its structure, include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Oligonucleotide:

A linear polynucleotide sequence of up to about 200 nucleotide bases in length, for example a polynucleotide (such as DNA or RNA) which is at least 6 nucleotides, for example at least 15, 25, 50, 100 or even 200 nucleotides long.

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. In some examples disclosed herein, a promoter is operably linked to a STLV-3 subtype D nucleic acid.

ORF:

Open reading frame. Contains a series of nucleotide triplets (codons) coding for amino acids without any termination codons. These sequences are usually translatable into protein.

Pharmaceutical Agent:

A chemical compound or composition capable of inducing a desired therapeutic or prophylactic effect when properly administered to a subject or a cell. "Incubating" includes a sufficient amount of time for a drug to interact with a cell. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

A "therapeutically effective amount" is a quantity of a chemical composition or an anti-viral agent sufficient to achieve a desired effect in a subject being treated. For instance, this can be the amount necessary to inhibit viral replication or to measurably alter outward symptoms of the viral infection. In general, this amount will be sufficient to measurably inhibit virus (for example STLV-3 subtype D) replication or infectivity. When administered to a subject, a dosage will generally be used that will achieve target tissue concentrations that has been shown to achieve in vitro inhibition of viral replication.

Pharmaceutically Acceptable Carriers:

The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide:

Any chain of amino acids, regardless of length or post-translational modification (such as glycosylation or phosphorylation). "Polypeptide" applies to amino acid polymers to naturally occurring amino acid polymers and non-naturally occurring amino acid polymer as well as in which one or more amino acid residue is a non-natural amino acid, for example a artificial chemical mimetic of a corresponding naturally occurring amino acid. In some embodiments, the polypeptide is a STLV-3 subtype D polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used interchangeably herein to refer to a polymer of amino acid residues.

Primer:

A short nucleic acid molecule, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of a STLV-3 subtype D nucleic acid molecule). In some examples, the primers amplify a portion of a STLV-3 subtype D nucleic acid molecule as set forth as nucleotides 747-2009 of SEQ ID NO: 1, 1961-2494 of SEQ ID NO: 1, 2416-5061 of SEQ ID NO: 1, or 5054-6535 of SEQ ID NO: 1, 5054-5057 of SEQ ID NO: 1, 7232-8280 of SEQ ID NO: 1, 4995-5057 of SEQ ID NO: 1, or 7232-7717 of SEQ ID NO: 1, wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of a STLV-3 subtype D nucleic acid molecule) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence (such as the STLV-3 subtype D nucleic acid molecules as set forth as nucleotides 747-2009 of SEQ ID NO: 1, 1961-2494 of SEQ ID NO: 1, 2416-5061 of SEQ ID NO: 1, or 5054-6535 of SEQ ID NO: 1, 5054-5057 of SEQ ID NO: 1, 7232-8280 of SEQ ID NO: 1, 4995-5057 of SEQ ID NO: 1, or 7232-7717 of SEQ ID NO: 1), for example, by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe:

A probe comprises an isolated nucleic acid capable of hybridizing to a target nucleic acid (such as a STLV-3 subtype D nucleic acid molecule). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 20-50 nucleotides, 20-40 nucleotides, or 20-30 nucleotides.

Protease:

A protease is any enzyme that hydrolyses the peptide bonds that link amino acids together in a polypeptide chain. Viral proteases, such as a STLV-3 subtype D protease, hydrolyses the peptide bonds that individual viral polypeptides together.

Polymerizing Agent:

A compound capable of reacting monomer molecules (such as nucleotides) together in a chemical reaction to form linear chains or a three-dimensional network of polymer chains. A particular example of a polymerizing agent is polymerase, an enzyme, which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Quantitating a Nucleic Acid Molecule:

Determining or measuring a quantity (such as a relative quantity) of nucleic acid molecules present, such as the number of amplicons or the number of nucleic acid molecules present in a sample. In particular examples, it is determining the relative amount or actual number of nucleic acid molecules present in a sample, such as STLV-3 subtype D nucleic acid molecules present in a sample.

Recombinant:

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sample:

A sample, such as a biological sample, is a sample obtained from a plant or animal subject. As used herein, biological samples include all clinical samples useful for detection STLV-3 subtype D viral infection in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In particular, embodiments, the biological sample is obtained from a subject, such as in the form of blood.

Sequence Identity/Similarity:

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                       1                      20
    Target Sequence:   atggtggacccggtgggctt   (SEQ ID NO: 2)
                       | ||  ||| |||| ||||  |
    Identified Sequence: acggggatccggcgggcct  (SEQ ID NO: 3)
```

One indication that two nucleic acid molecules are closely related is that the two molecules hybridize to each other under stringent conditions. Stringent conditions are sequence-dependent and are different under different environmental parameters.

Simian T-Cell Lymphotropic Virus (STLV):

Simian single-stranded RNA delataretroviruses known to infect primates. Closely related viruses include Human T-cell lymphotropic virus type (HTLV) and bovine leukemia virus (BLV). Simian and human T cell leukemia virus (STLV and HTLV) are important pathogens causing life-long chronic infections that may lead to T-cell leukemia/lymphoma (ATLL) and a variety of neuromuscular diseases.

Target Nucleic Acid Molecule:

A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA such as STLV-3 subtype D viral RNA, or DNA, such as STLV-3 subtype D viral DNA, for example STLV-3 subtype D viral DNA integrated into a host genome and/or replicated, such as amplified STLV-3 subtype D viral DNA), the amplification and/or detection of which is intended. Purification or isolation of the target nucleic acid molecule, if needed, can be conducted by methods known to those in the art, such as by using a commercially available purification kit or the like. In one example, a target nucleic acid molecule is a STLV-3 subtype D nucleic acid sequence.

Virus:

Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses," such as deltaretroviruses, for example simian T-cell lymphotropic viruses, such as STLV-3 subtype D viruses, are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus.

Virion:

A complete viral particle including envelope, capsid, and nucleic acid elements.

III. Overview of Several Embodiments

Nonhuman primates can be naturally infected with a plethora of viruses with zoonotic potential, including retroviruses. These simian viruses present risks to both captive nonhuman primate populations and persons exposed to nonhuman primates. Simian retroviruses, including simian immunodeficiency virus, simian type D retrovirus, simian T-lymphotropic virus, and gibbon ape leukemia virus, have been shown to cause clinical disease in nonhuman primates. Disclosed herein is the characterization of a new simian T-cell lymphotropic virus (STLV) designated simian T-cell lymphotropic virus type 6 (STLV-3 subtype D) isolated from nonhuman primates in Cameroon. When this virus was originally isolated it was initially given the designation T-cell lymphotropic virus type 5 (STLV-5) or T-cell lymphotropic virus type 6, however the disclosed virus has been provisionally redesignated as simian T-cell lymphotropic virus type 3 West African subtype D (referred to herein as STLV-3 subtype D). Thus, the reference to STLV-5 in U.S. Provisional Application No. 60/939,304, filed May 21, 2007 refers to the STLV-3 subtype D virus disclosed herein. Similarly, the reference to STLV-6 in U.S. Provisional Application No. 60/990,138, filed Nov. 26, 2007 refers to the STLV-3 subtype D virus disclosed herein.

It has been shown that human retrovirus infections with human T-lymphotropic virus and human immunodeficiency virus originated through multiple independent introductions of simian retroviruses into human populations that then spread globally, but little is known about the frequency of such zoonotic events. Thus, monitoring STLV-3 subtype D, for example in non-human primate populations, limits the possibility of this virus making the cross species jump into the human population.

STLV-3 Subtype D Nucleic Acids

This disclosure provides STLV-3 subtype D nucleic acid sequences. In one embodiment, the genomic nucleic acid sequence of STLV-3 subtype D as set forth as SEQ ID NO: 1 is provided. Nucleic acid sequences are also provided that are at least 95% identical, such as at least 96% identical, at least 97% identical, at least 98% identical, or at least 99% identical, to the nucleic acid sequence set forth as SEQ ID NO: 1. An exemplary genomic sequence of STLV-3 subtype D is set forth below as SEQ ID NO: 1:

```
                                             (SEQ ID NO: 1)
tgacagtgacagcaagcccaaggcgagccacaactactagccaaaggg catacagttgaatcatctgtctaggggacgtctcgcacccagagtatgt ccaaagaacaccagggctctgacgtctctccctgccttgtctcccggaa aaaaccttaaaccacccatttcctcatgtttgcccaaggctctgacgat aaccctgaaaaatttgactaacaaataaaggaacctggaccctataaaa ggggagagcgacctaaaaatgggatcaaccttttctccccaacgccctt tcgcgccccgcggacagccactgtccgggctactcctggcctacctaga tcattgctccgcgcccgagccattcttctgcagccaagcggcaccttgc accttcgcttctcctgtcctggtaagatcccactgggtagagctaggcc gttactccctggccgctccctggagctcctttgcttagctcttaaggt cgctctctccttctcgttagggtccaaggactaactttacttccgtgtc tcggtctcctttctttggcggtctcgtctaaagtcgaaagtaacacctc aaactgtcagcagcgaggcctggcccgggccagcgcctgtgagcttta ctcggctcggagccaggggctcagaaagtaaaggctgtagctgccagcc tttgaggggaaccaaaaacaggtggggctcgtccgggattgatcaccc tcctattaaacatgggaaattcatacagccgtgccgccaacccatccc caaggcccaaagggctagcaattcaccactggttaaactttctacaa gctgcctatcggctgcaaccggggccctcagagtttgatttccatcagt tacgaaattttcttaaattagctataaaaaccctgtttggctaaaccc catcaattattccgtcctagctgaactcgttcctaaaaattatccaggc agaatccaagaaattatagccatcctaatccaagaaacctctacgcagg aggttcccccatccgcccaccggccagcgaaccccaaaatccccgcc ttatccagaaccagggcaagccataccccagtgcctacctgttctgcac ccccatggtgccctgccgcccatcgcccttggcagatgaaagatctcc aagctataaaacaggaagttacctcttccgcaccagggagccctcagtt catgcaaaccgtgcgcctggcagtccaacaatttgacccgactgccaaa -continued
gacctccatgacctcttacaatacctgtgctcctcactagttgcctccc tgcaccaccagcagctcgagaccctcatcgctcaggctgaaacccaagg aacccaactcagcaagggctccggcgagaataccaaaacttatggctgt cggccttttctgccctcccaggaaatactaaagaccccacctgggcggc aatcctccagggccccgaggaaccgttttgcacattcgtagaaagactt aatgtggccctagacaacggcctccctgaaggaaccccaaagagccta ttcttcggtccttagcatattctaatgccaacaaagaatgccagaaact cctacaagcccgagggcagacaaacggtcccttaggggacatgctcaga gcttgccaggcgtggacgcccgggacaaaaacaaagtactaatggtcc aacctaaaaagacacctcccccaaatcaaccatgcttccggtgcgggca ggcgggccactggagcagagactgtaaacaacctcgtccccccccaggc ccatgtccgctctgtcaagacccccaccactggaagcgagattgcccgc agctaaaaccagatcctgaagaaggcatgttgttagatctgccttgtga agacccagcgccagagaccaaaaaaacttcataggggggaggactag cctcccccaaacagtgctgccttttataccattatcccagcaaaaca accagtcctacacgtccgagtatccttcccaggtaccccccagtaagc atccaggcgcttttagacacaggggcagatgtaaccgtcctcccagccc gtctatgcccccctgacctaaaattacaagacaccactgtccttggagc cagcgggccaagcaccgacaagtttaaagttctaccctgttttacgtat gtccatctgcccttccgaggacgaccagtaaccttaccatcatgcttaa ttgatattaataatcaatgggccattctaggccgagatgtcctccagca atgccaaagttccctttaccttgcagacccaatccagacaccaaccctc tcgcgttctactagtgtcattgggctggaacatctccccccgccccag aagttccacaatttccgttaaaccagagcgcctccaggccttgactgac ctggtatccaaggcgctgaggccgaaatacatagaaccttatcaaggac caggcaataatccaattttcccggtcaaaaaaccgaatggaaaatggcg cttcatccatgatctccgggccaccaactgcctcactaaaaccctaact tccccgtctcccggccccccgaccttaccagtctgcccaaggcctcc cacatcttcgaaccattgacctgactgacgccttttttcaaatcccact gcctgttgccttccagccctattttgcatttaccctccctcagcccaac aaccatggcccgggctcggtattcctggaaagtactacccccaagggt ttaaaaatagcccaactctatttgaacaacaactctctcatatactcac acctgtaagacaggcctttccaaaatctatagtcattcagtacatggat gacatactcttggccagccctacccttgaagagtccatcgttctcgccc aggaaataaccaatgctctagcccaggagggcttgcccatgtccacaga aaaaacccaatccactcctggtcccatacactttctcggacaaaccata tccaaaaaatacataacttatgaaaccctccctaccatacatgtcaagc ctaattggaccttaacagaattacagtccaccttaggggaattgcaatg ggtatccaaagggactcctacactccgctcatccctccatcaattatat acggccctccgaggtcatcatgaccccgcgataccatacaacttaccc caccacaactacaagcgctcaacacgcttcaaaaggctctgacccacaa
```

```
ttgcagaagcagaatagtcagtaatctgcctatcctggccctcataatg
ctccgccccacaggcactacagcagttcttttcaaacaaaacaaaagt
ggccacttgtctggctgcacaccccaccggccactagtctgcgcct
ttggggacaattattggccaatgccatcattactctagataagtactca
ctacaacactatggccaggtatgcaaatcctttcatcataacatatcta
atcaggcccttaccactacctacacacgtcagaccagtcaagtgttgc
cattctcctacagcactcgcataggttccataatctcggggcccaacca
tcgggaccatggaaaggcctcctacaagtaccccaaatcttccaaaatg
ttgccacacttagccctccattcactattttcacctgtggttatcaacca
cgccccttgcctcttttccgatggatccaactctcaggctgccttcact
atctgggataaaaaataattcaccaacaagtccttcctcttcctaccg
ccagctcggctcaagcaggggaacttttttgccctattagcggccctacg
agaatgcaaaccctggtcatcactaaacatattcttagactcaaagttt
cttgttggccagctccggcgcctggccctttggggctttcataggtccat
ccacccaatgtgacttacactcgcaactcctgccgctcttgtataacaa
aaccatttatgttcatcatgtaagaagccacaccttattacaggaccct
atatcccgcctcaatgaggctaccgatgccctcatgctcgcacccctc
tgcccctcagtccagcgacccttcatgaaatcacccactgcaaccccc
tgcactgtgcaaccatggggctacagcaactgagactaaggctattgtc
cgggcatgtcacacctgtaagataaccaatccccaagggagactgcccc
agggtcacattcgcagagggcacgcccaaacactatctggcaaggaga
tgtcactcacctacaatacaaaaaatataaatactgccttttagtctgg
gtcgatacttactcaggagcagtagctgtgtcgtgccggcgtaaagaaa
ccagctcagaatgtgtggcctcgctgctagcagccatttccatcctagg
aaaaccacacaccattaatacagacaatggggcagcatatttgtcccag
gaattccaacaattttgtacctcactctccataaaacacaccactcatg
tcccctacaatcccaccagttccggattagtggaaagaactaatggaat
cctaaaaaccttaatctccaaatacctcctagatgaccaccacttgccc
ctggacacagccatttccaaaactttgtggaccataaaccatctcaatg
tcctctcttcctgccaaaagacacgatggcagttacatcaagctcaacc
cctgccccgttcctgagaatttgccccttcctgaaccagtgccaaaa
tggtattattataaaatcccaggtcttaccagttcaaggtggagtgggc
ctgtacaatctgttaaagaagcagccggagcggccctcatcccggtagg
tactaggcacatctggattccgtggcgtctcctgaaacgaggtgcatgc
ccaagacccggagacagcgtaaccaccgaatcaaaacacaaagaccttc
aactccatgggtaagtctagtctcttatttgcctcttttgctcataca
tggctagtctctttgtccctggcgaccccagtcggtgcacacttttttat
aggagcctcctcctaccactccagtccctgcgggtctaactaccctcaa
tgtacttggacactcgaccagtgtcacttaccagggatcaaagtctaa
accctccatgcccagatctagtcacctactcccagtatcacagacctta
```

```
ttccttgtatcttttttcccattggattactaaaccgaatcgtcaaggc
cttggttattactctgcctcctactcagatccctgtgctatcaagtgcc
cctacctaggatgtccaatcttggacatgtccctatacaggacctatgt
cagcccatactggaagtacacctcagacctaaatttcacccaaaaggtg
tcctctgtcaccctccatctacatttctcaaaatgcggatctccttctc
ctcttttactcgacgcacccggttatgacccccgtatggttccttcctc
ccaaactacacaggccccacctacacccgcccctctgacacaagactcc
gacttccaacatatcttggagccctctgtgccctggagctccaaaatcc
tcaaccttatcctcttaactcttaaaagcactaactactcctgcatggt
ttgcgttgaccgctccagcctctcctcatggcatgtcttgtatgaccca
ctaaaagttcccaagcaacacgaacccgtgcccgggccctcttgcggc
cctctctggccattccaataactaataccacacccccctttccttggtc
ccattgctactgccccttctacaggctgtcatctccaataactgcaac
aactcagttatactgccccccttctctctgtccctgtcctcgatctct
ccaagcctcgtcagcgccgagccgtccccatcgcgtttggctggtgtc
cgccctagcggtcggtacaggtatagccggcggcaccaccgggtcccta
tccttggcatccagcaggagcctgctacatgaagtagaccaagatataa
gccatctcactcaagccatagttaagaaccataacaatatccttcgggt
tgctcaatacgctgcacaaaaccgacgaggcctagatttactcttctgg
gaacaaggaggtctatgcaaggctatcagggaacaatgttgttttctca
atatcagcaatacccacgtgtctgtgctccaagagagacccccttaga
aaaaagggtgattaccggttggggactcaattgggacctcggcctatcc
caatgggcccgtgaagccctccagaccggtattaccctgttagccctct
tcctcctacttatcatggtaggcccttgtgtcctgcgccagctacaggc
cctcctgttccgcctacagcaccgtagccacccatactccctcctcaat
cgcgaaaccaacctataacacctctgcaacctcctgtagcaatgagcca
tagtcctcgccctaccagaaacccacatacagcataggcccgaagaat
ctccccaaatatccatgccttgactccagtaatccatgtacccaaagta
ttccctaatgcctcctcacaatccacgcgaagttggaaattctctcgt
tccaaaagtctatataacccgtcaacaaattgcaaaaccctca&acc
ccagtaagtctatacaatccaactgctgccgccgctccttttttctcct
ctttctctcctcttttcctcgtgacacctcctccggcgctcttctctt
cttttccgaccccgccagtagcttagcaattgcttctgctcctgagcaa
ggtcttctaagcgacccttccaatatcctgaatcctttgtactagatcc
cagaggacgccctcggggtcgcctaccacccccctgcagcatgtccact
tgatcttttcccgattgatcacacaactccaataaagcttccaccggtg
tgagaggatcttcggccgccagtatcggtggtcccacactcctagaccg
agaggtcaagctgcccccggaagtagagacgcaggaatacaccacaggc
atagtccccgcagttgtggtctctggagtcagtaaaggcatcttcctaa
aatccctgtaaaataatctcctgtcagcccactttccaggtttcgggc
agagcctgctctacgggtaccctgtctacgttttcggcgattgtgtgca
```

-continued

```
ggccgattggtgccccatttccggggggctttgttccgcccggctacat cggcacgccttactggccacctgtcctgaacaccagatcacctgggacc ccatcgatggacgcgttgtcagctcgcctctacaataccttatccctcg cctccctccttccccacccaaagaacttcccgcaccctcaaggtcctc accccgccgcccactgctacaaccccaaagttcctccctccttcttcc atgcagtcaggaaacacaccccttccgaaacaactgcctcgagctcac cttgggagagcaactacccgccatgtctttccccgaccccggcctccga ccccaaaatgtctataccatgtggggaagcaccatcgtgtgcttatacc tctaccaactcacacctccaatgacctggccgttaatcccacatgtcat ttttgccatccggaccaactaggggccttcctaacaaaaatccctacc aaacgcttggaagaactcttatacaaactattcttaagtacaggggcca tacttatcctacctgaaaattgcttcccaactaccctgtttcagcccac ccgcgcaccagtaattcaagcccctggcactcaggcctactcccatac ctaaaggaaattgtcaccccgggctgatttgggtgtttactgacggta gttctatgatttccggaccctgccccaaggaagggcagccatctttggt ggtccaatcatctacattcattttccaaaaatttcaaaccaaagcctat cacccagccttcctcctgtcccataaattaatccaatactcctcgttcc attccctccatctacttttgaagaatacaccactgtccccttttctttt attgtttaacgaaaaagaggcaaatgacagtgacagcaagccccaaggc gagccacaactactagccaaagggcatacagttgaatcatctgtctagg ggacgtctcgcacccagagtatgtccaaagaacaccagggctctgacgt ctctccctgccttgtctcccggaaaaaaccttaaaccacccattcctc atgtttgccaaggctctgacgataaccctgaaaaatttgactaacaaa taaaggaacctggaccctataaaaggggagagcgacctaaaaatgggat caaccttttctccccaacgcccttcgcgcccgcggacagccactgtc cgggctactcctggcctacctagatcattgctccgcgcccgagccattc ttctgcagccaagcggcaccttgcaccttcgcttctcctgtcctggtaa gatcccactgggtagagctaggccgttactccctggccgctcccctgga gctcctttgcttagctcttaaggtcgctctctccttctcgttagggtcc aaggactaactttacttccgtgtctcggtctcctttctttggcggtctc gtctaaagtcgaaagtaaacctcaaactgtcagcagcgaggcctggcc cggggccagcgcctgtgagctttactcggctcggagccaggggctcaga aagtaaaggctgtagctgccagcctttgagggaaccaaaaaca.
```

In several embodiments, the nucleic acid sequences of several STLV-3 subtype D open reading frames (ORFs) are disclosed (see Table 4), such as ORFs for a STLV-3 subtype D capsid polypeptide, a STLV-3 subtype D protease, a STLV-3 subtype D polymerase, a STLV-3 subtype D tax polypeptide, a STLV 5 rex polypeptide, or a STLV-3 subtype D envelope polypeptide. Specific non-limiting examples of STLV-3 subtype D nucleic acid sequences encoding a STLV-3 subtype D polypeptide include, but are not limited, to nucleotides 747-2009 of SEQ ID NO: 1, which encodes a STLV-3 subtype D capsid polypeptide, nucleotides 1961-2494 of SEQ ID NO: 1, which encodes a STLV-3 subtype D protease polypeptide, nucleotides 2416-5061 of SEQ ID NO: 1, which encodes a STLV-3 subtype D polymerase polypeptide, nucleotides 5054-6535 of SEQ ID NO: 1, which encodes a STLV-3 subtype D envelope polypeptide, SEQ ID NO: 25, which encodes a STLV-3 subtype D tax polypeptide, and SEQ ID NO: 26, which encodes a STLV-3 subtype D rex polypeptide.

As shown in FIG. 1, the nucleotide sequence encoding the STLV-3 subtype D tax polypeptide is composed of two portions of non-contiguous nucleic acid sequence that is spliced together to form the entire coding region of the STLV-3 subtype D tax gene, such as a the STLV-3 subtype D tax gene depicted below as SEQ ID NO: 25. The sequence set forth as SEQ ID NO: 25 is composed of nucleotides 5054-5057 of SEQ ID NO: 1 spliced (at the three prime end) to the five prime end of nucleotides 7232-8280 of SEQ ID NO: 1.

An Exemplary STLV-3 Subtype D Tax Gene:

```
                                        (SEQ ID NO: 25)
atggcccactttccaggtttcgggcagagcctgctctacgggtaccctgt ctacgttttcggcgattgtgtgcaggccgattggtgcccatttccgggg ggctttgttccgcccggctacatcggcacgccttactggccacctgtcct gaacaccagatcacctgggacccatcgatggacgcgttgtcagctcgcc tctacaataccttatccctcgcctccctccttccccacccaaagaactt cccgcaccctcaaggtcctcaccccgccgcccactgctacaaccccaaa gttcctccctccttcttccatgcagtcaggaaacacaccccttccgaaa caactgcctcgagctcaccttgggagagcaactacccgccatgtctttcc ccgaccccggcctccgaccccaaaatgtctataccatgtggggaagcacc atcgtgtgcttatacctctaccaactcacacctccaatgacctggccgtt aatcccacatgtcattttgccatccggaccaactaggggccttcctaa caaaaatccctaccaaacgcttggaagaactcttatacaaactattctta agtacaggggccatacttatcctacctgaaaattgcttcccaactaccct gtttcagcccacccgcgcaccagtaattcaagcccctggcactcaggcc tactcccatacctaaaggaaattgtcaccccgggctgatttgggtgttt actgacggtagttctatgatttccggaccctgccccaaggaagggcagcc atctttggtggtccaatcatctacattcattttccaaaaatttcaaacca aagcctatcacccagccttcctcctgtcccataaattaatccaatactcc tcgttccattccctccatctacttttgaagaatacaccactgtcccctt ttctttattgtttaacgaaaaagaggcaaatgacagtgacagcaagcccc aaggcgagccacaactactagccaaagggcatacagttgaatcatctgtc tag
```

As shown in FIG. 1, the nucleotide sequence encoding the STLV-3 subtype D tax polypeptide is composed of two portions of non-contiguous nucleic acid sequence that is spliced together to form the entire coding region of the STLV-3 subtype D rex gene, such as a the STLV-3 subtype D rex gene depicted below as SEQ ID NO: 25. The sequence set forth as SEQ ID NO: 25 nucleotides 4995-5057 of SEQ ID NO: 1 spliced (at the three prime end) to the five prime end of nucleotides to the five prime end of nucleotides 7232-7717 of SEQ ID NO: 1.

An Exemplary STLV-3 Subtype D Rex Gene:

(SEQ ID NO: 26)
atgcccaagacccggagacagcgtaaccaccgaatcaaaacacaaagacc ttcaactccatggcccactttccaggtttcgggcagagcctgctctacgg gtaccctgtctacgttttcggcgattgtgtgcaggccgattggtgccca tttccgggggctttgttccgcccggctacatcggcacgccttactggcc acctgtcctgaacaccagatcacctgggacccatcgatggacgcgttgt cagctcgcctctacaataccttatccctgcctccctccttccccaccc aaagaacttcccgcaccctcaaggtcctcacccgccgcccactgctaca accccaaagttcctccctccttcttccatgcagtcaggaaacacacccc tttccgaaacaactgcctcgagctcaccttgggagagcaactacccgcca tgtctttccccgaccccggcctccgaccccaaaatgtctataccatgtgg ggaagcaccatcgtgtgcttatacctctaccaactcacacctccaatga These polynucleotides include DNA, cDNA, and RNA sequences that encode a STLV-3 subtype D polypeptide. In specific embodiments, these sequences are used for generating oligonucleotide primers and probes for the detection of STLV-3 subtype D in samples, for example probes and primers for the detection of STLV-3 subtype D ORFs, such as ORFs for a STLV-3 subtype D capsid polypeptide, a STLV-3 subtype D protease polypeptide a STLV-3 subtype D polymerase polypeptide, a STLV-3 subtype D tax polypeptide a STLV-3 subtype D rex polypeptide, or a STLV-3 subtype D envelope polypeptide. In other embodiments, these sequences are used for generating polypeptides corresponding to a STLV-3 subtype D capsid polypeptide, a STLV-3 subtype D protease, a STLV-3 subtype D envelope polypeptide, STLV-3 subtype D polymerase, a STLV-3 subtype D tax polypeptide, a STLV-3 subtype D rex polypeptide, or fragments thereof.

All polynucleotides encoding a STLV-3 subtype D polypeptide, such as a STLV-3 subtype D polypeptide fragment, are also included herein. In one embodiment, a STLV-3 subtype D nucleic acid sequence that encodes a polypeptide that functions as a STLV-3 subtype D capsid polypeptide is at least 95% identical, such as at least 96% identical, at least 97% identical, at least 98% identical, at least 99% identical, or even 100% identical to nucleotides 747-2009 of SEQ ID NO: 1. In one embodiment, a STLV-3 subtype D nucleic acid sequence that encodes a polypeptide that functions as a STLV-3 subtype D protease is at least 95% identical, such as at least 96% identical, at least 97% identical, at least 98% identical, at least 99% identical, or even 100% identical to nucleotides 1961-2494 of SEQ ID NO: 1. In one embodiment, a STLV-3 subtype D nucleic acid sequence that encodes a polypeptide that functions as a STLV-3 subtype D envelope polypeptide is at least 95% identical, such as at least 96% identical, at least 97% identical, at least 98% identical, at least 99% identical, or even 100% identical to nucleotides 5054-6535 of SEQ ID NO: 1. In one embodiment, a STLV-3 subtype D nucleic acid sequence that encodes a polypeptide that functions as a STLV-3 subtype D polymerase is at least 95% identical, such as at least 96% identical, at least 97% identical, at least 98% identical, at least 99% identical, or even 100% identical to nucleotides 2416-5061 of SEQ ID NO: 1. In one embodiment, a STLV-3 subtype D nucleic acid sequence that encodes a polypeptide that functions as a STLV-3 subtype D tax polypeptide is at least 95% identical, such as at least 96% identical, at least 97% identical, at least 98% identical, at least 99% identical, or even 100% identical to SEQ ID NO: 25. In one embodiment, a STLV-3 subtype D nucleic acid sequence that encodes a polypeptide that functions as a STLV-3 subtype D rex polypeptide is at least 95% identical, such as at least 96% identical, at least 97% identical, at least 98% identical, at least 99% identical, or even 100% identical to SEQ ID NO: 26.

The polynucleotides of this disclosure include sequences that are degenerate as a result of the genetic code. For example, there are 20 natural amino acids, most of which are specified by more than one codon. Therefore, all degenerate nucleotide sequences are included in the disclosure as long as the amino acid sequence of the STLV-3 subtype D polypeptide encoded by the nucleotide sequence is functionally unchanged.

Also disclosed herein are STLV-3 subtype D oligonucleotides that specifically hybridize to STLV-3 subtype D nucleic acids, such as probes and primers, for example probes and primers that hybridize to the STLV-3 subtype D nucleic acid sequence set for as SEQ ID NO: 1. In some embodiments, the disclosed STLV-3 subtype D oligonucleotides specifically hybridize to a nucleic acid sequence encoding a STLV-3 subtype D capsid polypeptide (for example nucleotides 747-2009 of SEQ ID NO: 1), a nucleic acid sequence encoding a STLV-3 subtype D protease (for example nucleotides 1961-2494 of SEQ ID NO: 1), a nucleic acid sequence encoding a STLV-3 subtype D envelope polypeptide (for example nucleotides 5054-6535 of SEQ ID NO: 1), a nucleic acid sequence encoding a STLV-3 subtype D polymerase (for example nucleotides 2416-5061 of SEQ ID NO: 1), a nucleic acid sequence encoding a STLV-3 subtype D tax polypeptide (for example SEQ ID NO: 25), or a nucleic acid sequence encoding a STLV-3 subtype D rex polypeptide (for example SEQ ID NO: 26), or a nucleic acid sequence encoding a STLV-3 subtype D LTR (for example nucleotides 7-706 of SEQ ID NO: 1). Exemplary primers that specifically hybridize to the nucleic acid sequence set forth as SEQ ID NO: 1 are given in Table 1. The methods disclosed herein take advantage of the fact that under appropriate conditions oligonucleotides, such as probes and primers, form base-paired duplexes with oligonucleotides, which have a complementary base sequence. The stability of the duplex is dependent on a number of factors, including the length of the oligonucleotides, the base composition, and the composition of the solution in which hybridization is effected. The effects of base composition on duplex stability may be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequence(s) and the oligonucleotides, for example amplification primers, real-time PCR primers and probes, or oligonucleotides bound to an array, the rate of formation of mismatched duplexes may be substantially reduced.

The length of each oligonucleotide sequence can be selected to optimize binding of target STLV-3 subtype D nucleic acid sequence, for example a STLV-3 subtype D capsid, protease, rex, tax, polymerase, LTR, or envelope nucleic acid sequence. An optimum length for use with a particular STLV-3 subtype D nucleic acid sequence under specific screening conditions can be determined empirically. Oligonucleotides, for example probes or primers, of the disclosed STLV-3 subtype D nucleic acid sequences may be comprised of at least 15 consecutive nucleic acids, which is sufficient to permit the oligonucleotide to selectively hybridize, for example under conditions of very high stringency, to a STLV-3 subtype D nucleic acid, for example a STLV-3 subtype D nucleic acid that encodes a STLV-3 subtype D capsid polypeptide, protease, polymerase, or envelope polypeptide, or a STLV-3 subtype D nucleic acid sequence that encodes a rex, or tax, polypeptide or even a nucleic acid that encodes a STLV-3 subtype D LTR.

In some embodiments, the disclosed STLV-3 subtype D oligonucleotides specifically hybridize to a nucleic acid sequence encoding a STLV-3 subtype D capsid polypeptide (for example nucleotides 747-2009 of SEQ ID NO: 1), a nucleic acid sequence encoding a STLV-3 subtype D protease (for example nucleotides 1961-2494 of SEQ ID NO: 1), a nucleic acid sequence encoding a STLV-3 subtype D envelope polypeptide (for example nucleotides 5054-6535 of SEQ ID NO: 1), a nucleic acid sequence encoding a STLV-3 subtype D polymerase polypeptide (for example 2416-5061 of SEQ ID NO: 1), a nucleic acid sequence encoding a STLV-3 subtype D tax polypeptide (for example SEQ ID NO: 25), or a nucleic acid sequence encoding a STLV-3 subtype D rex polypeptide (for example SEQ ID NO: 26).

In some embodiments, an oligonucleotide sequence is selected such that it hybridizes under high stringency conditions to a nucleic acid sequence at least 95% identical to, such as at least 96% identical, at least 97% identical, at least 98% identical, at least 99% identical, or even 100% identical to nucleotides 747-2009 of SEQ ID NO: 1. In some embodiments, an oligonucleotide sequence is selected such that it hybridizes under high stringency conditions to a nucleic acid sequence at least 95% identical to, such as at least 96% identical, at least 97% identical, at least 98% identical, at least 99% identical, or even 100% identical to nucleotides 1961-2494 of SEQ ID NO: 1. In some embodiments, an oligonucleotide sequence is selected such that it hybridizes under high stringency conditions to a nucleic acid sequence at least 95% identical to, such as at least 96% identical, at least 97% identical, at least 98% identical, at least 99% identical, or even 100% identical to nucleotides 2416-5061 of SEQ ID NO: 1. In some embodiments, an oligonucleotide sequence is selected such that it hybridizes under high stringency conditions to a nucleic acid sequence at least 95% identical to, such as at least 96% identical, at least 97% identical, at least 98% identical, at least 99% identical, or even 100% identical to nucleotides 5054-6535 of SEQ ID NO: 1. In some embodiments, an oligonucleotide sequence is selected such that it hybridizes under high stringency conditions to a nucleic acid sequence at least 95% identical to, such as at least 96% identical, at least 97% identical, at least 98% identical, at least 99% identical, or even 100% identical to SEQ ID NO: 25. In some embodiments, an oligonucleotide sequence is selected such that it hybridizes under high stringency conditions to a nucleic acid sequence at least 95% identical to, such as at least 96% identical, at least 97% identical, at least 98% identical, at least 99% identical, or even 100% identical to SEQ ID NO: 26.

In some embodiments, the disclosed STLV-3 subtype D oligonucleotides comprise at least 15, 20, 25, 30, 35, 40, or more consecutive nucleotides of an STLV-3 subtype D nucleic acid sequence, such as 15, 20, 25, 30, 35, 40, or more consecutive nucleotides of STLV-3 subtype D a nucleic acid sequence set forth as SEQ ID NO: 1. In specific non-limiting examples, the disclosed STLV-3 subtype D oligonucleotide includes nucleotides 1-15, 16-30, or 31-45, etc., 2-16, 17-31, or 32-46, etc., or 3-17, 18-32, or 33-47, etc. of a STLV-3 subtype D nucleic acid sequence, such as nucleotides 1-15, 16-30, or 31-45, etc., 2-16, 17-31, or 32-46, etc., or 3-17, 18-32, or 33-47, etc. of the nucleic acid sequence set forth as SEQ ID NO: 1. In other specific non-limiting examples, the oligonucleotide includes nucleotides 1-20, 21-40, or 41-60, etc., 2-21, 22-41, or 42-61, etc., or 3-22, 23-42, or 43-62, etc. of a STLV-3 subtype D nucleic acid sequence, such as nucleotides 1-20, 21-40, or 41-60, etc., 2-21, 22-41, or 42-61, etc., or 3-22, 23-42, or 43-62, etc. of the nucleic acid sequence set forth as SEQ ID NO: 1. In further specific non-limiting examples, the oligonucleotide includes nucleotides 1-25, 26-50, 51-75, etc., 2-26, 27-51, or 52-76, or 2-27, 28-52, or 53-77, etc. of a STLV-3 subtype D nucleic acid sequence, such as nucleotides 1-25, 26-50, 51-75, etc., 2-26, 27-51, or 52-76, or 2-27, 28-52, or 53-77, etc. of the nucleic acid sequence set forth as nucleotides SEQ ID NO: 1. In one embodiment, the STLV-3 subtype D capsid, polymerase, protease, or envelope nucleic acid sequence is a target sequence for amplification.

A STLV-3 subtype D primer can be used to sequence a STLV-3 subtype D nucleic acid in order to identify a STLV-3 subtype D nucleic acid, for example to identify the presence of a STLV-3 subtype D nucleic acid in a sample, for example to detect the presence of STLV-3 subtype D in the sample. Alternatively, two, or more, STLV-3 subtype D primers can be used to amplify a region within a STLV-3 subtype D gene, for example by polymerase chain reaction (PCR) or more specifically by real-time PCR. In some examples, a primer comprises the nucleotide sequence as set forth as P5TAXF3 (SEQ ID NO: 21), P5TAXR3 (SEQ ID NO: 22), P5TAXF2 (SEQ ID NO: 23), or P5TAXR1 (SEQ ID NO: 24).

STLV-3 subtype D oligonucleotides, such as primers and probes, can be used to identify STLV-3 subtype D. Thus, these STLV-3 subtype D probes and primers specifically hybridize to a region in a STLV-3 subtype D nucleic acid which is unique to STLV-3 subtype D and not present in other viruses.

The primers and probes disclosed herein can be end-labeled (for example, radiolabeled, enzymatically-labeled, fluorescently-labeled, or biotinylated). One specific, non-limiting example of a primer label is a fluoresceinated STLV-3 subtype D primer. The probes disclosed herein can be fluorescently-labeled, such as for use in real-time PCR. In one embodiment, the oligonucleotide probes in the sample are labeled to render them readily detectable. Detectable labels may be any species or moiety that may be detected either visually or with the aid of an instrument. Detectable labels can be radioisotopes, chemiluminescent tags, haptens, or fluorescent markers. Specific, non-limiting examples of fluorescent markers include FITC, LIGHTCYCLER™ Red 640, LIGHTCYCLER™ Red 705, 6-carboxy-X-rhodamine (ROX), 5-carboxyfluorescein (FAM), 2'7'-dimethoxy-4'5'-dichloro-6-carboxyfluorescein (JOE), and 6-carboxy-2',4,7, 7'-tetrachlorofluorescein (TET). In one embodiment, the fluorescent markers coupled to the oligonucleotide probes have spectrally distinct emission spectra such that the amplified DNA sequences to which they specifically hybridize can be distinguished within the same reaction tube. In some embodiments, four, five, six, seven, or more probes that are sufficiently complementary to a STLV-3 subtype D nucleic acid sequence, such as a STLV-3 subtype D nucleic acid sequence set forth as SEQ ID NO: 1 may be used in a single reaction tube. Several examples of probes that can be used in the disclosed methods include HybProbes, Molecular beacon probes, TAQMAN® probes, amongst others.

HybProbes include an upstream probe labeled with a 3' donor fluorophore, such as FITC, and a downstream probe labeled with an acceptor fluorophore, such as LIGHTCYCLER™ Red 640 or Red 705, at the 5' terminus. The nucleic acid sequence of a HybProbe includes a nucleic acid sequence that detects the amplified product from the target nucleic acid sequence of interest, such as a STLV-3 subtype D sequence, for example, a STLV-3 subtype D capsid, protease, or envelope nucleic acid sequence. When the HybProbes are not hybridized to the target sequence, the donor fluorophore is excited by a filtered light source, such as by a LIGHTCYCLER™'s light emitting diode (LED), and a green fluorescent light is emitted at a slightly longer wavelength. However, when the pair of HybProbes hybridize to the target sequence, the two fluorophores are in close proximity to each other, for example within 1-10 nucleotides of each other, and the energy emitted by the excitation of the donor fluorophore excited the acceptor fluorophore, for example a LIGHTCYCLER™ Red 640 attached to the probe. The resultant energy transfer via FRET results in the emission of a red fluorescent light at an even longer wavelength. The intensity of the light emitted by the acceptor fluorophore is measured by the apparatus, such as a LIGHTCYCLER™. The increasing amount of measured fluorescence is proportional to the increasing amount of the amplified target nucleic acid generated during the ongoing PCR process. Since the acceptor fluorophore only emits a signal when both labeled probes are hybridized to the target nucleic acid sequence, the fluorescence measurement is performed after the annealing step in the PCR process.

Molecular beacon probes include probes coupled to a fluorescent marker in combination with a quencher molecule. The nucleic acid sequence of a molecular beacon probe includes a nucleic acid that detects the amplified product from the DNA sequence of interest, and sequences that permit the molecular beacon probe to form a hairpin structure. Attached to opposite ends (the 5' and the 3' end of the molecular beacon) are a fluorescent reporter molecule and a quencher molecule. When the molecular beacon is in the hairpin conformation (not hybridized to product) any fluorescence emitted by the fluorescent label is absorbed (quenched) by the quencher molecule via FRET and no fluorescence is detected. When a molecular beacon hybridizes to an amplified target nucleic acid with a complementary nucleic acid sequence, the fluorescent label and the quencher molecule are separated, and fluorescence is detected and can be measured during each PCR cycle. These probes are known to one of skill in the art (see the Molecular-Probes, Eugene, Oreg. website).

TAQMAN® probes include linear oligonucleotide probes with a 5' reporter fluorophore and a 3' quencher fluorophore, such as TAMRA. In the intact TAQMAN® probe, energy is transferred (via FRET) from the short-wavelength fluorophore to the long-wavelength fluorophore on the other end, quenching the short-wavelength fluorescence. After hybridization, the probe is susceptible to degradation by the endonuclease activity of a processing Taq polymerase. Upon degradation, FRET is interrupted, increasing the fluorescence from the short-wavelength fluorophore and decreasing fluorescence from the long-wavelength fluorophore.

Specific, non-limiting examples of quencher molecules include N,N,N',N'-tetramethyl-6-carboxyrhodamine (TAMRA) and 4-(4'-dimethylaminophenylazo)benzoic acid (DABCYL). Many suitable forms of these fluorescent markers and quenchers are widely available commercially with substituents on their phenyl moieties, which can be used as the site for coupling or as the coupling functionality for attachment to an oligonucleotide.

Expression of STLV-3 Subtype D Nucleic Aid Sequences

The STLV-3 subtype D polynucleotides disclosed herein include recombinant DNA which is incorporated into a vector; into an autonomously replicating plasmid or virus; or into the genomic DNA of a prokaryote or eukaryote, or which exists as a separate molecule (for example, a cDNA) independent of other sequences. DNA sequences encoding STLV-3 subtype D polypeptides, such as STLV-3 subtype D polypeptides, can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

STLV-3 subtype D polynucleotide sequences, such as STLV-3 subtype D capsid, protease, polymerase, tax polypeptide, rex polypeptide, and envelope polynucleotide sequences, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (for instance, ATG) in front of a protein-encoding gene, splicing signal for introns, maintenance of the correct reading frame of that gene to permit proper translation of mRNA, and stop codons.

Transformation of a host cell with recombinant DNA may be carried out by conventional techniques as are well known to those skilled in the art. Where the host is prokaryotic, such as $E.\ coli$, competent cells, which are capable of DNA uptake can be prepared from cells harvested after exponential growth phase and subsequently treated by the $CaCl_2$ method using procedures well known in the art. Alternatively, $MgCl_2$, or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with a STLV-3 subtype D polynucleotide sequences, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

Provided herein are the nucleic acid sequences that encode polypeptides, such as a STLV-3 subtype D capsid polypeptide, an STLV-3 subtype D protease, and an STLV-3 subtype D envelope polypeptide. In some embodiments, an isolated STLV-3 subtype D capsid polypeptide is provided that is at least 95% identical, such as at least 96%, at least 97%, at least 98%, at least 99%, or even 100% identical to the STLV-3 subtype D capsid polypeptide encoded by the nucleic acid sequence set forth as nucleotides 747-2009 of SEQ ID NO: 1. In some embodiments, an isolated STLV-3 subtype D envelope polypeptide is provided that is at least 95% identical, such as at least 96%, at least 97%, at least 98%, at least 99%, or even 100% identical to the STLV-3 subtype D envelope polypeptide encoded by the nucleic acid sequence set forth as nucleotides 5054-6535 of SEQ ID NO: 1. In some embodiments, an isolated STLV-3 subtype D protease is provided that is at least 95% identical, such as at least 96%, at least 97%, at least 98%, at least 99%, or even 100% identical to the STLV-3 subtype D protease encoded by the nucleic acid sequence set forth as nucleotides 1961-2494 of SEQ ID NO: 1. In some embodiments, an isolated STLV-3 subtype D polymerase is provided that is at least 95% identical, such as at least 96%, at least 97%, at least 98%, at least 99%, or even 100% identical to the STLV-3 subtype D polymerase encoded by the nucleic acid sequence set forth as nucleotides 2416-5061 of SEQ ID NO: 1. In some embodiments, an isolated STLV-3 subtype D tax polypeptide is provided that is at least 95% identical, such as at least 96%, at least 97%, at least 98%, at least 99%, or even 100% identical to the tax polypeptide encoded by SEQ ID NO: 25. In some embodiments, an isolated STLV-3 subtype D rex polypeptide is provided that is at least 95% identical, such as at least 96% identical, at least 97% identical, at least 98% identical, at least 99% identical, or even 100% identical to the rex polypeptide encoded by SEQ ID NO: 26.

The expression and purification of any of these STLV-3 subtype D proteins, by standard laboratory techniques, is now enabled. Fragments amplified as described herein can be cloned into standard cloning vectors and expressed in commonly used expression systems consisting of a cloning vector and a cell system in which the vector is replicated and expressed. Purified proteins may be used for functional analyses, antibody production, diagnosis, and subject therapy. Furthermore, the DNA sequences of the STLV-3 subtype D cDNAs can be manipulated in studies to understand the expression of STLV-3 subtype D genes and the function of their products. Partial or full-length cDNA sequences, which encode for the protein, may be ligated into bacterial expression vectors. Methods for expressing large amounts of protein from a cloned gene introduced into *E. coli* may be utilized for the purification, localization and functional analysis of proteins. For example, fusion proteins consisting of amino terminal peptides encoded by a portion of the *E. coli* lacZ or trpE gene linked to STLV-3 subtype D protein, such as a STLV-3 subtype D protease, capsid, or envelope protein, may be used to prepare polyclonal and monoclonal antibodies against this protein. Thereafter, these antibodies may be used to purify proteins by immunoaffinity chromatography, in diagnostic assays to quantitate the levels of protein and to localize proteins in tissues and individual cells by immunofluorescence and microscopy.

Intact native protein may also be produced in *E. coli* in large amounts for functional studies. Standard prokaryotic cloning vectors may also be used, for example, pBR322, pUC18, or pUC19 as described in Sambrook et al. (Molecular Cloning: A Laboratory Manual, $2^{nd}$ ed., vol. 1-3, Cold Spring Harbor, N.Y. 1989). Nucleic acids of STLV-3 subtype D may be cloned into such vectors, which may then be transformed into bacteria such as *E. coli*, which may then be cultured to express the protein of interest. Other prokaryotic expression systems include, for instance, the arabinose-induced pBAD expression system that allows tightly controlled regulation of expression, the IPTG-induced pRSET system that facilitates rapid purification of recombinant proteins and the IPTG-induced pSE402 system that has been constructed for optimal translation of eukaryotic genes. These three systems are available commercially from INVITROGEN™ and, when used according to the manufacturer's instructions, allow routine expression and purification of proteins.

Methods and plasmid vectors for producing fusion proteins and intact native proteins in bacteria are described in Sambrook et al. (Molecular Cloning: A Laboratory Manual, Cold Spring Harbor, N.Y., 1989, Chapter 17). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (Molecular Cloning: A Laboratory Manual, Cold Spring Harbor, N.Y., 1989) and are well known in the art. Often, proteins expressed at high levels are found in insoluble inclusion bodies. Methods for extracting proteins from these aggregates are described by Sambrook et al. (Molecular Cloning: A Laboratory Manual, Cold Spring Harbor, N.Y., 1989, Chapter 17).

Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). The STLV-3 subtype D fusion protein may be isolated from protein gels, lyophilized, ground into a powder, and used as an antigen. The DNA sequence can also be transferred to other cloning vehicles, such as other plasmids, bacteriophages, cosmids, animal viruses, and yeast artificial chromosomes (YACs) (Burke et al., *Science* 236:806-12, 1987). These vectors may then be introduced into a variety of hosts including somatic cells, and simple or complex organisms, such as bacteria, fungi (Timberlake and Marshall, *Science* 244:1313-7, 1989), invertebrates, plants (Gasser and Fraley, Science 244:1293, 1989), and mammals (Pursel et al., *Science* 244:1281-8, 1989), which cell or organisms are rendered transgenic by the introduction of one or more heterologous STLV-3 subtype D DNAs.

Various yeast strains and yeast-derived vectors are commonly used for expressing and purifying proteins, for example, *Pichia pastoris* expression systems are available from INVITROGEN™ (Carlsbad, Calif.). Such systems include suitable *Pichia pastoris* strains, vectors, reagents, transformants, sequencing primers and media.

Non-yeast eukaryotic vectors can also be used for expression of the STLV-3 subtype D proteins. Examples of such systems are the well known Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines. These expression systems are available from INVITROGEN™.

For expression in mammalian cells, the cDNA sequence may be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, *Cell* 23:175-82, 1981), to achieve transient or long-term expression. The stable integration of the chimeric gene construct may be maintained in mammalian cells by biochemical selection, such as neomycin (Southern and Berg, *J. Mol. Appl. Genet.* 1:327-41, 1982) and mycophenolic acid (Mulligan and Berg, *Proc. Natl. Acad. Sci. USA* 78:2072-6, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan and Berg, *Proc. Natl. Acad. Sci. USA* 78:2072-6, 1981; Gorman et al., *Proc. Natl. Acad. Sci USA* 78:6777-81, 1982). The level of expression of the cDNA can be manipulated with this type of vector, either by using promoters that have different activities (for example, the baculovirus pAC373 can express cDNAs at high levels in *S. frugiperda* cells (Summers and Smith, 1985, Genetically Altered Viruses and the Environment, Fields et al. (Eds.) 22:319-328, Cold Spring Harbor Laboratory Press, Cold Spring Harbor, N.Y.) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-6, 1981) or neo (Southern and Berg, *J. Mol. Appl. Genet.* 1:327-41, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell. Biol.* 1:486, 1981) or Epstein-Barr (Sugden et al., *Mol. Cell. Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human, or other mammalian cells, is now a conventional technique. The vectors are introduced into the recipient cells as pure DNA (transfection) by, for example, precipitation with calcium phosphate (Graham and vander Eb, 1973, *Virology* 52:466) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-7, 1980), or pellet guns (Klein et al, *Nature* 327:70., 1987). Alternatively, the cDNA can be introduced by infection with virus vectors. Systems are developed that use, for example, retroviruses (Bernstein et al., *Gen. Engrg.* 7:235, 1985), adenoviruses (Ahmad et al., *J. Virol.* 57:267, 1986), or Herpes virus (Spaete et al., *Cell* 30:295, 1982).

Using the above techniques, the expression vectors containing STLV-3 subtype D genes or cDNA sequence or fragments or variants or mutants thereof can be introduced into human cells, primate cells, mammalian cells from other species, or non-mammalian cells as desired. The choice of cell is determined by the purpose of the treatment. For example, monkey COS cells (Gluzman, *Cell* 23:175-82, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

One method that can be used to express STLV-3 subtype D polypeptides from the cloned STLV-3 subtype D cDNA sequence in mammalian cells is to use the cloning vector, pXT1. This vector is commercially available from STRATAGENE™, contains the Long Terminal Repeats (LTRs) and a portion of the GAG gene from Moloney Murine Leukemia Virus. The position of the viral LTRs allows highly efficient, stable transfection of the region within the LTRs. The vector also contains the Herpes Simplex Thymidine Kinase promoter (TK), active in embryonal cells and in a wide variety of tissues in mice, and a selectable neomycin gene conferring G418 resistance. Two unique restriction sites BglII and XhoI are directly downstream from the TK promoter. STLV-3 subtype D cDNA, including the entire open reading frame for an STLV-3 subtype D protein such as such as a STLV-3 subtype D protease, capsid, or envelope protein is cloned into one of the two unique restriction sites downstream from the promoter.

The ligated product is transfected into mouse NIH 3T3 cells using LIPOFECTIN™ (Life Technologies, Inc.) under conditions outlined in the product specification. Positive transfectants are selected after growing the transfected cells in 600 µg/ml G418 (Sigma, St. Louis, Mo.). The protein is released into the supernatant and may be purified by standard immunoaffinity chromatography techniques using antibodies raised against STLV-3 subtype D proteins.

Expression of STLV-3 subtype D proteins in eukaryotic cells can be used as a source of proteins to raise antibodies. The STLV-3 subtype D proteins may be extracted following release of the protein into the supernatant as described above, or, the cDNA sequence may be incorporated into a eukaryotic expression vector and expressed as a chimeric protein with, for example, β-globin. Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (STRATAGENE™). This vector encodes rabbit β-globin.

Methods of Detecting a STLV-3 Subtype D Nucleic acid

A major application of the STLV-3 subtype D nucleic acid sequences disclosed herein is for the detection of STLV-3 subtype D virus in a sample, such as a biological sample obtained from a subject that has or is suspected of having a STLV-3 subtype D infection. Accordingly, methods for the detection of STLV-3 subtype D are disclosed, for example to determine if a subject is infected with STLV-3 subtype D. The methods described herein may be used for any purpose where the detection of STLV-3 subtype D is desirable, including diagnostic and prognostic applications, such as in laboratory and clinical settings. A method for screening a subject to determine if the subject has been infected with STLV-3 subtype D is disclosed herein. In some examples, detection is performed for a nucleic acid sequence of STLV-3 subtype D ORFs or the polypeptides encoded by such ORFs, such as nucleotides 747-2009 of SEQ ID NO: 1, nucleotides 1961-2494 of SEQ ID NO: 1, nucleotides 2416-5061 of SEQ ID NO: 1 or nucleotides 5054-6535 of SEQ ID NO: 1. Any STLV-3 subtype D nucleic acid disclosed herein can be used in the disclosed methods. In some examples, a nucleic acid sequence encoding a STLV-3 subtype D envelope polypeptide is detected, such as the nucleic acid sequence set forth as nucleotides 5054-6535 of SEQ ID NO: 1 or a portion thereof. In some examples, a nucleic acid sequence encoding a STLV-3 subtype D protease is detected, such as nucleotides 1961-2494 of SEQ ID NO: 1 or a portion thereof. In some examples, a nucleic acid sequence encoding a STLV-3 subtype D capsid polypeptide is detected, such as nucleotides 747-2009 of SEQ ID NO: 1 or a portion thereof. In some examples, the nucleic acid sequence of a STLV-3 subtype D polymerase is detected, such as nucleotides 2416-5061 of SEQ ID NO: 1 or a portion thereof. In some examples, a nucleic acid sequence of a STLV-3 subtype D tax gene is detected, such as SEQ ID NO: 25 or a portion thereof. In some examples, a nucleic acid sequence of a STLV-3 subtype D rex gene is detected, such as SEQ ID NO: 26 or a portion thereof.

In some embodiments, the disclosed methods include providing a biological sample obtained from the subject, in which sample includes DNA or RNA, and providing an assay for detecting in the biological sample the presence of any of the STLV-3 subtype D nucleic acids or proteins. Appropriate samples include any conventional environmental or biological samples, including clinical samples obtained from a human or veterinary subject, such as a non-human primate. Suitable samples include all biological samples useful for detection of viral infection in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates. In particular embodiments, the biological sample is obtained from an animal subject, such as in the form of blood.

In some embodiments, methods for the detection of STLV-3 subtype D nucleic acids in a sample, and thus STLV-3 subtype D in a sample, include amplifying a STLV-3 subtype D nucleic acid from the sample, for example using two or more oligonucleotide primers at least 15 nucleotides in length that hybridize under very high stringency conditions to a STLV-3 subtype D nucleic acid sequence to produce amplified STLV-3 subtype D nucleic acids; and detecting the amplified STLV-3 subtype D nucleic acid, wherein the presence of an amplified STLV-3 subtype D nucleic acid indicates the presence of the STLV-3 subtype D virus in the sample. These include, but are not limited to, the nucleic acids sequences set forth as SEQ ID NO: 1 or a portion thereof. In some examples, a primer used to amplify a STLV-3 subtype D nucleic acid sequence comprises P5TAXF3 (SEQ ID NO: 21), P5TAXR3 (SEQ ID NO: 22), P5TAXF2 (SEQ ID NO: 23), or P5TAXR1 (SEQ ID NO: 24). In specific examples, a primer pair is used to amplify a STLV-3 subtype D nucleic acid sequence. In some embodiments, the primer pair includes a first primer containing the nucleic acid sequence set forth an SEQ ID NO: 21 and a second primer set forth as SEQ ID NO: 22. In some embodiments, the primer pair includes a first primer containing the nucleic acid sequence set forth an SEQ ID NO: 23 and a second primer set forth as SEQ ID NO: 24.

In specific examples, amplification of the STLV-3 subtype D nucleic acid includes the use of polymerase chain reaction (PCR), real-time PCR, reverse transcriptase-polymerase chain reaction (RT-PCR), real-time reverse transcriptase-polymerase chain reaction (rt RT-PCR), ligase chain reaction, or transcription-mediated amplification (TMA).

In some embodiments, methods for the detection of STLV-3 subtype D nucleic acids in a sample, and thus STLV-3 subtype D in a sample, include contacting the sample with a probe including a nucleic acid sequence at least 15 nucleotides in length that hybridizes under very high stringency conditions to an STLV-3 subtype D nucleic acid sequence, such as an amplified STLV-3 subtype D nucleic acid sequence; and detecting hybridization between the STLV-3 subtype D nucleic acid and the probe, wherein the detection of hybridization indicates the presence of the STLV-3 subtype D virus in the sample. In specific non-limiting examples a probe is selected such that it hybridizes under very high stringency conditions to an STLV-3 subtype D nucleic acid, such as but not limited to the sequence set forth as SEQ ID NO: 1 or a portion thereof.

One embodiment of such detection techniques is the polymerase chain reaction amplification of reverse transcribed RNA (RT-PCR) of RNA isolated from cells (for example lymphocytes) followed by direct DNA sequence determination of the products. The presence of one or more STLV-3 subtype D nucleic acids is taken as indicative of potential STLV-3 subtype D infection.

Oligonucleotides specific to normal, mutant or alternative sequences can be chemically synthesized using commercially available machines, labeled radioactively with isotopes (such as $^{32}P$) or non-radioactively, with tags such as biotin (Ward and Langer et al., *Proc. Natl. Acad. Sci. USA* 78:6633-57, 1981), and hybridized to individual DNA samples immobilized on membranes or other solid supports by dot-blot or transfer from gels after electrophoresis. The presence of these specific sequences are visualized by methods such as autoradiography or fluorometric (Landegren et al., *Science* 242: 229-37, 1989) or colorimetric reactions (Gebeyehu et al., *Nucleic Acids Res.* 15:4513-34, 1987). The absence of hybridization would indicate that the subject is not infected with STLV-3 subtype D.

Cloned DNA segments may be used as probes to detect specific DNA segments. The sensitivity of this method is greatly enhanced when combined with PCR (Wrichnik et al., *Nucleic Acids Res.* 15:529-42, 1987; Wong et al., *Nature* 330:384-6, 1987; Stoflet et al., *Science* 239:491-4, 1988). In this approach, a sequencing primer which lies within the amplified sequence is used with double-stranded PCR product or single-stranded template generated by a modified PCR. The sequence determination is performed by conventional procedures with radiolabelled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, *J. Mol. Biol.* 98:503, 1975). DNA fragments carrying the site (either normal, mutant, or alternative) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., *Proc. Nat. Acad. Sci. USA* 86:6230-4, 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify STLV-3 subtype D.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$, for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR-green or ethidium bromide). SYBR green is a fluorogenic minor groove binding dye that exhibits little fluorescence when in solution but emits a strong fluorescent signal upon binding to double-stranded DNA. Typically, SYBR green is used in singleplex reactions, however when coupled with melting point analysis, it can be used for multiplex reactions.

Any type of thermal cycler apparatus can be used for the amplification of the STLV-3 subtype D nucleic acid, such as a STLV-3 subtype D capsid, protease, or envelope nucleic acid, and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (STRATAGENE™; La Jolla, Calif.), or a GENEAMP® PCR System 9700 (Applied Biosystems; Foster City, Calif.). For real-time PCR, any type of real-time thermocycler apparatus can be used. For example, a BioRad iCycler iQ™, LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), or an MX4000™, MX3000™ or MX3005™ (STRATAGENE™; La Jolla, Calif.); DNA Engine Opticon Continuous Fluorescence Detection System (MJ Research); and Cepheid SMARTCYCLER™ can by used to amplify nucleic acid sequences in real-time.

In some embodiments, detecting the presence of a STLV-3 subtype D nucleic acid sequence in a sample includes the extraction of STLV-3 subtype D DNA. DNA extraction relates to releasing DNA from a latent or inaccessible form in a cell or sample and allowing the DNA to become freely available. In such a state, it is suitable for effective detection and/or amplification of the STLV-3 subtype D nucleic acid. Releasing DNA may include steps that achieve the disruption of cells. Additionally, extraction of RNA may include steps that achieve at least a partial separation of the RNA dissolved in an aqueous medium from other cellular components, wherein such components may be either particulate or dissolved.

In some embodiments, detecting the presence of a STLV-3 subtype D nucleic acid sequence in a sample includes the extraction of STLV-3 subtype D RNA. RNA extraction relates to releasing RNA from a latent or inaccessible form in a cell or sample and allowing the RNA to become freely available. In such a state, it is suitable for effective detection and/or amplification of the STLV-3 subtype D nucleic acid. Releasing RNA may include steps that achieve the disruption of cells. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular components, wherein such components may be either particulate or dissolved.

One of ordinary skill in the art will know suitable methods for extracting nucleic acids such as RNA and/or DNA from a sample; such methods will depend upon, for example, the type of sample in which the STLV-3 subtype D nucleic acid is found. For example, the nucleic acids may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. Nucleic acids can be extracted using standard methods. For instance, rapid nucleic acid preparation can be performed using a commercially available kit (such as the QIAGEN® DNA Mini kit (QIAGEN®) Roche MagNA Pure Compact Nucleic Acid Isolation Kit I or RNEASY® Mini Kit (QIAGEN®); NUCLISENS® NASBA Diagnostics (bioMérieux); or the MASTERPURE™ Complete DNA and RNA Purification Kit (EPICENTRE®)).

In some embodiments, the probe is detectably labeled, either with an isotopic or non-isotopic label; in alternative embodiments, the STLV-3 subtype D nucleic acid is labeled. Non-isotopic labels can, for instance, include a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples, the hybridization results in a detectable change in signal such as in increase or decrease in signal, for example from the labeled probe. Thus, detecting hybridization can include detecting a change in signal from the labeled probe during or after hybridization relative to signal from the label before hybridization.

STLV-3 Subtype D Proteins

Disclosed are STLV-3 subtype D polypeptides, such as STLV-3 subtype D polymerase polypeptides, STLV-3 subtype D envelope polypeptides, STLV-3 subtype D protease polypeptides, STLV-3 subtype D capsid polypeptides, STLV-3 subtype D rex polypeptides, and STLV-3 subtype D tax polypeptides.

In some embodiments, a STLV-3 subtype D Env polypeptide is at least 95% identical, such as at least 96%, at least 97%, at least 98%, at least 99%, or even 100% identical to the sequence set forth as below as SEQ ID NO: 15:

```
                                               (SEQ ID NO: 15)
MGKSSLFICLFCSYMASLFVPGDPSRCTLFIGASSYHSSPCGSNYPQCTW

TLDLVSLTRDQSLNPPCPDLVTYSQYHRPYSLYLFPHWITKPNRQGLGYY

SASYSDPCAIKCPYLGCQSWTCPYTGPMSSPYWKYTSDLNFTQKVSSVTL

HLHFSKCGSSFSLLLDAPGYDPVWFLSSQTTQAPPTPAPLTQDSDFQHIL

EPSVPWSSKILNLILLTLKSTNYSCMVCVDRSSLSSWHVLYDPLKVPKQH

EPRARALLRPSLAIPITNTTPPFPWSHCYCPLLQAVISNNCNNSVILPPF

SLSPVLDLSKPRQRRAVPIAVWLVSALAVGTGIAGGTTGSLSLASSRSLL
```

HEVDQDISHLTQAIVKNHNNILRVAQYAAQNRRGLDLLFWEQGGLCKAIR

EQCCFLNISNTHVSVLQERPPLEKRVITGWGLNWDLGLSQWAREALQTGI

TLLALFLLLIMVGPCVLRQLQALLFRLQHRSHPYSLLNRETNL.

In some embodiments, a STLV-3 subtype D capsid polypeptide is at least 95% identical, such as at least 96%, at least 97%, at least 98%, at least 99%, or even 100% identical to the sequence set forth as below as SEQ ID NO: 16:

(SEQ ID NO: 16)
MGNSYSRAANPIPKAPKGLAIHHWLNFLQAAYRLQPGPSEFDFHQLRNFL

KLAIKTPVWLNPINYSVLAELVPKNYPGRIQEIIAILIQETSTQEVPPSA

PPASEPQNPPPYPEPGQAIPQCLPVLHPHGAPAAHRPWQMKDLQAIKQEV

TSSAPGSPQFMQTVRLAVQQFDPTAKDLHDLLQYLCSSLVASLHHQQLET

LIAQAETQGITGYNPLAGPLRVQANNPTQQGLRREYQNLWLSAFSALPGN

TKDPTWAAILQGPEEPFCTFVERLNVALDNGLPEGTPKEPILRSLAYSNA

NKECQKLLQARGQTNGPLGDMLRACQAWTPRDKNKVLMVQPKKTPPPNQP

CFRCGQAGHWSRDCKQPRPPPGPCPLCQDPTHWKRDCPQLKPDPEEGMLL

DLPCEDPAARDQKNFIGGED.

In some embodiments, a STLV-3 subtype D protease polypeptide is at least 95% identical, such as at least 96%, at least 97%, at least 98%, at least 99%, or even 100% identical to the sequence set forth as below as SEQ ID NO: 17;

(SEQ ID NO: 17)
PSGQRPKKLHRGGGLASPQTVLPFIPLSQQKQPVLHVRVSFPGTPPVSIQ

ALLDTGADVTVLPARLCPPDLKLQDTTVLGASGPSTDKFKVLPCFTYVHL

PFRGRPVTLPSCLIDINNQWAILGRDVLQQCQSSLYLADQPSRVLPIQTP

SVIGLEHLPPPPEVPQFPLNQSASRP.

In some embodiments, a STLV-3 subtype D polymerase polypeptide is at least 95% identical, such as at least 96%, at least 97%, at least 98%, at least 99%, or even 100% identical to the sequence set forth as below as SEQ ID NO: 18:

(SEQ ID NO: 18)
HWAGTSPPAPRSSTISVKPERLQALTDLVSKALEAKYIEPYQGPGNNPIF

PVKKPNGKWRFIHDLRATNCLTKTLTSPSPGPPDLTSLPQGLPHLRTIDL

TDAFFQIPLPVAFQPYFAFTLPQPNNHGPGARYSWKVLPQGFKNSPTLFE

QQLSHILTPVRQAFPKSIVIQYMDDILLASPTLEESIVLAQEITNALAQE

GLPMSTEKTQSTPGPIHFLGQTISKKYITYETLPTIHVKPNWTLTELQST

LGELQWVSKGTPTLRSSLHQLYTALRGHHDPRDTIQLTPFQLQALNTLQK

ALTHNCRSRIVSNLPILALIMLRPTGTTAVLFQTKQKWPLVWLHTPHPAT

SLRLWGQLLANAIITLDKYSLQHYGQVCKSFHHNISNQALTHYLHTSDQS

SVAILLQHSHRFHNLGAQPSGPWKGLLQVPQIFQNVATLSPPFTISPVVI

NHAPCLFSDGSNSQAAFTIWDKKIIHQQVLPLPTASSAQAGELFALLAAL

RECKPWSSLNIFLDSKFLVGQLRRLALGAFIGPSTQCDLHSQLLPLLYNK

TIYVHHVRSHTLLQDPISRLNEATDALMLAPLLPLSPATLHEITHCNPPA

LCNHGATATETKAIVRACHTCKITNPQGRLPQGHIRRGHAPNTIWQGDVT

HLQYKKYKYCLLVWVDTYSGAVAVSCRRKETSSECVASLLAAISILGKPH

TINTDNGAAYLSQEFQQFCTSLSIKHTTHVPYNPTSSGLVERTNGILKTL

ISKYLLDDHHLPLDTAISKTLWTINHLNVLSSCQKTRWQLHQAQPLPPVP

ENLPLPEPVPKWYYYKIPGLTSSRWSGPVQSVKEAAGAALIPVGTRHIWI

PWRLLKRGACPRPGDSVTTESKHKDLQLHG.

In some embodiments, a STLV-3 subtype D rex polypeptide is at least 95% identical, such as at least 96%, at least 97%, at least 98%, at least 99%, or even 100% identical to the sequence set forth as below as SEQ ID NO: 19:

(SEQ ID NO: 19)
MPKTRRQRNHRIKTQRPSTPWPTFQVSGRACSTGTLSTFSAIVCRPIGAP

FPGGFVPPGYIGTPYWPPVLNTRSPGTPSMDALSARLYNTLSLASPPSPP

KELPAPSRSSPRRPLLQPPKFLPPSSMQSGNTPLSETTASSSPWESNYPP

CLSPTPASDPKMSIPCGEAPSCAYTSTNSHLQ.

In some embodiments, a STLV-3 subtype D tax polypeptide is at least 95% identical, such as at least 96%, at least 97%, at least 98%, at least 99%, or even 100% identical to the sequence set forth as below as SEQ ID NO: 20:

(SEQ ID NO: 20)
MAHFPGFGQSLLYGYPVYVFGDCVQADWCPISGGLCSARLHRHALLATCP

EHQITWDPIDGRVVSSPLQYLIPRLPSFPTQRTSRTLKVLTPPPTATTPK

VPPSFFHAVRKHTPFRNNCLELTLGEQLPAMSFPDPGLRPQNVYTMWGST

IVCLYLYQLTPPMTWPLIPHVIFCHPDQLGAFLTKIPTKRLEELLYKLFL

STGAILILPENCFPTTLFQPTRAPVIQAPWHSGLLPYLKEIVTPGLIWVF

TDGSSMISGPCPKEGQPSLVVQSSTFIFQKFQTKAYHPAFLLSHKLIQYS

SFHSLHLLFEEYTTVPFSLLFNEKEANDSDSKPQGEPQLLAKGHTVESS

V.

Quantitation of STLV-3 Subtype D Proteins

An alternative method of detecting a STLV-3 subtype D virus in a sample is to detect a STLV-3 subtype D protein in a sample, for example a sample obtained form a subject to determine if the subject has a STLV-3 subtype D infection, for example detecting a STLV-3 subtype D viral protein. These include, but are not limited to, the proteins encoded by the nucleic acid sequence set forth as nucleotides 747-2009 of SEQ ID NO: 1, nucleotides 1961-2494 of SEQ ID NO: 1, nucleotides 2416-5061 of SEQ ID NO: 1, nucleotides 5054-6535 of SEQ ID NO: 1, nucleotide 5054-5057 and 7232-8280 of SEQ ID NO: 1, or nucleotides 4995-5057 and 7232-7717 of SEQ ID NO: 1. The methods typically include contacting a sample with an antibody that specifically binds a STLV-3 subtype D polypeptide (such as a monoclonal or a polyclonal antibody that specifically binds a STLV-3 subtype D polypeptide), such as a STLV-3 subtype D polypeptide encoded by the nucleotide sequence according to nucleotides 747-2009 of SEQ ID NO: 1, nucleotides 1961-2494 of SEQ ID NO: 1, nucleotides 2416-5061 of SEQ ID NO: 1, nucleotides 5054-6535 of SEQ ID NO: 1, SEQ ID NO: 25, or SEQ ID NO: 26, and detecting binding of the antibody to a STLV-3 subtype D polypeptide in the sample, wherein binding of the antibody to the polypeptide indicates the presence of the STLV-3 subtype D polypeptide.

In some examples, the antibody is immobilized on a support surface, such as in the wells of a microtiter plate or on a column. The biological sample is then introduced onto the support surface and allowed to interact with the antibody to form complexes. Excess biological sample is then removed by washing, and the complexes are detected with a reagent, such as a second anti-STLV-3 subtype D polypeptide antibody, that is conjugated with a detectable marker.

In some examples, the cellular proteins are isolated and subjected to SDS-PAGE followed by Western blotting. After resolving the proteins, the proteins are transferred to a membrane, which is probed with a specific antibody that specifically binds a STLV-3 subtype D polypeptide. The STLV-3 subtype D polypeptide is detected, for example with labeled (such as horseradish peroxidase, HRP)-conjugated secondary antibodies, and quantitated.

In yet other examples, the level of one or more STLV-3 subtype D polypeptides in a cell is analyzed using microscopy. For example, using an antibody that specifically binds a STLV-3 subtype D polypeptide, such as but not limited to, a STLV-3 subtype D polypeptide encoded by the nucleotide sequence according to nucleotides 747-2009 of SEQ ID NO: 1, nucleotides 1961-2494 of SEQ ID NO: 1, nucleotides 2416-5061 of SEQ ID NO: 1, nucleotides 5054-6535 of SEQ ID NO: 1, SEQ ID NO: 25, or SEQ ID NO: 26, samples can be analyzed for the presence of one or more STLV-3 subtype D polypeptides. For example, frozen biopsied tissue sections are thawed at room temperature and fixed with acetone at $-200°$ C. for 5 minutes. Slides are washed twice in cold PBS for 5 minutes each, then air-dried. Sections are covered with 20-30 µl of antibody solution (15-45 µg/ml) (diluted in PBS, 2% BSA at 15-50 µg/ml) and incubated at room temperature in humidified chamber for 30 minutes. Slides are washed three times with cold PBS 5 minutes each, allowed to air-dry briefly (5 minutes) before applying 20-30 µl of the second antibody solution (diluted in PBS, 2% BSA at 15-50 µg/ml) and incubated at room temperature in humidified chamber for 30 minutes. The label on the second antibody may contain a fluorescent probe, enzyme, radiolabel, biotin, or other detectable marker. The slides are washed three times with cold PBS 5 minutes each then quickly dipped in distilled water, air-dried, and mounted with PBS containing 30% glycerol. Slides can be stored at 4° C. prior to viewing.

The foregoing methods of detecting STLV-3 subtype D may be assembled in the form of a diagnostic kit and preferably comprises either: hybridization with oligonucleotides; PCR amplification of the gene or a part thereof using oligonucleotide primers; RT-PCR amplification of the RNA or a part thereof using oligonucleotide primers; or direct sequencing of any of the STLV-3 subtype D genes present in a subject using oligonucleotide primers. The efficiency of these molecular genetic methods should permit the rapid identification of subjects infected with STLV-3 subtype D. Thus, kits can include containers with STLV-3 subtype D nucleic acid sequences (such as probes or primers) and/or containers including an antibody that specifically binds STLV-3 subtype D.

STLV-3 Subtype D Virus Antibodies

A STLV-3 subtype D polypeptide or a fragment or conservative variant thereof can be used to produce antibodies which are immunoreactive or bind to an epitope of the STLV-3 subtype D polypeptide. Accordingly, antibodies are disclosed (such as monoclonal or polyclonal antibodies) that specifically bind a STLV-3 subtype D polypeptide. In several example non limiting examples, the antibody binds a STLV-3 subtype D polypeptide encoded by the nucleotide sequence according nucleotides 747-2009 of SEQ ID NO: 1, nucleotides 1961-2494 of SEQ ID NO: 1, nucleotides 2416-5061 of SEQ ID NO: 1, or nucleotides 5054-6535 of SEQ ID NO: 1, SEQ ID NO: 25, or SEQ ID NO: 26. Polyclonal antibodies, antibodies which consist essentially of pooled monoclonal antibodies with different epitopic specificities, as well as distinct monoclonal antibody preparations are included.

The preparation of polyclonal antibodies is well-known to those skilled in the art. See, for example, Green et al., "Production of Polyclonal Antisera," in *Immunochemical Protocols* pages 1-5, Manson, ed., Humana Press 1992; Coligan et al., "Production of Polyclonal Antisera in Rabbits, Rats, Mice and Hamsters," in: *Current Protocols in Immunology*, section 2.4.1, 1992.

The preparation of monoclonal antibodies likewise is conventional. See, for example, Kohler & Milstein, *Nature* 256: 495, 1975; Coligan et al., sections 2.5.1-2.6.7; and Harlow et al., in: *Antibodies: a Laboratory Manual*, page 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, for example, syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from subhuman primate antibody. General techniques for raising therapeutically useful antibodies in baboons can be found, for example, in WO 91/11465, 1991, and Losman et al., *Int. J. Cancer* 46:310, 1990.

Alternatively, an antibody that specifically binds a STLV-3 subtype D polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE® Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. Methods of making these fragments are known in the art. (See for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. U.S.A.* 69:2659, 1972). Alternatively, the variable chains can be linked by an intermolecular disulfide bond or cross-linked by chemicals such as glutaraldehyde. See, for example, Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis, which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (for example, a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies, which mimic an epitope. For example, an anti-idiotypic monoclonal antibody made to a first monoclonal antibody will have a binding domain in the hypervariable region that is the "image" of the epitope bound by the first monoclonal antibody.

Effector molecules, such as therapeutic, diagnostic, or detection moieties (for example labels), can be linked to an antibody that specifically binds a STLV-3 subtype D polypep tide, using any number of means known to those of skill in the art. Both covalent and noncovalent attachment means may be used. The procedure for attaching an effector molecule to an antibody varies according to the chemical structure of the effector. Polypeptides typically contain a variety of functional groups; for example, carboxylic acid (COOH), free amine (—$NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable near the target site. Cleavage of the linker to release the effector molecule from the antibody may be prompted by enzymatic activity or conditions to which the immunoconjugate is subjected either inside the target cell or near the target site.

In view of the large number of methods that have been reported for attaching a variety of radiodiagnostic compounds, radiotherapeutic compounds, label (for example enzymes or fluorescent molecules) drugs, toxins, and other agents to antibodies, one skilled in the art will be able to determine a suitable method for attaching a given effector molecule to an antibody or other polypeptide.

The immunoconjugates can be prepared by cloning techniques. Examples of appropriate cloning and sequencing techniques, and instructions sufficient to direct persons of skill through many cloning exercises are found in Sambrook et al., *Molecular Cloning: A Laboratory Manual* (2nd Ed.), Vols. 1-3, Cold Spring Harbor Laboratory (1989), Berger and Kimmel (eds.), *Guide to Molecular Cloning Techniques*, Academic Press, Inc., San Diego Calif. (1987), or Ausubel et al. (eds.), *Current Protocols in Molecular Biology*, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® oratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.), and Applied Biosystems (Foster City, Calif.), as well as many other commercial sources known to one of skill.

Nucleic acids encoding native effector molecules or anti-STLV-3 subtype D antibodies can be modified to form the effector molecule, antibodies, or immunoconjugates. Modification by site-directed mutagenesis is well known in the art. Nucleic acids encoding effector molecule or anti-STLV-3 subtype D antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known in the art.

In one embodiment, immunoconjugates are prepared by inserting a cDNA which encodes an anti-STLV-3 subtype D polypeptide scFv antibody into a vector which comprises the cDNA encoding the effector molecule. The insertion is made so that the scFv and the EM are read in frame that is in one continuous polypeptide, which contains a functional Fv region and a functional EM region.

In addition to recombinant methods, the immunoconjugates, effector molecules, and antibodies can also be constructed in whole or in part using standard peptide synthesis. Solid phase synthesis of the polypeptides of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, "The Peptides: Analysis, Synthesis, Biology," Vol. 2, *Special Methods in Peptide Synthesis*, Part A. pp. 3-284; Merrifield et al. *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (for example, by the use of the coupling reagent N,N'-dicyclohexylcarbodiimide) are known to those of skill.

Once the nucleic acids encoding an EM, anti-STLV-3 subtype D antibody, or an immunoconjugate, are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

Antibodies can be covalently or non-covalently linked to a detectable label. Detectable labels suitable for such use include any composition detectable by spectroscopic, photochemical, biochemical, immunochemical, electrical, optical or chemical means. Useful labels in the present disclosure include magnetic beads (for example DYNABEADS®), fluorescent dyes (for example, fluorescein isothiocyanate, Texas red, rhodamine, green fluorescent protein, and the like), radiolabels (for example, $^3H$, $^{125}I$, $^{35}S$, $^{14}C$, or $^{32}P$) enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads.

The detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Immunogenic Compositions and Therapeutic Methods

Any of the STLV-3 subtype D polypeptides and nucleic acid molecules encoding the STLV-3 subtype D polypeptides disclosed herein can be used as immunogens, or to produce immunogens to elicit an immune response (for example as an immunogenic composition) to a STLV-3 subtype D polypeptide or a to a STLV-3 subtype D polypeptide expressing virus. These compositions are of use, for example, to reduce STLV-3 subtype D infection or a symptom of STLV-3 subtype D infection. Following administration of a therapeutically effective amount of the disclosed immunogenic composition, the subject can be monitored for STLV-3 subtype D infection, symptoms associated with STLV-3 subtype D infection, or both. Disclosed herein are methods of administering the therapeutic molecules disclosed herein (such as STLV-3 subtype D polypeptides and nucleic acids encoding STLV-3 subtype D polypeptides) to reduce STLV-3 subtype D infection. In several non-limiting examples, a therapeutically effective amount of a STLV-3 subtype D polypeptide encoded by nucleotides 747-2009 of SEQ ID NO: 1, nucleotides 1961-2494 of SEQ ID NO: 1, nucleotides 2416-5061 of SEQ ID NO: 1, SEQ ID NO: 25, SEQ ID NO: 26, or a immunogenic fragment thereof is administered to a subject.

In certain embodiments, the immunogenic composition includes an adjuvant. An adjuvant can be a suspension of minerals, such as alum, aluminum hydroxide, aluminum phosphate, on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif.

In one example, the immunogenic composition is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference herein in their entirety. A stabilizing detergent is any detergent that allows the components of the emulsion to remain as a stable emulsion. Such detergents include polysorbate 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for example, Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

Immunogenic compositions can be formulated with an appropriate solid or liquid carrier, depending upon the particular mode of administration chosen. If desired, the disclosed pharmaceutical compositions can also contain minor amounts of non-toxic auxiliary substances, such as wetting or emulsifying agents, preservatives, and pH buffering agents and the like, for example sodium acetate or sorbitan monolaurate. Excipients that can be included in the disclosed compositions include flow conditioners and lubricants, for example silicic acid, talc, stearic acid or salts thereof, such as magnesium or calcium stearate, and/or polyethylene glycol, or derivatives thereof.

Immunogenic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

A form of repository or "depot" slow release preparation can be used so that therapeutically effective amounts of the preparation are delivered into the bloodstream over many hours or days following transdermal injection or delivery. Such long acting formulations can be administered by implantation (for example subcutaneously or intramuscularly) or by intramuscular injection. The compounds can be formulated with suitable polymeric or hydrophobic materials (for example as an emulsion in an acceptable oil) or ion exchange resins, or as sparingly soluble derivatives, for example, as a sparingly soluble salt.

Immunogenic compositions that include a disclosed therapeutic agent can be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide subjects with a constant and long-term dosage or infusion of a therapeutic agent. Such device can be categorized as either active or passive.

Active drug or programmable infusion devices feature a pump or a metering system to deliver the agent into the subject's system. An example of such an active infusion device currently available is the Medtronic SYN-CHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, immunogenic compositions including a disclosed therapeutic agent are administered by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

Immunogenic compositions can be administered for therapeutic treatments. In therapeutic applications, a therapeutically effective amount of the immunogenic composition is administered to a subject suffering from a disease, such as STLV-3 subtype D infection. The immunogenic composition can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle (see, for example, Banga, supra). A particulate carrier based on a synthetic polymer has been shown to act as an adjuvant to enhance the immune response, in addition to providing a controlled release. Aluminum salts can also be used as adjuvants to produce an immune response.

Immunogenic compositions can be formulated in unit dosage form, suitable for individual administration of precise dosages. In pulse doses, a bolus administration of an immunogenic composition that includes a disclosed immunogen is provided, followed by a time-period wherein no disclosed immunogen is administered to the subject, followed by a second bolus administration. A therapeutically effective amount of an immunogenic composition can be administered in a single dose, or in multiple doses, for example daily, during a course of treatment. In specific, non-limiting examples, pulse doses of an immunogenic composition that include a disclosed immunogen are administered during the course of a day, during the course of a week, or during the course of a month.

Immunogenic compositions can be administered whenever the effect (such as decreased signs, symptom, or laboratory results of STLV-3 subtype D infection) is desired. Generally, the dose is sufficient to treat or ameliorate symptoms or signs of disease without producing unacceptable toxicity to the subject. Systemic or local administration can be utilized.

Amounts effective for therapeutic use can depend on the severity of the disease and the age, weight, general state of the subject, and other clinical factors. Thus, the final determination of the appropriate treatment regimen will be made by the attending clinician. Typically, dosages used in vitro can provide useful guidance in the amounts useful for in situ administration of the pharmaceutical composition, and animal models may be used to determine effective dosages for treatment of particular disorders. Various considerations are described, for example in Gilman et al., eds., Goodman and Gilman: The Pharmacological Bases of Therapeutics, 8th ed., Pergamon Press, 1990; and Remington's Pharmaceutical Sciences, 17th ed., Mack Publishing Co., Easton, Pa., 1990. Typically, the dose range for a STLV-3 subtype D polypeptide is from about 0.1 μg/kg body weight to about 100 mg/kg body weight. Other suitable ranges include doses of from about 1 μg/kg to 10 mg/kg body weight. In one example, the dose is about 1.0 μg to about 50 mg, for example, 1 μg to 1 mg, such as 1 mg peptide per subject. The dosing schedule can vary from daily to as seldom as once a year, depending on clinical factors, such as the subject's sensitivity to the peptide and tempo of their disease. Therefore, a subject can receive a first dose of a disclosed therapeutic molecule, and then receive a second dose (or even more doses) at some later time(s), such as at least one day later, such as at least one week later.

The pharmaceutical compositions disclosed herein can be prepared and administered in dose units. Solid dose units include tablets, capsules, transdermal delivery systems, and suppositories. The administration of a therapeutic amount can be carried out both by single administration in the form of an individual dose unit or else several smaller dose units and also by multiple administrations of subdivided doses at specific intervals. Suitable single or divided doses include, but are not limited to about 0.01, 0.1, 0.5, 1, 3, 5, 10, 15, 30, or 50 μg protein/kg/day.

The nucleic acid constructs encoding antigenic STLV-3 subtype D polypeptides described herein are used, for example, in combination, as pharmaceutical compositions (medicaments) for use in therapeutic, for example, prophylactic regimens (such as vaccines) and administered to subjects (for example, primate subjects such as human subjects) to elicit an immune response against STLV-3 subtype D. For example, the compositions described herein can be administered to a human (or non-human) subject prior to infection with STLV-3 subtype D to inhibit infection by or replication of the virus. Thus, the pharmaceutical compositions described above can be administered to a subject to elicit a protective immune response against STLV-3 subtype D. To elicit an immune response, a therapeutically effective (for example, immunologically effective) amount of the nucleic acid constructs are administered to a subject, such as a human (or non-human) subject.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin).

For administration of STLV-3 subtype D nucleic acid molecules, the nucleic acid can be delivered intracellularly, for example by expression from an appropriate nucleic acid expression vector which is administered so that it becomes intracellular, such as by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). The present disclosure includes all forms of nucleic acid delivery, including synthetic oligos, naked DNA, plasmid and viral, integrated into the genome or not.

In another approach to using nucleic acids for immunization, an immunogenic STLV-3 subtype D polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (*Bacillus Calmette Guerin*) provides another vector for expression of the peptides (see Stover, Nature 351:456-460, 1991).

In one example, a viral vector is utilized. These vectors include, but are not limited to, adenovirus, herpes virus, vaccinia, or an RNA virus such as a retrovirus. In one example, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated. By inserting a nucleic acid sequence encoding a STLV-3 subtype D polypeptide into the viral vector, along with another gene that encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the polynucleotide encoding a STLV-3 subtype D polypeptide.

Since recombinant retroviruses are defective, they need assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Suitable formulations for the nucleic acid constructs, include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the composition for use in the inventive method is formulated to protect the nucleic acid constructs from damage prior to administration. For example, the composition can be formulated to reduce loss of the adenoviral vectors on devices used to prepare, store, or administer the expression vector, such as glassware, syringes, or needles. The compositions can be formulated to decrease the light sensitivity and/or temperature sensitivity of the components. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof.

In therapeutic applications, a therapeutically effective amount of the composition is administered to a subject prior to or following exposure to or infection by STLV-3 subtype D. When administered prior to exposure, the therapeutic application can be referred to as a prophylactic administration (such as in the form of a vaccine). Single or multiple administrations of the compositions are administered depending on the dosage and frequency as required and tolerated by the subject. In one embodiment, the dosage is administered once as a bolus, but in another embodiment can be applied periodically until a therapeutic result, such as a protective immune response, is achieved. Generally, the dose is sufficient to treat or ameliorate symptoms or signs of disease without producing unacceptable toxicity to the subject. Systemic or local administration can be utilized.

In the context of nucleic acid vaccines, naturally occurring or synthetic immunostimulatory compositions that bind to and stimulate receptors involved in innate immunity can be administered along with nucleic acid constructs encoding the STLV-3 subtype D polypeptides. For example, agents that stimulate certain Toll-like receptors (such as TLR7, TLR8 and TLR9) can be administered in combination with the nucleic acid constructs encoding STLV-3 subtype D polypeptides. In some embodiments, the nucleic acid construct is administered in combination with immunostimulatory CpG oligonucleotides.

Nucleic acid constructs encoding STLV-3 subtype D polypeptides can be introduced in vivo as naked DNA plasmids. DNA vectors can be introduced into the desired host cells by methods known in the art, including but not limited to transfection, electroporation (for example, transcutaneous electroporation), microinjection, transduction, cell fusion, DEAE dextran, calcium phosphate precipitation, use of a gene gun, or use of a DNA vector transporter (See for example, Wu et al. J. Biol. Chem., 267:963-967, 1992; Wu and Wu J. Biol. Chem., 263:14621-14624, 1988; and Williams et al. Proc. Natl. Acad. Sci. USA 88:2726-2730, 1991). As described in detail in the Examples, a needleless delivery device, such as a BIOJECTOR® needleless injection device can be utilized to introduce the therapeutic nucleic acid constructs in vivo. Receptor-mediated DNA delivery approaches can also be used (Curiel et al. Hum. Gene Ther., 3:147-154, 1992; and Wu and Wu, J. Biol. Chem., 262:4429-4432, 1987). Methods for formulating and administering naked DNA to mammalian muscle tissue are disclosed in U.S. Pat. Nos. 5,580,859 and 5,589,466, both of which are herein incorporated by reference. Other molecules are also useful for facilitating transfection of a nucleic acid in vivo, such as a cationic oligopeptide (for example, WO95/21931), peptides derived from DNA binding proteins (for example, WO96/25508), or a cationic polymer (for example, WO95/21931).

Another well known method that can be used to introduce nucleic acid constructs encoding STLV-3 subtype D immunogens into host cells is particle bombardment (also know as biolistic transformation). Biolistic transformation is commonly accomplished in one of several ways. One common method involves propelling inert or biologically active particles at cells. This technique is disclosed in, for example, U.S. Pat. Nos. 4,945,050, 5,036,006; and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. Proc. Natl. Acad. Sci. USA 84:7413-7417, 1987; Mackey, et al. Proc. Natl. Acad. Sci. USA 85:8027-8031, 1988; Ulmer et al. Science 259:1745-1748, 1993). The use of cationic lipids can promote encapsulation of negatively charged nucleic acids, and also promote fusion with negatively charged cell membranes (Felgner and Ringold Science 337:387-388, 1989). Particularly useful lipid compounds and compositions for transfer of nucleic acids are described in WO95/18863 and WO96/17823, and in U.S. Pat. No. 5,459,127, herein incorporated by reference.

As with the immunogenic polypeptide, the nucleic acid compositions may be administered in a single dose, or multiple doses separated by a time interval can be administered to elicit an immune response against STLV-3 subtype D. For example, two doses, or three doses, or four doses, or five doses, or six doses or more can be administered to a subject over a period of several weeks, several months or even several years, to optimize the immune response.

EXAMPLES

Example 1

This example describes the material and methods used to obtain STLV-3 subtype D sequences.

Sample Collection and Preparation

Self-identified hunters were recruited from 17 villages in southern Cameroon and were trained to collect dried blood spots (DBS) from freshly collected monkey bushmeat. Preliminary species identification of hunted non-human primates (NHPs) was determined using pictographs of NHPs common in the region. Hunters were not given incentives for collection of the bushmeat samples but were educated about the risks associated with direct contact with primate samples and were instructed on appropriate prevention measures. A total of 362 DBS from hunted NHPs was collected on Whatman filter paper, air-dried at room temperature, and temporarily stored in envelopes with silica gels. Specimens were then stored at −20° C. until processed. Nucleic acids were extracted from DBS using the NUCLISENS® nucleic acid isolation kits (Biomérieux, Durham, N.C.). Briefly, DBS were incubated in lysis buffer for 2 hours at room temperature, nucleic acids were eluted from a silica suspension with wash buffer containing guanidine thiocyanate. Ethanol-precipitated nucleic acids were resuspended in 50 µl of water and stored at 4° C. until tested. DNA quality and yield were determined by semi-quantitative PCR amplification of the β-actin gene according to standard procedures (Switzer et al. *Transplantation* 71:959-96, 2001).

Primate T-Cell Lymphoma/Leukaemia Viruses (PTLV) Sequence Amplification and NHP Species Identification NHP DNAs were tested for tax sequences using generic, nested PCR assays capable of detecting viruses from all four major primate T-cell lymphoma/leukaemia viruses (PTLV) groups as described by Busch et al. (*Transfusion* 40:443-449, 2000, incorporated herein by reference) and Van Dooren et al. (*J. Gen. Virol.* 85:507-519, 2004, incorporated herein by reference). Phylogenetic resolution within the identified PTLV groups was achieved by analysis of long terminal repeat (LTR) sequences obtained with PCR primers specific for each PTLV group. PCR amplification of overlapping regions of the 5' and 3' STLV-1 LTR was performed using primers and conditions described by Meertens et al. (*Virology* 287:275-

285, 2001, incorporated herein by reference). STLV-3 LTR sequences were obtained using PCR primers and conditions reported by Wolfe et al. (*Proc. Natl. Acad. Sci. U.S.A.* 102: 7994-7999, 2005).

STLV-3 Subtype D Specific PCR Assay

Confirmation of primate species was done by analysis of mitochondrial cytochrome oxidase subunit II (COXII) and glucose-6-phosphate dehydrogenase (G6PD) sequences PCR-amplified from DBS DNA using primers PCO2F2 and PCO2R1, or GPDF1 and GPDR1, respectively (Switzer et al. *Nature* 434:376-380, 2005, incorporated herein by reference).

PCR products were visualized on 1.8% agarose gels stained with ethidium bromide and were purified with QIAQUICK® PCR or gel purification kits (QIAGEN®, Valencia, Calif.). Using an ABI 3130×1 sequencer, purified amplicons were either directly sequenced on both strands using ABI PRISM® Big Dye terminator kits (Foster City, Calif.), or after cloning into a TOPO® vector (INVITROGEN™).

Identification of a Novel PTLV Group

Using a PCR-based genome walking approach (Switzer et al. *J. Virol.* 80:7427-7438, 2006, incorporated herein by reference), new primer sets were designed to amplify partial fragments of the viral genome (see Table 1). Larger tax sequences (658-bp and 656-bp) were amplified from animals Cmo8699AB and Cni7867AB, respectively with external primers 8699TF1 and PGTAXR1 and internal primers 8699TF2 and PGTAXR2, with 40 cycles of standard PCR conditions and annealing temperatures of 45° C. and 50° C., respectively. Overlapping sequences from animal Cmo8699AB from the 3' end of the tax gene to LTR were obtained by semi-nested PCR using the external and internal forward primers 8699TF6 and 8699TF8 with reverse primer PGTATA1+2R1. For animal Cni7867AB, the internal primers 8699TF7 and PGTATA1+2R1 were used to amplify the tax-LTR fragment. The remainder of the LTR sequences from both animals were amplified by semi-nested PCR with external primers 8699LF3 and PGPBSR1n and internal primers 8699LF4 and PGPBSR1n. The PCR reactions included 40 cycles of standard PCR conditions, an annealing temperature of 45° C. and primer extension time of 2.5 minutes.

Nucleotide Sequence Accession Numbers

GenBank accession numbers for the STLV-1 LTR, STLV-3 LTR, STLV-3 (Cmo8699AB) tax-LTR, and small tax sequences are EU152271-EU152276, EU152277-EU152279, EU152280-EU152281, and EU152282-EU152293, respectively.

TABLE 1

PCR Primers for Amplification of the Viral Genome

| Primer Name | Sequence | SEQ ID NO: |
|---|---|---|
| 8699TF1 | GTACCCTGTCTACGTTTTCGGCGAT | 4 |
| PGTAXR1 | GAIGA(T/C)TGIA(C/G)TAC(T/C)AAAGATGGCTG | 5 |
| 8699TF2 | TTACTGGCCACCTGTCCTGAACAC | 6 |
| PGTAXR2 | TTIGGG(T/C)AIGGICCGGAAATCAT | 7 |
| 8699TF6 | CATCCGGACCAACTAGGGGCCTTC | 8 |
| 8699TF8 | CAGCCCACCCGCGCACCAGTAATT | 9 |

TABLE 1-continued

PCR Primers for Amplification of the Viral Genome

| Primer Name | Sequence | SEQ ID NO: |
|---|---|---|
| PGTATA1 + 2R1 | TCCTGAAC(T/C)GTC(T/C)(T/C)(T/C)(A/G)CGCTTTTATAG | 10 |
| 8699TF7 | AACAAAAATCCCTACCAAACGCTT | 11 |
| 8699LF3 | CTCTGACGTCTCTCCCTGCCTTGT | 12 |
| PGPBSR1n | ATCCCGGACGAGCCCCCA | 13 |
| 8699LF4 | CCGGAAAAAACCTTAAACCACCCA | 14 |

An 325-bp env gene region of STLV-3 subtype D was amplified using generic and nested forward primers, PGENVF1 and PGENVF2, and reverse primers, PGENVF2 and PGENVR2, respectively, in standard PCR conditions as described by Switzer et al. (*J. Virol.* 80:7427-7438, 2006, incorporated herein by reference).

Sequence Analysis

Percent nucleotide divergence was calculated using the GAP program in the Genetics Computer Group (GCG) Wisconsin package (Womble, *Methods Mol. Biol.* 132:3-22, 2000). Sequences were aligned using the Clustal W program followed by manual editing. Gaps were removed and distance-based phylogenetic trees were generated using the Kimura two-parameter model together with the neighbor-joining method in the MEGA program (version 3.1) and maximum-likelihood (ML) analysis in the PAUP* program (Switzer et al. *Nature* 434:376-380, 2005).

The reliability of the final topology of the trees was tested with 1,000 bootstrap replicates. PTLV diversity was analyzed using the phylogeny inferred from the larger tax sequences using the TreePAT package of the TreeDyn software build 198.3. TreePAT generates a visual representation of a phylogenetic tree in a pairwise distance matrix of the branch lengths of the tree between each pair of taxa, with a distance of zero for a taxa to itself. Ranges of genetic distances, or classes, were empirically investigated based on accepted PTLV taxonomic groups using available full-length genomes. Colors are assigned to each class with the distance matrix being colored so that taxa within a given distance class appear with their respective colors as squares along the diagonal of the matrix allowing for a visual comparison of divergence levels between taxa and/or viral groups.

Dating the Origin of STLV-3

Additional molecular analyses were performed to estimate the divergence times of the most recent common ancestor (MRCA) of STLV-3 (from animal Cmo8699AB). The molecular clock hypothesis was not rejected for the 881-bp alignment of PTLV and BLV tax sequences in both the PAUP* and Tree-Puzzle analyses (P=0.012 and 0.858, respectively). For this analyses, the molecular clock was enforced and calibrated the tree using a value of 40,000-60,000 years ago (ya) estimated for the origin of the Melanesian HTLV-1. By using these dates and methods, the evolutionary rate for PTLV was estimated to be $9.17 \times 10^{-7}$ to $1.38 \times 10^{-6}$ substitutions/site/year which is consistent with rates determined previously both with and without enforcing a molecular clock. The evolutionary rate for STLV-3 (from animal Cmo8699AB) is estimated to be $2.11 \times 10^{-6}$ to $3.16 \times 10^{-6}$ and the MRCA is inferred to have occurred about 92,072-138,560 ya suggesting an ancient origin and perhaps the identification of one of the oldest viruses in the PTLV-3 group.

Figure 2:
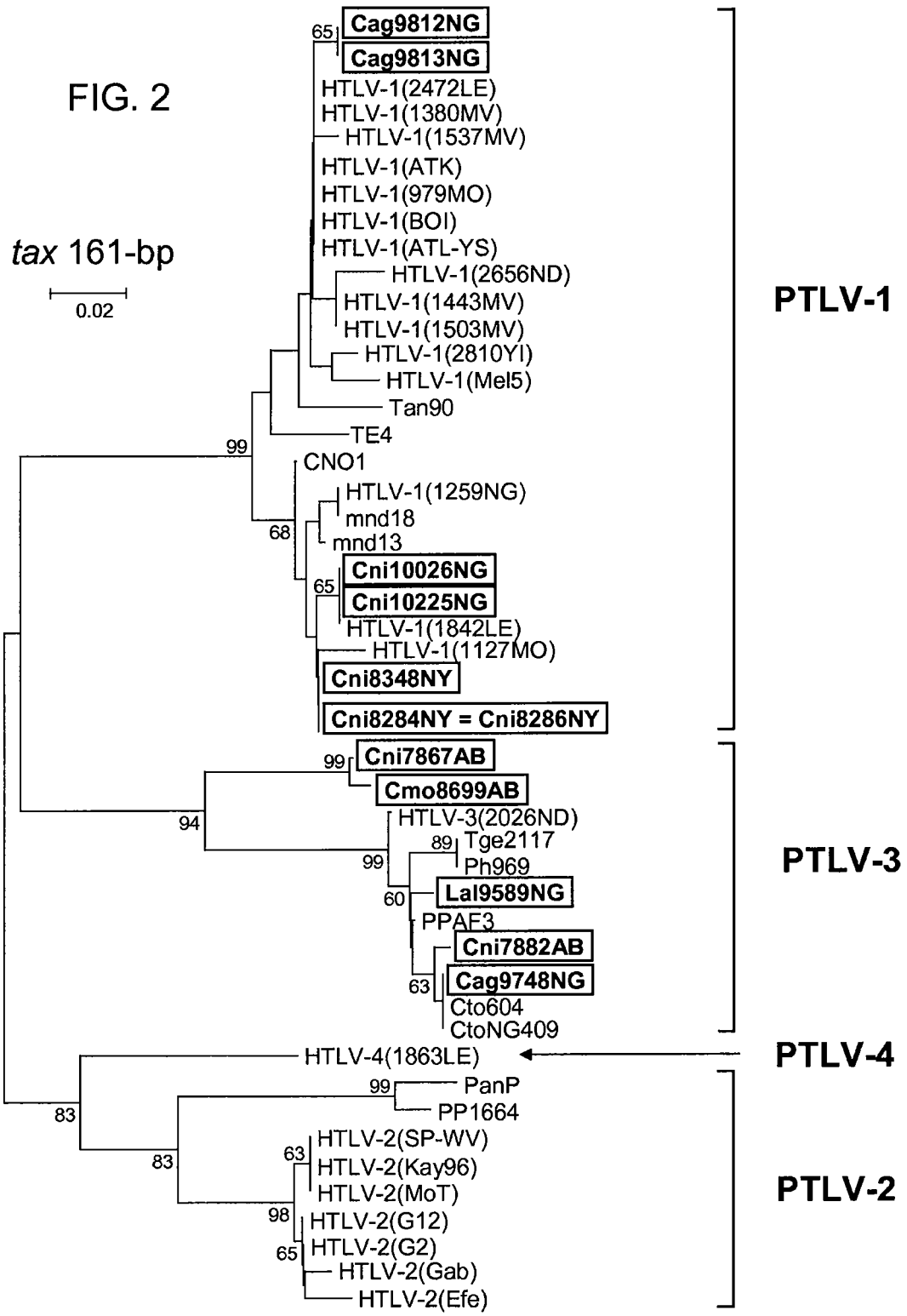
FIG. 2 is a phylogenetic tree that depicts PTLV phylogeny inferred using 161-bp tax sequences. New sequences from nonhuman primates (NHPs) from Cameroon in this study are boxed. NHPs are coded using the first letter of the genus followed by the first two letters of the species name: *Cercocebus agilis* (Cag), *Cercopithecus nictitans* (Cni), *Cercopithecus mona* (Cmo), and *Lophocebus albigena* (Lal). The last two letters in the monkey name indicate the study site. Support for the branching order was determined by 1,000 bootstrap replicates; only values ≥60% are shown. Branch lengths are proportional to the evolutionary distance (scale bar) between the taxa.

A total of 362 DBS representing 12 primate and prosimian species were collected from 4 sites in southern Cameroon. From these, 215 DBS (60%) had adequate blood spot quality and quantity for nucleic acid extraction. Of the 215 samples tested, 170 (79%) yielded adequate DNA integrity through the amplification of the β-actin gene (Table 2). The presence of blood clots and limited volumes of blood on some DBS may account for the poor DNA yield of some samples.

this small region of tax (FIG. 2, Table 4). BLAST analysis of these divergent tax sequences identified sequence similarity (~92-93%) to very short STLV-3-like tax sequences (~219-bp) from four *C. nictitans* from southern Cameroon (Cni217, Cni227, Cni3034, and Cni3038; GenBank accession numbers AY039033, AF412120, AM746663, and, AM746660, respectively) (Table 4). However, further phylogenetic analysis of STLV-3 (from animal Cmo8699AB) and STLV-3 (from animal Cni7867AB) including the small tax sequences from 3 of the 4 *C. nictitans* (Cni3034 was omitted because it had a

TABLE 2

Distribution of PTLV in wild-caught simian and pro-simian species

| Species | Common name | # DBS extracted[1] | # β-actin positive (%) | # tax positive[2] (%) | # STLV-1 LTR positive | # STLV-3 LTR positive |
|---|---|---|---|---|---|---|
| Old World Monkeys | | | | | | |
| *Cercocebus agilis* | agile mangabey | 6 | 3 (50) | 3 (100) | 2 | 1 |
| *Cercopithecus cephus* | moustached monkey | 41 | 32 (78) | 0 | 0 | 0 |
| *Cercopithecus mona* | mona monkey | 40 | 36 (90) | 1 (2.7) | 0 | 1 |
| *Cercopithecus neglectus* | De Brazza's monkey | 1 | 1 (100) | 0 | 0 | 0 |
| *Cercopithecus nictitans* | spot-nosed monkey | 98 | 73 (74.5) | 7 (9.6) | 4 | 2 |
| *Cercopithecus pogonias* | crowned monkey | 9 | 8 (88.8) | 0 | 0 | 0 |
| *Colobus guereza* | guereza colobus | 3 | 2 (66.7) | 0 | 0 | 0 |
| *Lophocebus albigena* | grey-cheeked monkey | 10 | 9 (90) | 1 (11.1) | 0 | 1 |
| Prosimian | | | | | | |
| *Arctocebus aureus* | golden angwantibo | 2 | 1 (50) | 0 | 0 | 0 |
| *Arctocebus calabarensis* | calabar angwantibo | 2 | 2 (100) | 0 | 0 | 0 |
| *Galago alleni* | Allen's galago | 1 | 1 (100) | 0 | 0 | 0 |
| *Perodicticus potto* | potto | 2 | 2 (100) | 0 | 0 | 0 |
| Total | | 215 | 170 (79.1) | 12 (7.1) | 6 (3.5) | 5 (2.9) |

[1]DBS, dried blood spots
[2]samples testing negative for β-actin sequences were not tested for PTLV sequences High PTLV diversity and geographic distribution were observed among wild monkeys hunted for bush meat in southern Cameroon. Of the 170 samples screened, 12 (7%) from four NHP species were positive for PTLV tax sequences using a generic PCR assay (Table 3). Phylogenetic analysis of the short tax sequences from these 12 samples showed that 7 NHPs (two *Cercocebus agilis* and five *Cercopithecus nictitans*) were infected with STLV-1, while 3 NHPs (*C. agilis, C. nictitans*, and *Lophocebus albigena*) were infected with STLV-3 (FIG. 2 and Table 3). No evidence was observed of infection of *C. agili* with STLV-2, HTLV-4-like STLV, or dual STLV-1 and STLV-3s.

Figure 3:
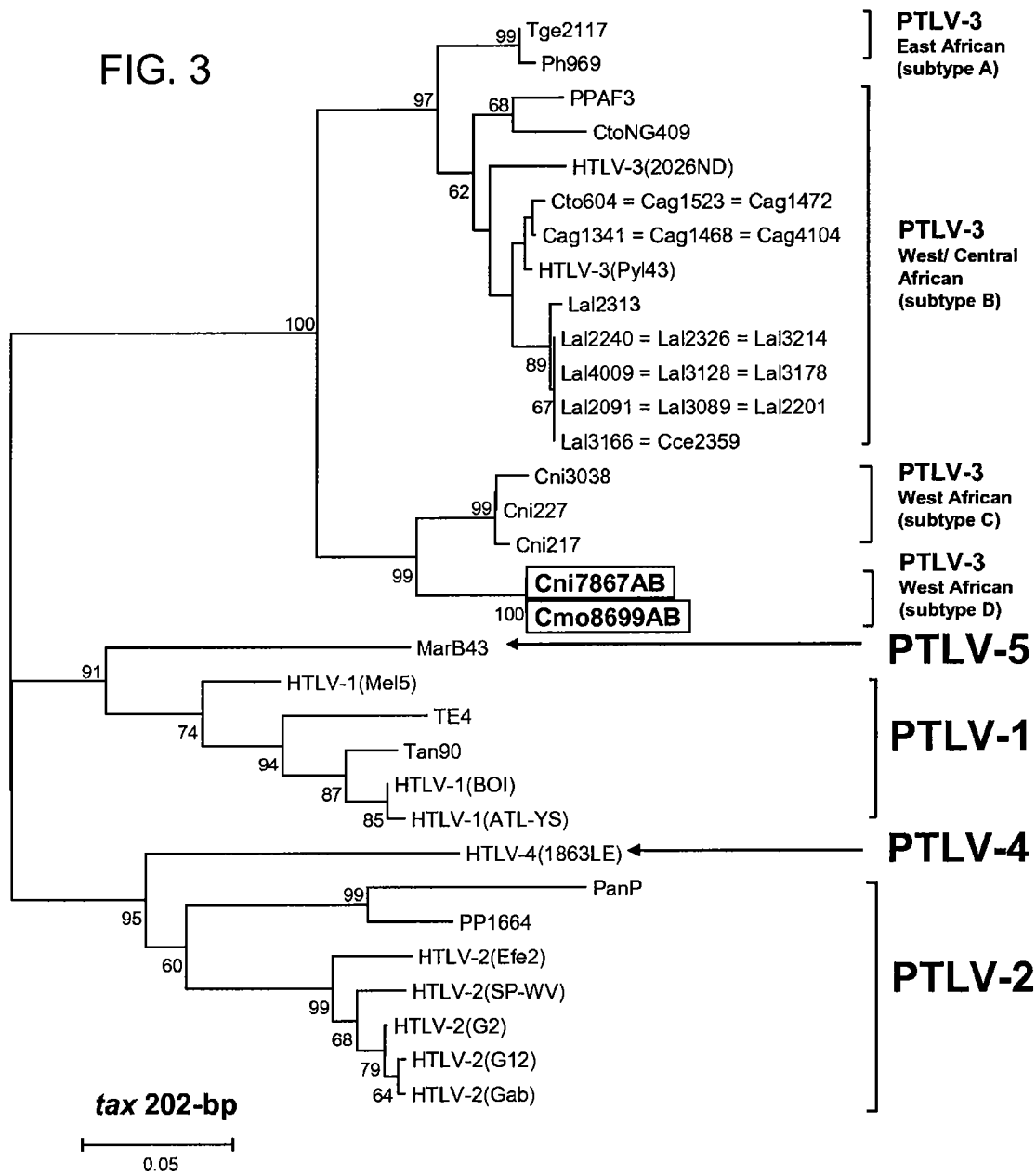
FIG. 3 is a phylogenetic tree that depicts the identification of a novel PTLV-3 subtype by phylogenetic inference of 202-bp tax sequences with PTLV prototypes and partial sequences from three *C. nictitans* (Cni217, Cni227, and Cni3038) and those identified shown in the current application (boxed). GENBANK® accession numbers for the previously reported partial STLV-3 tax sequences included in this analysis are AY039033, AF412120, and AM746647-AM746673). NHPs are coded using the first letter of the genus followed by the first two letters of the species name: *C. mona* (Cmo), *Cercopithecus nictitans* (Cni). The last two letters in the sample name indicate the study site. Support for the branching order was determined by 1,000 bootstrap replicates; only values ≥60% are shown. Branch lengths are proportional to the evolutionary distance (scale bar) between the taxa.

The samples obtained from animals Cmo8699AB and Cni7867AB, both collected near the same village but from two different primate species, were found to contain nearly identical STLV sequences with highest nucleotide identity to viruses in the PTLV-3 group, but exhibited high divergence in shorter but identical tax sequence to Cni3038) and other STLV-3-infected species (*L. albigena, C. agilis*, and *C. cephus*) from the same region showed that the new STLV-3 (viral subtype D) viruses cluster tightly with high bootstrap support (99) as a distinct monophyletic subtype of STLV-3 (FIG. 3). Since there is generally less than 3% nucleotide divergence within viral subtypes and up to 15% nucleotide divergence between viral subtypes in the tax region, the 7% divergence seen in the tax sequences of STLV-3 (from animal Cmo8699AB) and STLV-3 (from animal Cni7867AB), and the clustering of these viruses outside the diversity of other STLV-3-like viruses demonstrate that this virus (denoted STLV-3 subtype D) is a new and highly divergent PTLV-3 subtype (FIG. 3, Table 4). Complete LTR sequences were obtained for 11 of 12 PTLV-positive samples using overlapping primer pairs.

TABLE 3

PTLV infection of wild-caught nonhuman primates from Cameroon

| No. | Code | Species | Common name | Site | Province | PTLV (subtype) |
|---|---|---|---|---|---|---|
| 1 | Cag9812NL | *Cercocebus agilis* | agile mangabey | Ngoila | East | STLV-1 (f) |
| 2 | Cag9813NL | *Cercocebus agilis* | agile mangabey | Ngoila | East | STLV-1 (f) |
| 3 | Cag9748NL | *Cercocebus agilis* | agile mangabey | Ngoila | East | STLV-3 (b) |
| 4 | Cmo8699AB | *Cercopithecus mona* | mona monkey | Abat | Southwest | STLV-3 (d) |
| 5 | Cni10026NL | *Cercopithecus nictitans* | spot-nosed monkey | Ngoila | East | STLV-1[1] |
| 6 | Cni10225NL | *Cercopithecus nictitans* | spot-nosed monkey | Ngoila | East | STLV-1 (d) |
| 7 | Cni8284NY | *Cercopithecus nictitans* | spot-nosed monkey | Nyabissan | South | STLV-1 (d) |
| 8 | Cni8286NY | *Cercopithecus nictitans* | spot-nosed monkey | Nyabissan | South | STLV-1 (d) |
| 9 | Cni8348NY | *Cercopithecus nictitans* | spot-nosed monkey | Nyabissan | South | STLV-1 (d) |
| 10 | Cni7882AB | *Cercopithecus nictitans* | spot-nosed monkey | Abat | Southwest | STLV-3 (b) |
| 11 | Cni7867AB | *Cercopithecus nictitans* | spot-nosed monkey | Abat | Southwest | STLV-3 (d) |
| 12 | Lal9589NL | *Lophocebus albigena* | grey-cheeked monkey | Ngoila | East | STLV-3 (b) |

[1]subtype not determined.

Phylogenetic Resolution of a New STLV-3 Subtype

Figure 4:
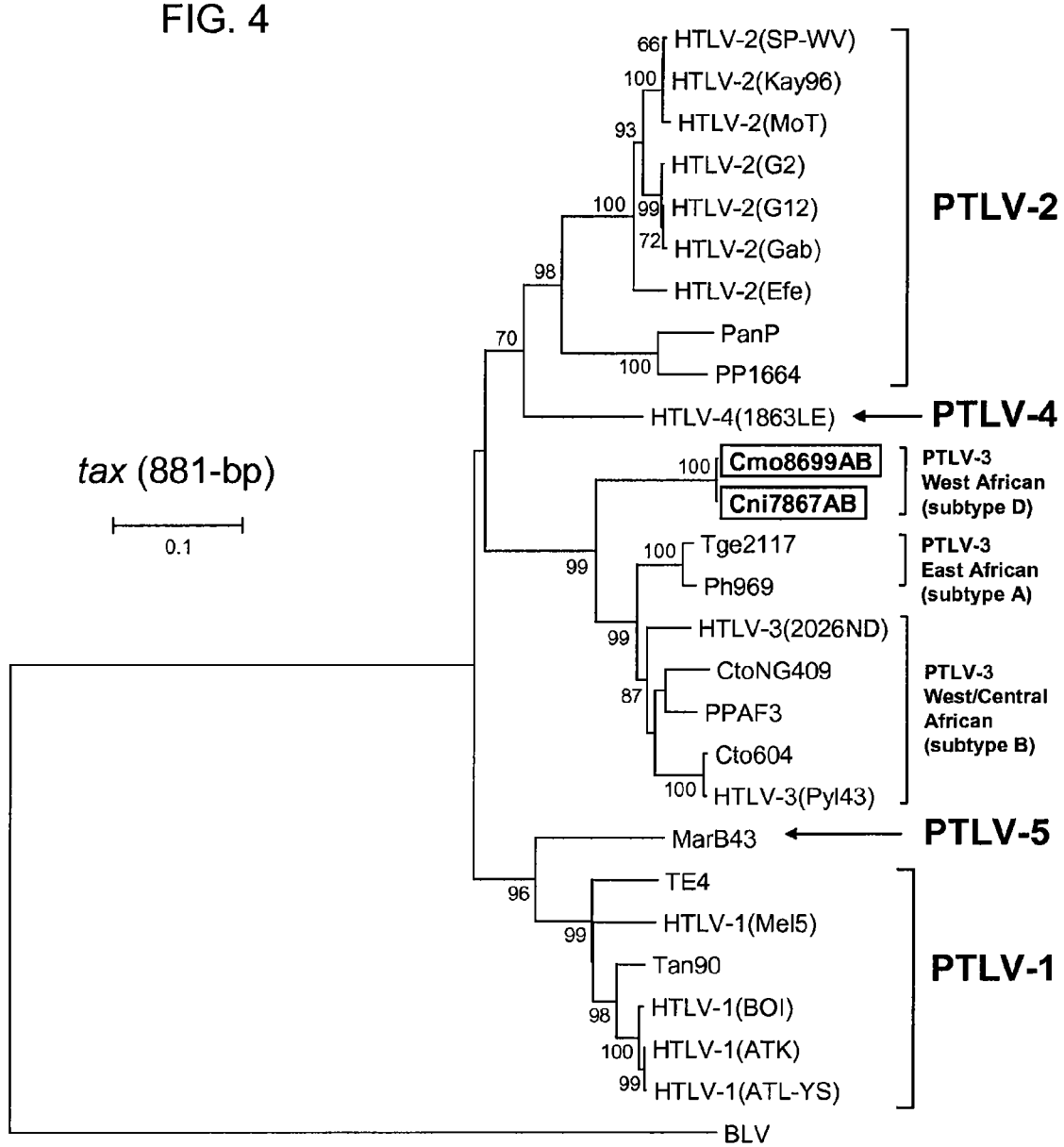
FIG. 4 depicts a phylogenetic tree using an alignment of 881-bp sequences from prototypical PTLVs and bovine leukemia virus (BLV). Sequences were used as an outgroup in the maximum likelihood analysis. New sequences from this study are boxed. NHPs are coded using the first letter of the genus followed by the first two letters of the species name: *C. mona* (Cmo), *Cercopithecus nictitans* (Cni). The last two letters in the sample name indicate the study site. Support for the branching order was determined by 1,000 bootstrap replicates; only values of 60% or more are shown. Branch lengths are proportional to the evolutionary distance (scale bar) between the taxa.

The identification of a new STLV lineage in DBS from animals Cmo8699AB and Cni7867AB was investigated further by additional analyses of a larger tax sequence (1015-bp) obtained from the DBS DNA of these two monkeys. The tax sequences from both monkeys were nearly identical (99.9%) despite nucleic acid extraction, PCR amplification, and sequencing for both animals all being done on different days. Analysis of mitochondrial DNA (mtDNA) sequences also confirmed the different *Cercopithecus* species of each monkey and the absence of admixtures of specimens from different NHP species. Nearly identical STLVs have also been previously reported in monkeys and apes living in close geographic proximity indicating the relative ease with which these viruses jump species boundaries. The STLV-3 (Cmo8699AB) tax sequences were nearly equidistant from all other PTLV groups sharing approximately 72-74% nucleotide identity with PTLV-1, PTLV-2, and PTLV-4 sequences but having closer genetic identity to the PTLV-3 group (82-84%) in this highly conserved region where intragroup sequence identity is typically >90% (Table in FIG. 7). The nucleotide identities of tax sequences from Cmo8699AB and Cni7867AB are more consistent with the observed intergroup sequence identity that ranges from 71 to 83% (Table in FIG. 7). Indeed phylogenetic analysis of 881-bp tax sequences (FIG. 4) from these two monkeys (Cmo8699AB and Cni7867AB) with other PTLVs, using BLV as an outgroup, inferred a new lineage with very high bootstrap support (99) from the diversity of other PTLV-3 subtypes (larger tax sequences representing PTLV-3 subtype C were not available for inclusion in this analysis), suggesting a long independent evolution and the possibility of a yet to be identified human counterpart for these viruses.

Similar results were obtained by analysis of 275-bp LTR sequences (FIG. 5), where STLV-3 (from animal Cmo8699AB) and STLV-3 (from animal Cni7867AB) had only 70-74% identity to LTRs from members of the PTLV-3 group which share greater than 84% nucleotide identity between subtypes A and B. LTR sequences from other STLV-3-infected *C. agilis* and *C. nictitans* from Cameroon reported elsewhere were not available at GENBANK® and thus were not included in the current phylogenetic analysis. Combined, the phylogenetic analyses of the tax sequences (FIGS. 3 and 4) and LTR (FIG. 5) show that STLV-3 (from animal Cmo8699AB) and STLV-3 (from animal Cni7867AB) both form a distinct cluster with high bootstrap support from the other known PTLV-3 subtypes. Based on nomenclature proposed by others, our results demonstrate that these viruses are members of a novel PTLV-3 subtype tentatively named as STLV-3 West African subtype D.

Partial fragments of the env, tax, and LTR regions for the two novel STLV-3-like samples were sequenced (see Table 4). The 174-bp tax fragments for CM08699AB and CNI7867AB are identical, both showing 91% sequence homology to STLV-3 (CTO-604) as well as the two recently described HTLV-3 viruses (2026ND and Py143) from separate individuals in southern Cameroon with reported primate contact. Using specifically designed primers, sequence analysis of the entire tax fragment (1018-bp) for both specimens yielded 85% sequence homology to STLV-3 (TG-2117 and PH969) found in baboons. Analysis of the env gene region revealed that CM08699AB and CNI7867AB shared 95% genetic identity to STLV-1 (Tan 90) and 80% to STLV-3 (CTO-NG409), respectively. Cloning of a portion of the tax gene fragment for the former specimen resulted in identical clones, indicating that the recombinant sequences are not due to mixed infections of STLV-1 and STLV-3.

TABLE 4

STLV-3 subtype D Genome Sequences

| Virus | Gene/Region | SEQ ID NO: | Nucleotide positions |
|---|---|---|---|
| STLV-3 subtype D | LTR | 1 | 7-706 |
| STLV-3 subtype D | Gag | 1 | 747-2009 |
| STLV-3 subtype D | Protease | 1 | 1961-2494 |
| STLV-3 subtype D | Pol | 1 | 2416-5061 |
| STLV-3 subtype D | Env | 1 | 5054-6535 |

TABLE 4-continued

STLV-3 subtype D Genome Sequences

| Virus | Gene/Region | SEQ ID NO: | Nucleotide positions |
|---|---|---|---|
| STLV-3 subtype D tax | 1(SEQ ID NO: 25) | 5054-5057 and 7232-8280 |
| STLV-3 subtype D rex | 1(SEQ ID NO: 25) | 4995-5057 and 7232-7717 |

Phylogenetic analysis of the tax region for these novel sequences clearly supports a significant divergence from the PTLV-3 cluster, indicating that these are the first sequences of a new PTLV group found in the same region of Cameroon.

Primate COII genes were amplified and sequenced to confirm species identification. Eleven of the 12 PTLV-positive specimens were correctly identified using the pictographs and confirmed through mitochondrial DNA analysis. One sample, identified as C. agilis, had high sequence homology to C. torquatus.

The tax region showed 98% homology to STLV-3 (PPAF2), STLV-3 (CT604), as well as HTLV-3 (2026ND), but diverged in a rooted phylogenetic tree analysis of this region. Sequencing and phylogenetic analysis of the LTR region revealed 94% identity and clustered with the LTR of STLV-3 CT604 (C. torquatus).

The use of field-collected DBS in collaboration with hunters provides a good surveillance tool for emerging infections at the primate-hunter interface. Samples collected on DBS yielded sufficient viral DNA for PCR analysis and sequencing.

Based on the samples collected, the prevalence of PTLV among wild monkeys hunted for bush meat in southern Cameroon was found to be 7%, which is comparable to previously published reports. Four of the 8 primate species collected and tested were shown to harbor PTLVs.

Sequence analyses of the env, tax, and LTR gene regions of CM08699AB and CNI7867AB indicate that this novel group is highly divergent from all known PTLV-3 subtypes. The discovery of a novel PTLV subtype (identified herein as STLV-3 subtype D) in the same region where two novel HTLV groups were identified, contributes to the growing evidence that PTLVs have greater diversity and geographic distribution than previously acknowledged. More surveillance of wild primates in contact with human populations particularly via bush meat hunting is needed.

Bush meat hunting, a common practice in many parts of Africa, has been suggested to be an ideal interface for cross-species transmission of retroviruses between primates and humans. Contact with bodily fluids and blood during hunting and butchering of bush meat exposes humans to a plethora of retroviruses, and increases the likelihood of emerging diseases in humans.

Broad STLV-3 Diversity in Wild NHPs from Cameroon

Figure 5:
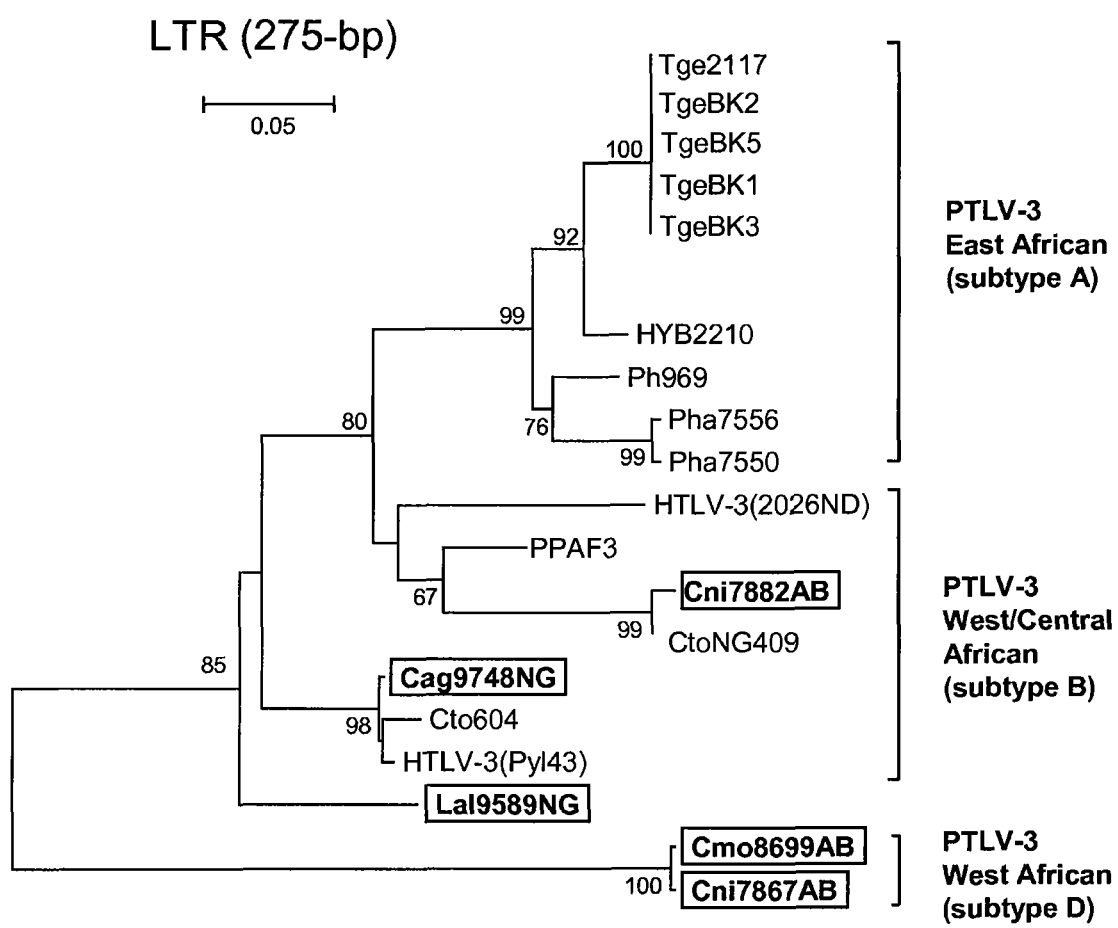
FIG. 5 is a phylogenetic tree that depicts the identification of a novel PTLV-3 subtype by phylogenetic analysis of 275-bp LTR sequences. LTR sequences for PTLV-3 Subtype C were not available for this analysis. NHPs are coded using the first letter of the genus followed by the first two letters of the species name: *Cercocebus agilis* (Cag), *Cercopithecus nictitans* (Cni), *C. mona* (Cmo), and *Lophocebus albigena* (Lal). The last two letters in the specimen name indicate the study site. New sequences from this study are boxed. Support for the branching order was determined by 1,000 bootstrap replicates; only values ≥60% are shown. Branch lengths are proportional to the evolutionary distance (scale bar) between the taxa.

Sequence analysis of the STLV-3 LTR sequences from animals Cni7882AB, Cag9748NL, and Lal9589NL showed that all were infected with distinct STLV-3s. LTR sequences (283-bp) from animal Cag9748NL shared the greatest identity (≥97%) with those from HTLV-3 (Py143) and STLV-3 (Cto604) from a red-capped mangabey from Cameroon. The 282-bp LTR sequence from Cni7882AB shared the highest nucleotide identity (99%) to STLV-3 (CtoNG409), a red-capped mangabey from neighboring Nigeria. The phylogeographic clustering of these sequences supports further the proposed subtype classification of STLV-3 by geographic origin rather than by host species. In contrast, the 432-bp LTR sequence from L. albigena (Lal9589NL) was more divergent sharing only 10-16% nucleotide identity with all PTLV-3 LTR sequences. Similar to the phylogenetic relationships inferred with the small tax sequences, the LTR sequence from L. albigena (Lal9589NL) formed a new lineage within the diversity of other PTLV-3 sequences from west-central Africa (FIG. 5). Although these results will need to be confirmed with additional LTR sequences from this virus and from other STLV-3-infected L. albigena, these findings demonstrate a host range and geographical distribution of STLV-3 that is more widespread than previously considered.

Phylogenetic Analysis of STLV-1 Diversity

Figure 6:
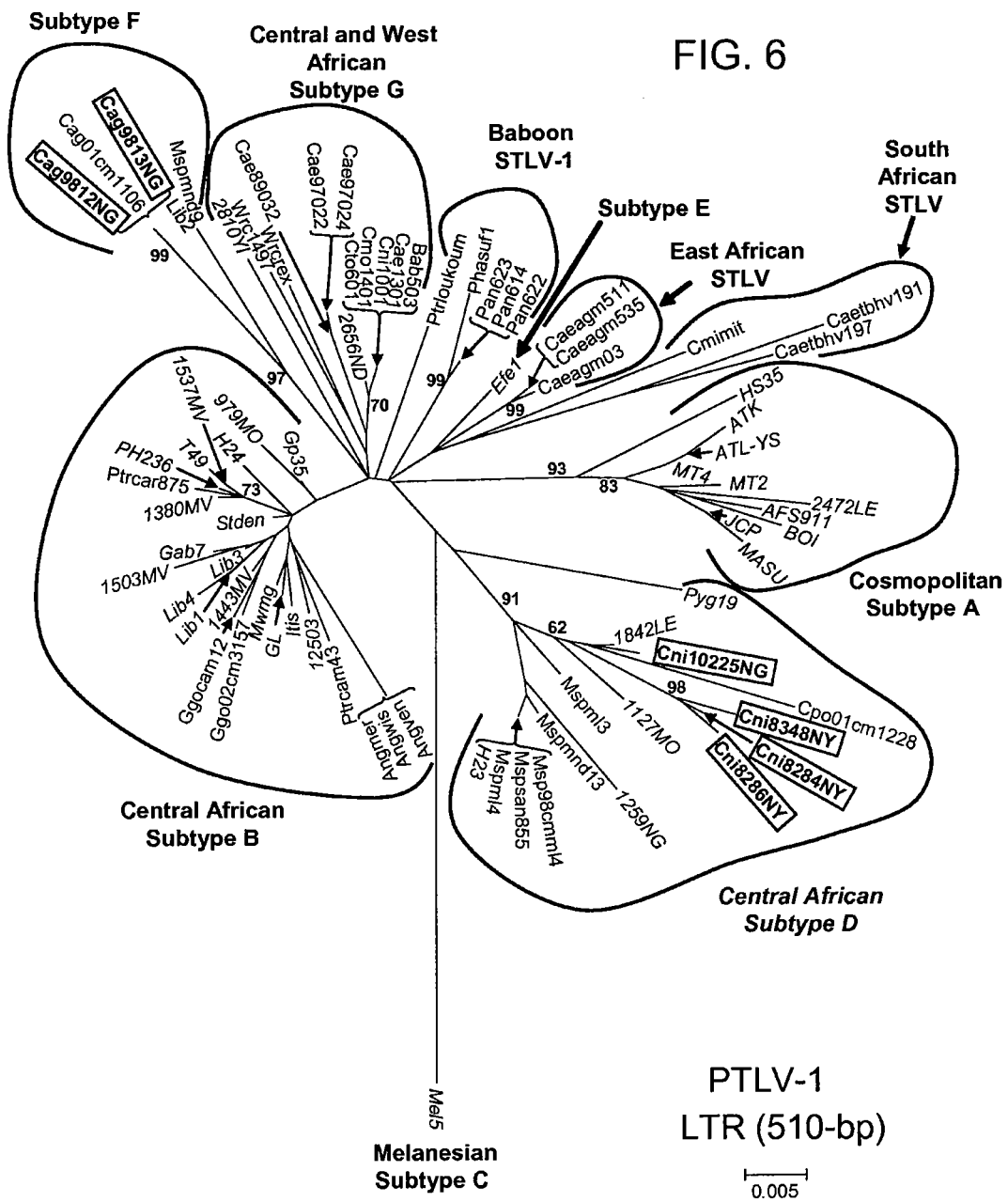
FIG. 6 is a phylogenetic tree depicting the inferred phylogenetic relationships of PTLV-1 LTR sequences by neighbor-joining analysis. Sequences from wild nonhuman primates (NHPs) in Cameroon generated in the current study are boxed. NHPs are coded using the first letter of the genus followed by the first two letters of the species name: *Cercocebus agilis* (Cag) and *Cercopithecus nictitans* (Cni). The last two letters in the monkey name indicate the study site. HTLV-1 sequences are italicized. New sequences from this study are boxed. Support for the branching order was determined by 1,000 bootstrap replicates; only values ≥60% are shown.

To investigate further the genetic relationships inferred with the small PTLV-1-like tax sequences, we obtained LTR sequences for 6 of 7 PTLV-1-positive samples using established primer pair combinations (see Meertens et al., Virology. 287(2):275-85, 2001; Slattery et al., Genome Res. 9(6): 525-40, 1999; Wolfe et al., Proc Natl Acad Sci U S A.; 102 (22):7994-9, 2005. Phylogenetic analysis of these sequences, including those identified from a study of infected primate hunters in Cameroon (Wolfe et al., Proc Natl Acad Sci USA.; 102(22):7994-9, 2005), revealed that four C. nictitans sequences all clustered in the central African HTLV-1 subtype D clade consisting of STLV-1 from Mandrillus sphinx and Cercopithecus pogonias and HTLV-1 sequences from Cameroon (FIG. 6). Interestingly, the STLV-1 (Cni10225NL) LTR sequence was closest phylogenetically to the HTLV-1 (1842LE) strain from a primate hunter from Cameroon (Wolfe et al., Proc Natl Acad Sci U S A.; 102(22):7994-9, 2005) (FIG. 6). Similarly, LTR sequences from two C. agilis (Cag9812NL and Cag9813NL) clustered within the HTLV-1F clade (FIG. 6). Combined, these results support further the primate origin of the HTLV-1D and -1F subtypes. STLV-1 LTR sequences could not be amplified from DBS samples from a C. nictitans (Cni10026NL) that was positive for STLV-1 tax sequences possibly due to either low viral load in this animal, a lower sensitivity of the LTR primers, or genetic variances at the LTR primer binding sites.

Screening for Novel STLV-3 Subtype Sequences in Primate Hunters

Given the prevalence of the STLV-3 subtype D virus in at least two monkey species in Cameroon it was determined whether this new subtype was also present among primate hunters in Cameroon. PBMC DNA samples were available from a previous study from 63 primate hunters with a wide range of WB seroreactivity to HTLV. HTLV sequences were not previously detected in the PBMC DNA of these persons using either generic or group-specific primers (Wolfe et al., Proc Natl Acad Sci U S A.; 102(22):7994-9, 2005). All 63 primate hunters also tested negative for STLV-3 (Cmo8699AB) tax-specific sequences suggesting the absence of this virus in this subset of persons with broad WB seroreactivity to HTLV.

Example 2

PCR Assay for STLV-3 Subtype D Tax Sequences

This example describes an exemplary PCR assay for STLV-3 subtype D infection using primers to the STLV-3 subtype D tax Sequences To screen humans for evidence of STLV-3 subtype D-like infection a nested PCR assay was developed to detect STLV-3 subtype D tax sequences. Similar strategies have been used to detect the novel HTLV-3 and HTLV-4 viruses in primate hunters from Cameroon. Peripheral blood mononuclear cell (PBMC) DNA was available for testing from 63 primate hunters in Cameroon with seroreactivity to HTLV antigens in the Genelabs Diagnostics HTLV Western blot 2.4 kit. The WB profiles for these samples included HTLV-1-like (n=2), HTLV-2-like (n=4), HTLV-positive but untypeable (n=8), and HTLV-indeterminate (n=49). PBMC DNA from all 63 hunters tested negative for sequences using primers that can detect PTLV-1, PTLV-2, PTLV-3, and PTLV-4. The external P5TAXF3 (5'CCC TCA AGG TCC TCA CCC CGC CGC 3', SEQ ID NO: 21) and P5TAXR3 (5' TAA CGG CCA GGT CAT TGG AGG TGT 3', SEQ ID NO: 22) and internal PCR primers P5TAXF2 (5' AAG TTC CTC CCT CCT TCT TCC ATG 3', SEQ ID NO: 23) and P5TAXR1 (TGG TAG AGG TAT AAG CAC ACG ATG GTG 3', SEQ ID NO: 24) were used to amplify 244-bp and 174-bp STLV-3 subtype D sequences, respectively, using standard PCR conditions. The assay could reliably detect 10 copies of STLV-3 subtype D (Cmo8699AB) tax plasmid sequences in a background of human DNA. STLV-3 subtype D tax sequences were not amplified from PTLV-1, PTLV-2, PTLV-3, and HTLV-4 cell line or tax-containing plasmid DNA, or from HTLV nonreactive blood donor DNAs showing the high sensitivity and specificity of the assay.

PCR products were visualized on 1.8% agarose gels stained with ethidium bromide and were purified with Qiaquick® PCR or gel purification kits (QIAGEN®, Valencia, Calif.). Using an ABI 3130×1 sequencer, purified amplicons were then either directly sequenced on both strands using ABI PRISM Big Dye terminator kits (Foster City, Calif.) or after cloning into a TOPO vector (INVITROGEN™, Carlsbad, Calif.).

Example 3

Production of Antibodies to STLV-3 Subtype D Polypeptides

Polyclonal or monoclonal antibodies (including humanized monoclonal antibodies) and fragments of monoclonal antibodies such as Fab, F(ab')$_2$ and Fv fragments, as well as any other agent capable of specifically binding to an STLV-3 subtype D polypeptide, may be produced to the STLV-3 subtype D virion, or any of the STLV-3 subtype D polypeptides (for example STLV-3 subtype D envelope, protease, polymerase, tax, rex, or capsid polypeptides). Optimally, antibodies raised against an STLV-3 subtype D polypeptide would specifically bind the STLV-3 subtype D polypeptide of interest (or a virion containing the STLV-3 subtype D polypeptide of interest). That is, such antibodies would recognize and bind the protein and would not substantially recognize or bind to other proteins found in human or other cells. The determination that an antibody specifically detects the STLV-3 subtype D polypeptide is made by any one of a number of standard immunoassay methods; for instance, the Western blotting technique (Sambrook et al., 1989, Molecular Cloning: A Laboratory Manual, Cold Spring Harbor Laboratory, Cold Spring Harbor, N.Y.).

To determine that a given antibody preparation (such as one produced in a mouse) specifically detects the STLV-3 subtype D polypeptide by Western blotting, total cellular protein is extracted from murine myeloma cells and electrophoresed on a SDS-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect an STLV-3 subtype D polypeptide will, by this technique, be shown to bind to the STLV-3 subtype D polypeptide band (which will be localized at a given position on the gel determined by its molecular weight). Non-specific binding of the antibody to other proteins (such as serum albumin) may occur and may be detectable as a weak signal on the Western blot. The non-specific nature of this binding will be recognized by one skilled in the art by the weak signal obtained on the Western blot relative to the strong primary signal arising from the specific antibody-STLV-3 subtype D polypeptide binding.

A substantially pure virion can be obtained, or substantially pure STLV-3 subtype D polypeptide suitable for use as an immunogen is isolated by purification or recombinant expression. Concentration of protein in the final preparation is adjusted, for example, by concentration on an Amicon filter device, to the level of a few micrograms per milliliter. Monoclonal or polyclonal antibody to the protein can then be prepared as described by Harlow and Lane (Antibodies, A Laboratory Manual, Cold Spring Harbor Press. 1988).

Alternatively, antibodies may be raised against synthetic STLV-3 subtype D polypeptide synthesized on a commercially available peptide synthesizer based upon the predicted amino acid sequence of the STLV-3 subtype D polypeptide (Harlow and Lane, Antibodies, A Laboratory Manual, Cold Spring Harbor Press. 1988).

Another method of raising antibodies against a STLV-3 subtype D polypeptide is by subcutaneous injection of a DNA vector which expresses the STLV-3 subtype D polypeptide into laboratory animals, such as mice. Delivery of the recombinant vector into the animals may be achieved using a handheld form of the Biolistic system (Sanford et al., 1987, *Particulate Sci. Technol.* 5:27-37) as described by Tang et al. (*Nature* 356:152-4, 1992). Expression vectors suitable for this purpose may include those which express the STLV-3 subtype D polypeptide under the transcriptional control of either the human β-actin promoter or the cytomegalovirus (CMV) promoter.

Monoclonal Antibody Production by Hybridoma Fusion

Monoclonal antibody to epitopes of the STLV-3 subtype D polypeptides identified and isolated as described can be prepared from murine hybridomas according to the classical method of Kohler and Milstein (*Nature* 256:495, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (Antibodies: A Laboratory Manual. 1988, Cold Spring Harbor Laboratory, New York).

Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (*J. Clin. Endocrinol. Metab.* 33:988-91, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In: Handbook of Experimental Immunology, Wier, D. (ed.). Chapter 19. Blackwell. 1973). Plateau concentration of antibody is usually in the range of 0.1 to 0.2 mg/ml of serum (about 12 μM). Affinity of the antisera for the antigen is determined by preparing competitive binding curves, as described, for example, by Fisher (Manual of Clinical Immunology, Chapter 42. 1980).

Labeled Antibodies

Antibodies of the present invention can be conjugated with various labels for their direct detection (see Chapter 9, Harlow and Lane, Antibodies: A Laboratory Manual. 1988). The label, which may include, but is not limited to, a radiolabel, enzyme, fluorescent probe, or biotin, is chosen based on the method of detection available to the user.

Example 4

Vaccines

This disclosure provides substances suitable for use as vaccines for the prevention of STLV-3 subtype D infection and methods for administering them. Particular vaccines are directed against STLV-3 subtype D, and may include antigens obtained from STLV-3 subtype D. In one embodiment, the vaccine contains a nucleic acid vector encoding a surface protein of STLV-3 subtype D, such as a capsid protein or a envelope protein or other gene products found to elicit appropriate humoral and/or cell mediated immune responses.

This disclosure also provides a method of vaccinating a subject against STLV-3 subtype D infection, comprising administering to a susceptible subject an effective amount of the peptide or polypeptide encoded by an isolated DNA molecule encoding a polypeptide or combination of polypeptides expressed by the DNA molecule, and a suitable acceptable carrier. In one embodiment, naked DNA is administered to the subject in an effective amount to vaccinate the subject against STLV-3 subtype D infection.

The vaccine can be made using synthetic peptide or recombinantly-produced polypeptide described above as antigen. Typically, a vaccine will include from about 1 to 50 micrograms of antigen, for example from about 15 to about 45 micrograms. Typically, the vaccine is formulated so that a dose includes about 0.5 milliliters. The vaccine may be administered by any route known in the art, for example parenteral, subcutaneous or intramuscular.

There are a number of strategies for amplifying an antigen's effectiveness, particularly as related to the art of vaccines. For example, cyclization of a peptide can increase the peptide's antigenic and immunogenic potency. See U.S. Pat. No. 5,001,049. More conventionally, an antigen can be conjugated to a suitable carrier, usually a protein molecule. This procedure can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets. The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," *Bioconjugate Chem.* 1:2-12 (1990).

Vaccines against STLV-3 subtype D infection can be made from the STLV-3 subtype D envelope glycoproteins and others. These proteins can be purified and used for vaccination (Lasky, *J. Med. Virol.* 31:59, 1990). MHC-binding peptides from cells infected with the human herpesvirus can be identified for vaccine candidates per the methodology of Marloes, et al. *Eur. J. Immunol.* 21:2963-2970, 1991. The STLV-3 subtype D antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionibacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 μg to about 100 μg protein per subject, for example about 1 μg to about 50 μg per dose, or about 15 μg to about 45 μg. A suitable dose size is about 0.5 ml. Accordingly, a dose for intramuscular injection, for example, would comprise 0.5 ml containing 45 μg of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. Also, the antigen could be a component of a recombinant vaccine which is adaptable for oral administration. Vaccines of this disclosure may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral polypeptides from the human herpesvirus. For example, it is known in the protein art that certain amino acid residues can be substituted with amino acids of similar size and polarity without an undue effect upon the biological activity of the protein. The human herpesvirus proteins have significant tertiary structure and the epitopes are usually conformational. Thus, modifications should generally preserve conformation to produce a protective immune response.

Example 5

Peptide Synthesis and Purification

The peptides provided by the present disclosure, such as STLV-3 subtype D polypeptides, can be chemically synthesized by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. *Solid Phase Peptide Synthesis*, IRL Press: Oxford, 1989.

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5-3 hours at room temperature.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

Example 6

Assembly of the STLV-3 Subtype D Genome

This example describes exemplary procedures for assembling the viral genome of STLV-3 subtype D with the sequences provided in Example 8.

As shown in FIG. 1, the sequences provided herein span the entire genome of STLV-3 subtype D. FIG. 1 is a schematic representation of the genome of STLV-3 subtype D. At the top of FIG. 1 is a block representation of the genes making up the STLV-3 subtype D genome. Positions of the primers used in sequencing the genome are shown relative to the genome (shown in kilobases kB). Shown below the position of the primers in block diagrams are the position of sequenced portions of the STLV-3 subtype D genomes obtained from each animal. Using the sequences obtained, the entire genome of STLV-3 subtype D was assembled. An exemplary sequence of the genome of the STLV-3 subtype D virus is set forth as SEQ ID NO: 1.

Example 7

Isolation of STLV-3 Subtype D

This example describes how STLV-3 subtype D is isolated using the STLV-3 subtype D nucleic acid sequences disclosed herein. Using primers designed from the STLV-3 subtype D nucleic acid sequences disclosed herein, the entire genome of STLV-3 subtype D was sequenced and cloned. Nucleic acid vectors including the entire STLV-3 subtype D genome are introduced into cell cultures of primate cells, for example primate leukocytes, thereby producing STLV-3 subtype D virus. STLV-3 subtype D virus can subsequently be isolated from supernatants, for example by centrifugation to remove cellular material. Viral particles can be further purified, for example with gradient centrifugation or immunoaffinity chromatography, for example using antibodies raised against the STLV-3 subtype D polypeptides disclosed herein.

The presence of isolated STLV-3 subtype D viruses is confirmed by PCR with STLV-3 subtype D specific primers. Alternatively, the presence of isolated STLV-3 subtype D viruses is confirmed with antibodies that specifically recognize STLV-3 subtype D polypeptides.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. An isolated nucleic acid molecule encoding a STLV-3 subtype D (simian T-cell lymphotropic virus type 3 West African subtype D) polypeptide comprising a nucleic acid sequence at least 95% identical to one of: nucleotides 747-2009 of SEQ ID NO: 1; nucleotides 1961-2494 of SEQ ID NO: 1; nucleotides 2416-5061 of SEQ ID NO: 1; nucleotides 5054-6535 of SEQ ID NO: 1; SEQ ID NO: 25; or SEQ ID NO: 26; and a *heterologous promoter*; wherein the isolated nucleic acid molecule is *operably* linked to the heterologous *promoter*.

2. A vector comprising the nucleic acid molecule of claim 1.

3. An isolated host cell transformed with the vector of claim 2.

4. The vector of claim 2, wherein the vector is a viral vector.

5. An isolated viral particle comprising the viral vector of claim 4.

6. The isolated nucleic acid molecule of claim 1, wherein the isolated nucleic acid molecule encoding a STLV-3 subtype D (simian T-cell lymphotropic virus type 3 West African subtype D) polypeptide comprises a nucleic acid sequence 100% identical to one of: nucleotides 747-2009 of SEQ ID NO: 1; nucleotides 1961-2494 of SEQ ID NO: 1; nucleotides 2416-5061 of SEQ ID NO: 1; nucleotides 5054-6535 of SEQ ID NO: 1; SEQ ID NO: 25; or SEQ ID NO: 26.

7. The isolated nucleic acid molecule of claim 1, wherein the isolated nucleic acid molecule encoding a STLV-3 subtype D (simian T-cell lymphotropic virus type 3 West African subtype D) polypeptide consists of a nucleic acid sequence according to one of: nucleotides 747-2009 of SEQ ID NO: 1; nucleotides 1961-2494 of SEQ ID NO: 1; nucleotides 2416-5061 of SEQ ID NO: 1; nucleotides 5054-6535 of SEQ ID NO: 1; SEQ ID NO: 25; or SEQ ID NO: 26.

8. An isolated nucleic acid molecule comprising an isolated STLV-3 subtype D virus comprising a nucleic acid sequence at least 95% identical to SEQ ID NO: 1 and a heterologous promoter, wherein the isolated nucleic acid molecule is operably linked to the heterologous promoter.

* * * * *